(12) United States Patent
Choi

(10) Patent No.: US 11,189,192 B2
(45) Date of Patent: Nov. 30, 2021

(54) DIGITAL APPARATUS AND APPLICATION FOR TREATING MYOPIA

(71) Applicant: S-Alpha Therapeutics Inc., Seoul (KR)

(72) Inventor: Seung Eun Choi, Seoul (KR)

(73) Assignee: S-Alpha Therapeutics Inc., Seoul (KR)

(*) Notice: Subject to any disclaimer, the term of this patent is extended or adjusted under 35 U.S.C. 154(b) by 0 days.

(21) Appl. No.: 16/883,369

(22) Filed: May 26, 2020

(65) Prior Publication Data

US 2021/0118544 A1    Apr. 22, 2021

(30) Foreign Application Priority Data

Oct. 18, 2019     (KR) ................. 10-2019-0130146

(51) Int. Cl.

| | |
|---|---|
| *G09B 19/00* | (2006.01) |
| *A61B 5/024* | (2006.01) |
| *A61B 5/11* | (2006.01) |
| *G16H 20/30* | (2018.01) |
| *G16H 10/60* | (2018.01) |

(Continued)

(52) U.S. Cl.
CPC .............. *G09B 19/00* (2013.01); *A61B 3/113* (2013.01); *A61B 5/024* (2013.01); *A61B 5/1118* (2013.01); *A61B 5/4806* (2013.01); *G06F 3/013* (2013.01); *G06F 3/017* (2013.01); *G16H 10/60* (2018.01); *G16H 20/30* (2018.01); *G16H 20/60* (2018.01)

(58) Field of Classification Search
CPC ....... G61H 20/30; A61B 3/113; A61B 5/4041; G06F 3/013; G06F 3/017; A61F 9/00806; G16H 80/00; G02B 27/017; G02B 30/26; A61H 5/00; G06Q 50/22
See application file for complete search history.

(56) References Cited

U.S. PATENT DOCUMENTS 6,654,724 B1 * 11/2003 Rubin ................... G16H 50/70
                                                                              705/3
8,002,409 B2      8/2011 Li et al.

(Continued)

FOREIGN PATENT DOCUMENTS

| JP | 2002-058744 A | 2/2002 |
|---|---|---|
| JP | 2010-148737 A | 7/2010 |

(Continued)

OTHER PUBLICATIONS

Schmid 'Myopia Manual' Jan. 2017 (Year: 2017).*

(Continued)

*Primary Examiner* — Patrick Fernandes
(74) *Attorney, Agent, or Firm* — Morgan, Lewis & Bockius LLP

(57) ABSTRACT

Systems and methods for treating myopia are provided. A system may include a digital apparatus, which may include a digital instruction generation unit configured to generate digital therapeutic modules for treating myopia based on a mechanism of action (MOA) in and a therapeutic hypothesis for the myopia, generate specified digital instructions based on the digital therapeutic modules and provide the digital instructions to a first user, and an outcome collection unit configured to collect the first user's execution outcomes of the digital instructions. The system may also include a healthcare provider portal for a healthcare provider to manage their patients and/or an administrative portal.

43 Claims, 77 Drawing Sheets

(51) Int. Cl.
G16H 20/60 (2018.01)
A61B 5/00 (2006.01)
A61B 3/113 (2006.01)
G06F 3/01 (2006.01)

(56) References Cited

U.S. PATENT DOCUMENTS

| | | | | |
|---|---|---|---|---|
| 2001/0028437 | A1* | 10/2001 | Beresford | A61H 5/00 351/203 |
| 2003/0214630 | A1* | 11/2003 | Winterbotham | A61H 5/00 351/203 |
| 2005/0001980 | A1* | 1/2005 | Spector | A61B 5/4041 351/203 |
| 2007/0161972 | A1* | 7/2007 | Felberg | A61F 9/00806 606/4 |
| 2008/0077437 | A1* | 3/2008 | Mehta | G06Q 50/22 705/2 |
| 2014/0055337 | A1* | 2/2014 | Karlsson | G06F 3/013 345/156 |
| 2017/0192504 | A1* | 7/2017 | Simmons | G02B 30/26 |
| 2017/0293356 | A1 | 10/2017 | Khaderi et al. | |
| 2018/0074322 | A1* | 3/2018 | Rousseau | G02B 27/017 |
| 2018/0140181 | A1 | 5/2018 | Brennan et al. | |
| 2018/0228364 | A1 | 8/2018 | Brennan et al. | |
| 2019/0019573 | A1* | 1/2019 | Lake | G16H 80/00 |

FOREIGN PATENT DOCUMENTS

| | | |
|---|---|---|
| KR | 10-2005-0055092 A | 6/2005 |
| KR | 10-2006-0006805 A | 1/2006 |
| KR | 10-0692319 B1 | 3/2007 |
| KR | 10-2014-0085846 A | 7/2014 |
| KR | 10-2015-0111011 A | 10/2015 |
| KR | 10-2016-0107552 A | 9/2016 |
| KR | 10-2017-0130493 A | 11/2017 |
| KR | 10-2018-0052892 A | 5/2018 |
| KR | 10-2018-0119505 A | 11/2018 |
| KR | 10-1924125 B1 | 11/2018 |
| KR | 10-1938136 B1 | 4/2019 |
| WO | 2016/151364 A1 | 9/2016 |

OTHER PUBLICATIONS

Hill et al., "Exercise and circulating cortisol levels: The intensity threshold effect," Journal of Endocrinological Investigation, 31: 587-591 (2008).
Kabali et al., "Exposure and Use of Mobile Media Devices by Young Children," Pediatrics, 136 (6): 1044-1050 (2015).
Khalfa et al., "Effects of Relaxing Music on Salivary Cortisol Level after Psychological Stress," Annals New York Academy of Sciences, 999: 374-376 (2003).
Goldspink, "Research on mechano growth factor: its potential for optimising physical training as well as misuse in doping," British Journal of Sports Medicine, 39: 787-788 (2005).
Alessandri et al., "A Revised Version of Kremen and Block's Ego Resiliency Scale in an Italian Sample," TPM,14 (3-4): 165-183 (2007).
Zhou et al., "Dopamine signaling and myopia development: What are the key challenges," Progress in Retinal and Eye Research, 61: 60-71 (2017).
Daniele et al., "Effects of exercise on depressive behavior and striatal levels of norepinephrine, serotonin and their metabolites in sleep-deprived mice," Behavioural Brain Research, 332: 16-22 (2017).
Harper et al., "The Dynamic Sclera: Extracellular Matrix Remodeling in Normal Ocular Growth and Myopia Development," Experimental Eye Research, 133: 100-111 (2015).
Lee et al., "Positional Change of Optic Nerve Head Vasculature during Axial Elongation as Evidence of Lamina Cribrosa Shifting: Boramae Myopia Cohort Study Report 2," Ophthalmology, 125 (8): 1224-1233 (2018).

Dolgin, "The Myopia Boom: Short-Sightedness is Reaching Epidemic Proportions. Some Scientists Think They Have Found a Reason Why," Nature, 519: 276-278 (2015).
Kirby et al., "Elongation of cat eyes following neonatal lid suture," Investigative Ophthalmology & Visual Science, 22 (2): 274-277 (1982).
Park, "The Influence of Ego-Resiliency on School Adjustment in Children: The Moderated Mediating Effect of Stress by Self-Concept," Korean Journal of Child Studies, 35 (3): 1-14 (2014) (see English abstract).
Park et al., "Fun Factors by Game Genre," the Journal of the Korea Contents Association, 7 (12): 20-29 (2007) (see English abstract).
Shim, "Validation of the Neff's Self-Compassion Scale for the Children in Korea," the Journal of Korea Elementary Education, 24 (4): 19-36 (2013) (see English abstract).
Kim et al., "PTSD Symptom Reduction with Mindfulness-Based Stretching and Deep Breathing Exercise: Randomized Controlled Clinical Trial of Efficacy," the Journal of Clinical Endocrinology & Metabolism, 98 (7): 2984-2992 (2013).
Blase et al., "Heart Rate Variability, Cortisol and Attention Focus During Shamatha Quiescence Mediation," Applied Psychophysiology and Biofeedback, 44: 331-342 (2019).
Ooishi et al., "Increase in salivary oxytocin and decrease in salivary cortisol after listening to relaxing slow-tempo and exciting fast-tempo music," PLOS One, 12 (12): e0189075 (2017).
Christensen et al., "Evidence that Increased Scleral Growth Underlies Visual Deprivation Myopia in Chicks," Investigative Ophthalmology & Visual Science, 32 (7): 2143-2150 (1991).
Kim et al., "Longitudinal Changes of Optic Nerve Head and Peripapillary Structure during Childhood Myopia Progression on OCT: Boramae Myopia Cohort Study Report 1," Ophthalmology, 125 (8): 1215-1223 (2018).
Hori et al., "Tickling increases dopamine release in the nucleus accumbens and 50kHz ultrasonic vocalizations in adolescent rats," NeuroReport, 24 (5): 241-245 (2013).
Lee et al., "Change of Beta-Zone Parapapillary Atrophy During Axial Elongation: Boramae Myopia Cohort Study Report 3," Investigative Ophthalmology & Visual Science, 59 (10): 4020-4030 (2018).
Rechichi et al., "Video Game Vision Syndrome: A New Clinical Picture in Children?," Journal of Pediatric Ophthalmology & Strabismus, 54 (6): 346-355 (2017).
Baskerville et al., "Dopamine and Oxytocin Interactions Underlying Behaviors: Potential Contributions to Behavioral Disorders," CNS Neuroscience & Therapeutics, 16: e92-e123 (2010).
Lippert et al., "Time-dependent assessment of stimulus-evoked regional dopamine release," Nature Communications, 10: 336 (2019).
Min et al., "Development of a Daliy Hassles Scale for School Age Children," Korean Journal of Child Studies, 19 (2): 77-96 (1998) (see English abstract).
Kan et al., "Chinese Eye Exercises and Myopia Development in School Age Children: A Nested Case-control Study," Scientific Reports, 6: 28531 (2016).
Oh, "Prevention and Treatment of School Myopia," Journal of the Korean Medical Association, 50 (3): 259-264 (2007) (see English abstract).
Brecha et al., "Enkephalin-containing amacrine cells in the avian retina: Immunohistochemical localization," PNAS, 76 (6): 3010-3014 (1979).
Pyo et al., "Phenotypical Stability and Matrix Synthesis of Human Intervertebral Disc Cells in Response to Dexamethasone and Transforming Growth Factor Beta1," 12 (2): 91-100 (2005) (see English abstract).
Work and love. "The Importance of Correct Posture" Naver blog, [online], URL: https://blog.naver.com/ahnhg2000/221267391307 (2018).
Office Action in Korean Patent Application No. 10-2019-0130146 dated Sep. 29, 2020.
International Search Report issued in related International Patent Application No. PCT/KR2021/004800 dated Aug. 13, 2021.

* cited by examiner

FIG. 7A

| ENVIRONMENT SETUPS ||
|---|---|
| INSTRUCTIONS | EXECUTION |
| • ILLUMINANCE MEASUREMENT/CONTROL<br>• LIGHT ENVIRONMENT ALERT<br>• … | • USING LUX METER APP<br>• PATIENT'S PARTICIPATION<br>• … |

FIG. 7B

| EYE EXERCISE MODULE ||
|---|---|
| INSTRUCTIONS | EXECUTION |
| • EYEBALL EXERCISE<br>• EYE BLINKING<br>• STARING INTO DISTANCE<br>• EYE CLOSING<br>• … | • PATIENT'S ADHERENCE MONITORING USING GAZE TRACKING TECHNOLOGY<br>• PATIENT'S PARTICIPATION<br>• … |

FIG. 7C

| PHYSICAL EXERCISE MODULE ||
|---|---|
| INSTRUCTIONS | EXECUTION |
| • RELAXATION EXERCISE<br>• DEEP BREATHING<br>• MEDITATION<br>• … | • PATIENT'S PARTICIPATION<br>• … |

FIG. 7D

| EGO MODULE | |
|---|---|
| INSTRUCTIONS | EXECUTION |
| • CONVERSATION<br>• DRAWING<br>• MEDITATION<br>• DIARY WRITING<br>• MAKING HIS/HER OWN SAFE SPACE<br>• HIS/HER FAVORITES<br>• HIS/HER OWN BUCKET LIST<br>• TRAVEL PLANS<br>• ... | • PATIENT'S PARTICIPATION<br>• AI<br>• ... |

FIG. 7E

| SAFETY/COMFORT MODULE | |
|---|---|
| INSTRUCTIONS | EXECUTION |
| • CHATTING<br>• EXPRESSION (WRITING, SINGING, DRAWING)<br>• LEAVING UNPLEASANT EMOTIONS<br>• ... | • PATIENT'S PARTICIPATION<br>• GUARDIAN'S GUIDANCE<br>• ... |

FIG. 7F

| FUN MODULE | |
|---|---|
| INSTRUCTIONS | EXECUTION |
| • GAME<br>• MUSIC<br>• VIDEO<br>• … | • PATIENT'S PARTICIPATION<br>• MUTUAL COMMUNICATION BETWEEN PATIENT AND APPLICATION<br>• LEVEL-UP<br>• … |

FIG. 7G

| ACCOMPLISHMENT MODULE | |
|---|---|
| INSTRUCTIONS | EXECUTION |
| • TASK<br>• GUARDIAN COMPLIMENT<br>• DTX LITERACY<br>• … | • PATIENT'S PARTICIPATION<br>• COMPENSATION THROUGH PATIENT-GUARDIAN AND PATIENT-DOCTOR RELATIOSHIP<br>• … |

1.1 Splash

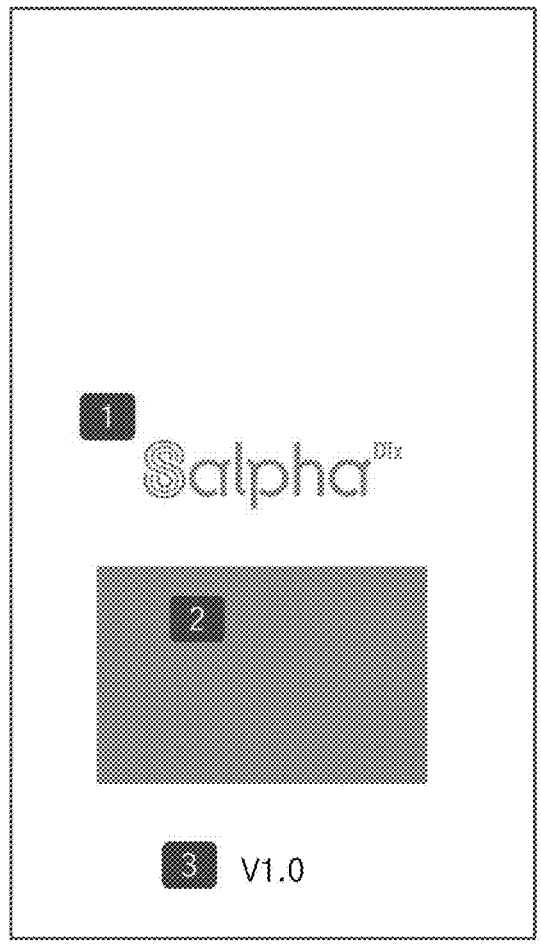

| ID | 1.1 iOS Camera Access Pop-up (iOS pop-up) |
|---|---|

"S Alpha Myopia" Would Like to Access the Camera

To detect face and eye movement.

Don't Allow     OK

| ID | 1.2 Airplane Mode Notification (iOS pop-up) |
|---|---|

Turn Off Airplane Mode or Use Wi-Fi to Access Data

Settings     OK

| ID | 1.3 No Network Notification |
|---|---|
| Title | No Internet Connection |
| Content | Please check your connection and try again. |
| Button | Button[OK] : close the pop-up |
| ID | 1.4 Appstore Update Notification |
| Title | App Update |
| Content | New version is available. Please visit the App Store to update to the latest version. |
| Button | [Update] : Opens App Store > Moves to App Store app screen |

FIG. 21

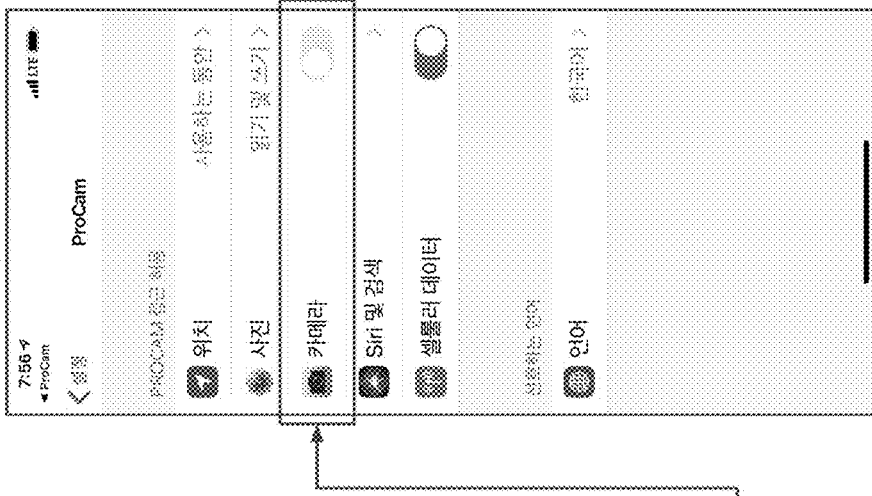
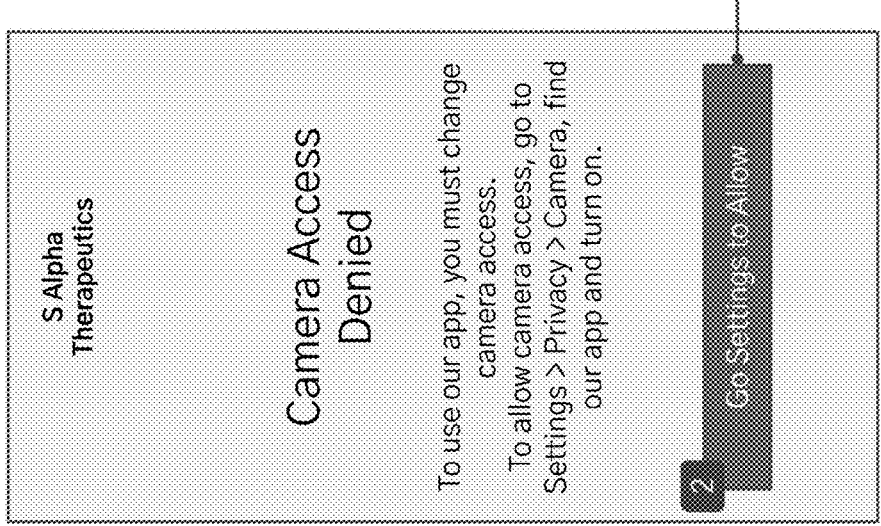
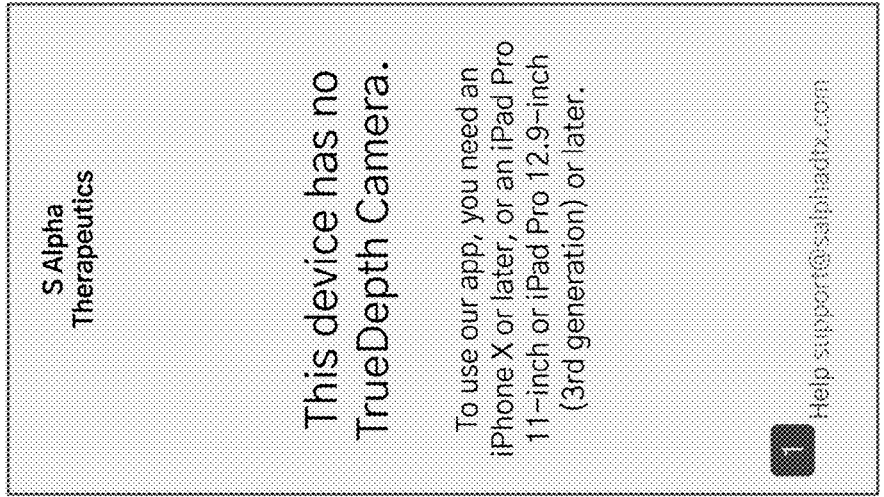
FIG. 22

 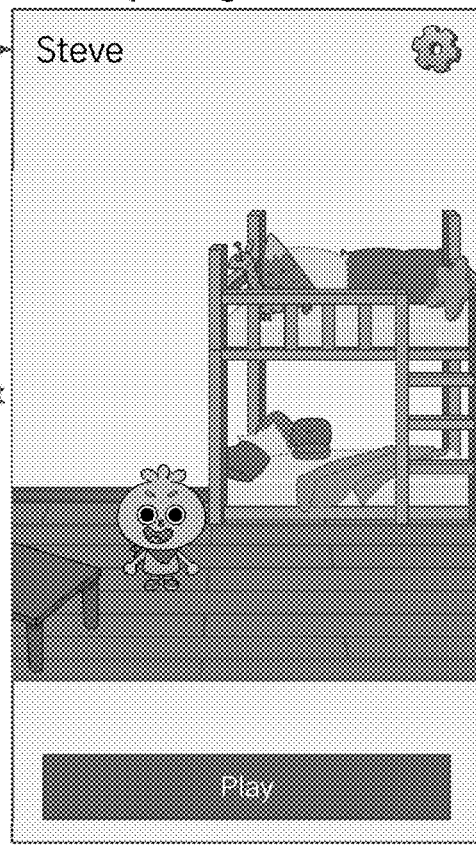
FIG. 24

4.1.1 Calibration Notification

Parent guide

1. Place your phone on the stand.

2. Have your child sit comfortably in the chair and look at the phone.
! It should be done in a bright environment.

3. Help your child.
– Keep child's head still so that only eyes can move.
– Let your child follow the sound instructions without looking at the screen.

Ready!

4.1.2 Calibration Process

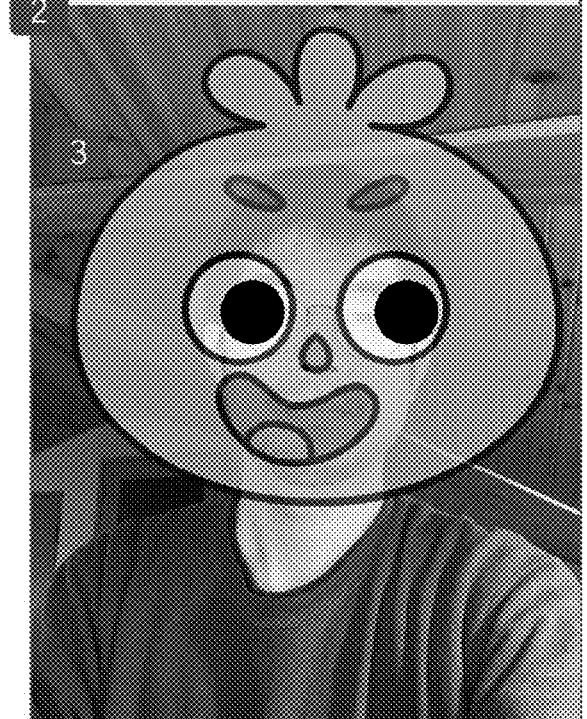
show your face on the screen

FIG. 25

- Timer starts from 30 seconds. The game finishes when the timer reaches 0 second.
- Three cloud icons are in the sky, each moving towards the right side at a slightly different pace.
- The penguin appears from the middle. It is animated to waddle, always moving from side to side per 500 ms.

The penguin can locate in either of the three directions referred to as ▓left side/▓middle/▓right side. The movement of the penguin is controlled by the eyes.

However, the movement is only triggered when the user stares at a single direction for more than 800 ms.

For example, if the penguin is on the ▓left side and the user stares at the right side for more than 800 ms, the penguin will move to the ▓middle. If the user again stares at the right side for more than 800 ms, the penguin will move to the ▓right side.

For every move, there will be background sound to notify the move.
Sound: https://freesound.org/people/cameronmusic/sounds/403360/

When the session starts, fish will appear for every 3 seconds.
(The time is subject to change.)
A total of 10 fish will appear on the screen. The fish will be located evenly in all three sides so that the user can execute sufficient eye exercise.

- Fish gets closer (larger) to the penguin as can be seen from the image. The closeness is classified into 7 stages. The fish approaches to the penguin, one stage per one second.

When the fish reaches at stage 7 (the penguin's location), the penguin can eat the fish. (Success) If the penguin eats the fish, the fish disappears and sound effect is played.
(https://freesound.org/people/institutchaignaud/sounds/445111/)

If the penguin does not eat the fish even if it reached stage 7 location for more than 1.5 seconds, the fish automatically disappears Estimation: 30 seconds

- Adds a button which allows to stop the session during the program.
When clicking the button, the session is temporarily stopped and the 4.3.3. Session stop verification pop-up appears (add v1.3)

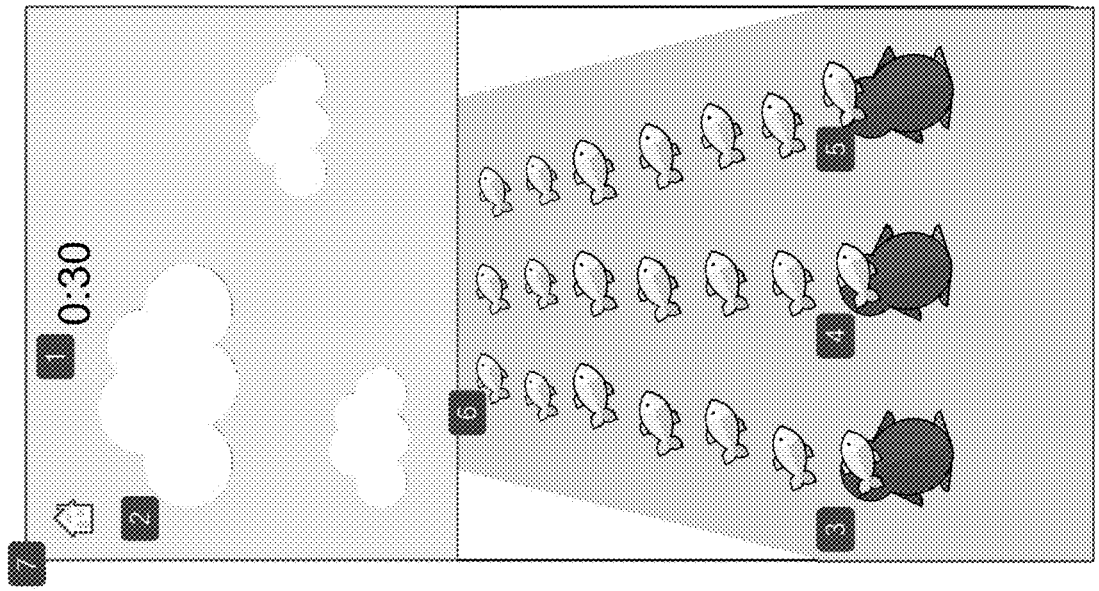

FIG. 26A

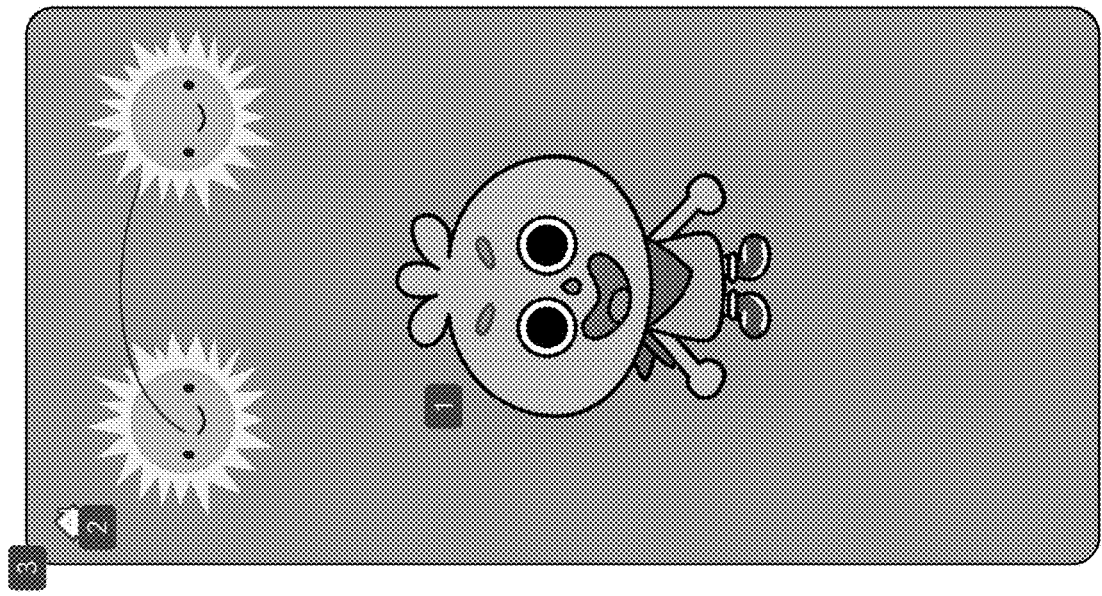

FIG. 27A

- The character appears in the middle.
- The sun icon moves alongside the red line for 30 seconds. (very slowly...)

- According to voice guidance,
- the character blinks its eyes.
- the character stretches out its arms to both sides.

Estimation: 30 seconds

- Adds a button which allows to stop the session during the program.
  When clicking the button, the session is temporarily stopped and the 4.3.3. Session stop verification pop-up appears (add v1.3)

- The timer starts at 30 seconds and ends at 0 second.
- There are three cloud icons in the sky moving towards the right side, each at a slightly different pace.

- The pinwheel takes basic movements to show that it can spin.
Basic movements : Spin for about 10 degree and then return back to its default status.

The pinwheel can spin either clockwise or counter clockwise.
If the voice guidance asks to spin clockwise,
the user exercises his/her eyes in a clockwise circle, and the pinwheel will spin.
There will be background sound effect to let the patient know if it is working.

The exercise lasts for 30 seconds, by repeating 3-second long clockwise eye exercise and 3-second long counter clockwise eye exercise.

Estimation: 30 seconds

- Adds a button which allows to stop the session during the program.
When clicking the button, the session is temporarily stopped and the 4.3.3. Session stop verification pop-up appears (add v1.3)

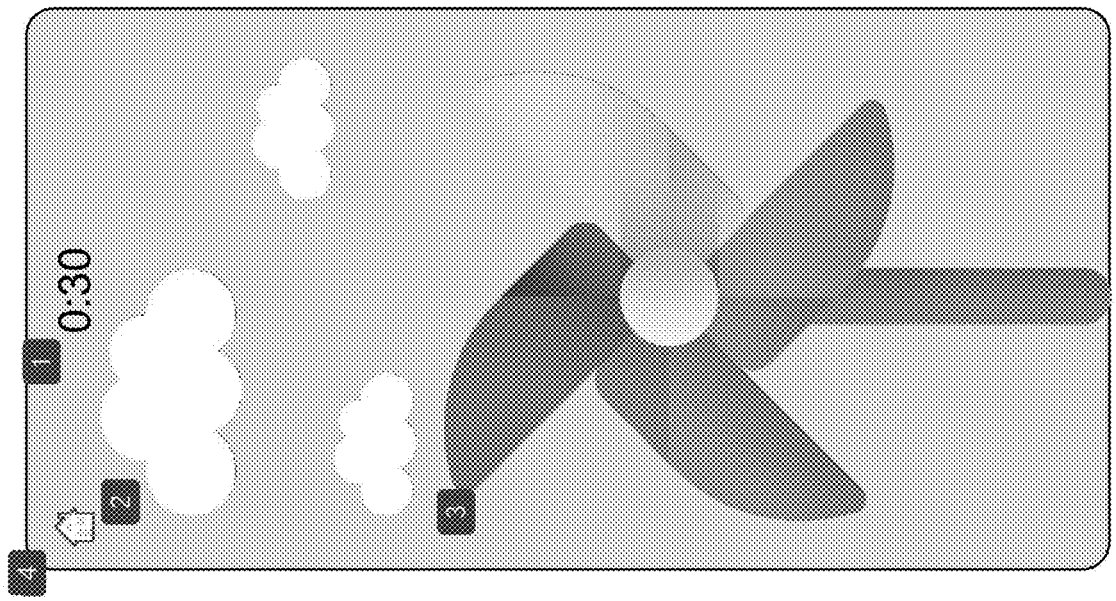

FIG. 28A

- The character appears as shown in the image in the left.
- The character behaves as if it lightly breathes in and out.

According to voice guidance,
- The character blinks its eyes

Estimation: 30 seconds

- Adds a button which allows to stop the session during the program. When clicking the button, the session is temporarily stopped and the 4.3.3. Session stop verification pop-up appears (add v1.3)

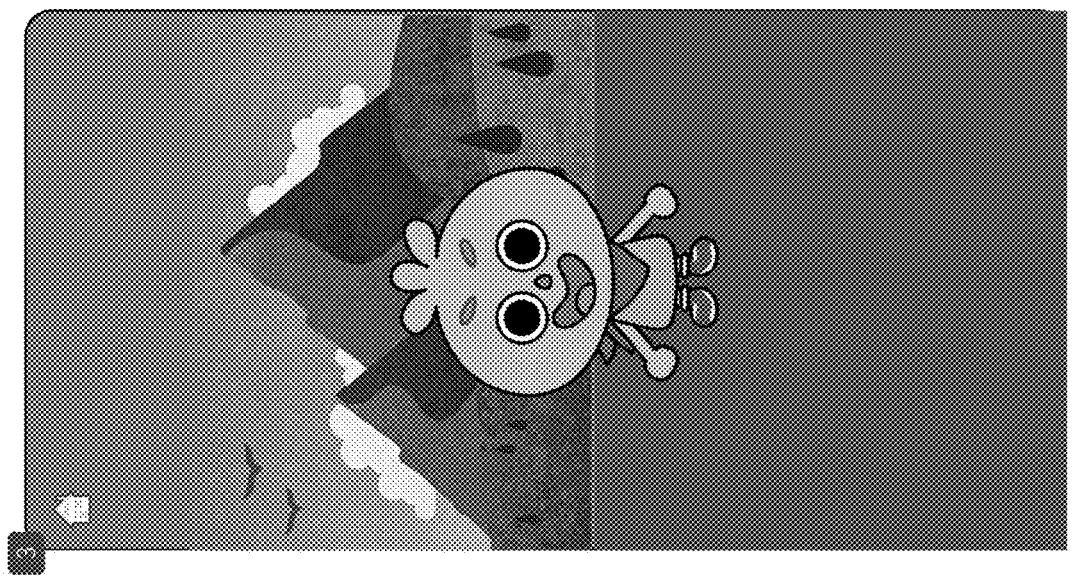

FIG. 29A

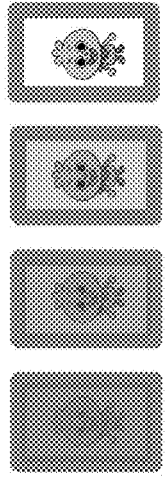 The timer starts at 30 seconds and ends at 0 second.

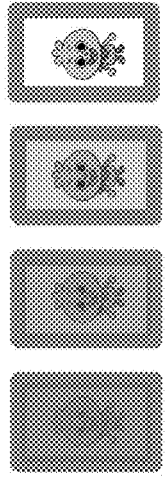 There are windows, 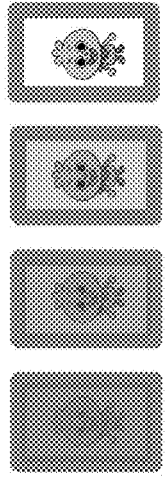 and the characters are standing behind the windows. The windows are grey and semitransparent so that they seem like they are covered with layers of dust. The level of transparency is classified into four stages. The user has to execute multiple eye exercises to clean the windows.

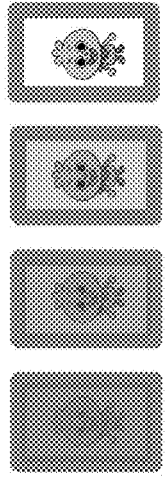 The cleaning tool locates in the bottom side of the screen and is moved in accordance with the user's eye movement. The tools move upwards (or downwards) only when the user starts the upper side (or the bottom side) for more than 1.5 seconds. (The tool moves from the bottom to the top and vice versa at once; it does not stop in the middle.)

After finishing a cycle of eye movement (from upwards to downwards and then going upwards again), the user will reach the next level of transparency of 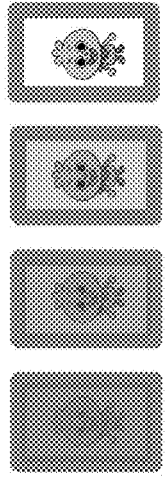. (The exercise is completed if the user finished the total of three cycles.)

Estimation: 30 seconds

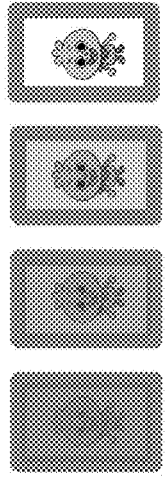 Adds a button which allows to stop the session during the program.
When clicking the button, the session is temporarily stopped and the 4.3.3. Session stop verification pop-up appears (add v1.3)

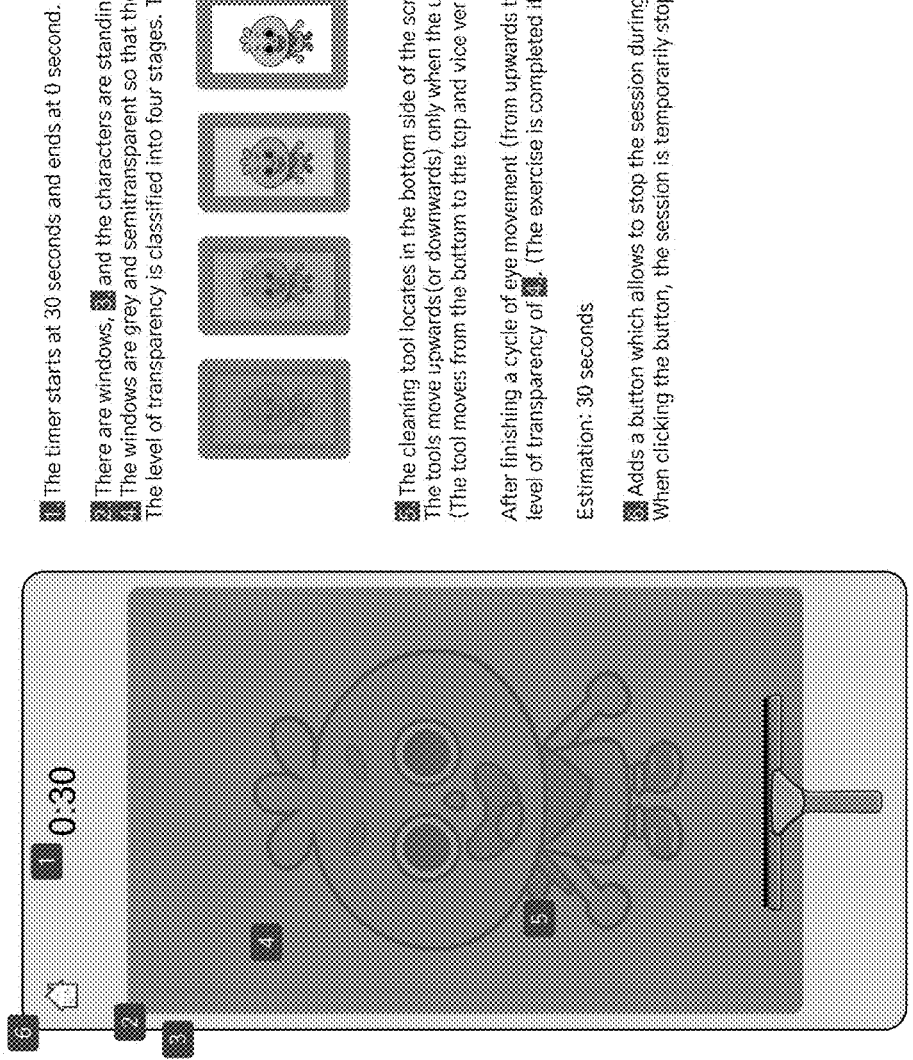

FIG. 30A

▓ The balloon and ▓ the character appear as shown in the image in the left.
The balloon moves up and down per 500 ms so that it seems as if it is lightly floating.

▓ The character behaves as if it lightly breathes in and out.

According to voice guidance,
When the user breathes in ▓ the balloon gets bigger, ▓ and the character behaves as if it lightly, too, is breathing in. (2 seconds)
When the user breathes out ▓ the balloon gets smaller, ▓ and the character behaves as if it lightly, too, is breathing out. (2 seconds)

A total of three sets needs to be completed.

Reference video: https://www.youtube.com/watch?v=2FrOmxEWsWA

Estimation: 30 seconds

▓ Adds a button which allows to stop the session during the program.
When clicking the button, the session is temporarily stopped and the 4.3.3. Session stop verification pop-up appears (add v1.3)

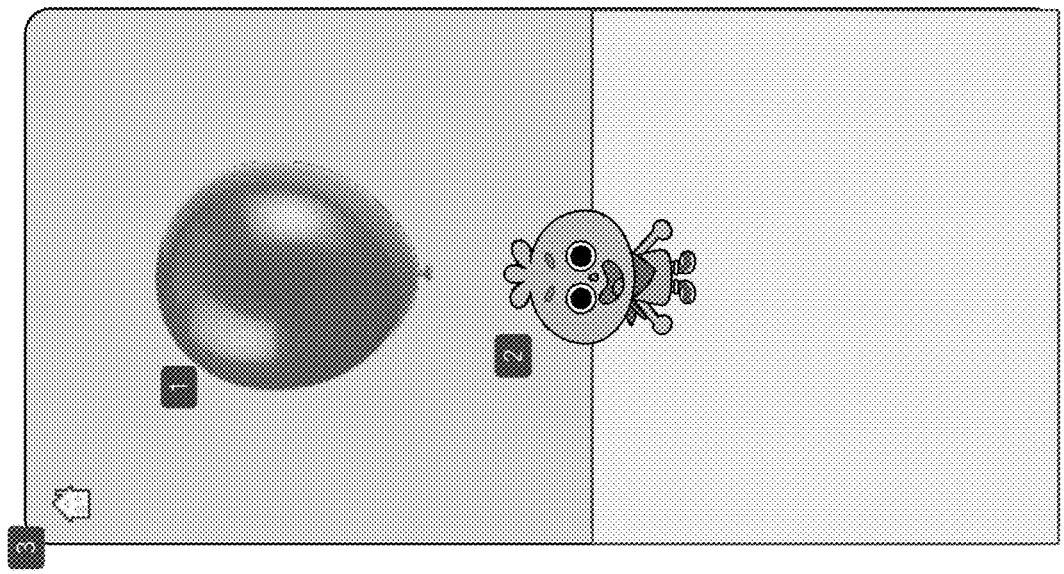

FIG. 31A

- The timer starts at 30 seconds and ends at 0 second.
- The carrot locates at 12, 3, 6, 9 o' clock position.
- When the carrot is at 12 o' clock – The rabbit and the slingshot is at 6 o' clock.
  - Carrot 12 o' clock – Rabbit 6 o' clock
  - Carrot 3 o' clock – Rabbit 9 o' clock
  - Carrot 6 o' clock – Rabbit 12 o' clock
  - Carrot 9 o' clock – Rabbit 3 o' clock
- The slingshot and the rabbit move alongside the user's eye movement. When the eyes move for a certain direction for more than 800 ms, the slingshot moves counter side the carrot, and when the eyes stay unmoved for 2 seconds, the rabbit moves towards the carrot. (Refer The slingshot and the bird from Angry Bird)

When the rabbit approaches and touches the carrot, the rabbit stops moving towards and the carrot disappears.

- Uses the arrow mark to indicate the direction of the slingshot.

Estimation: 30 seconds

- Adds a button which allows to stop the session during the program. When clicking the button, the session is temporarily stopped and the 4.3.3. Session stop verification pop-up appears (add v1.3)

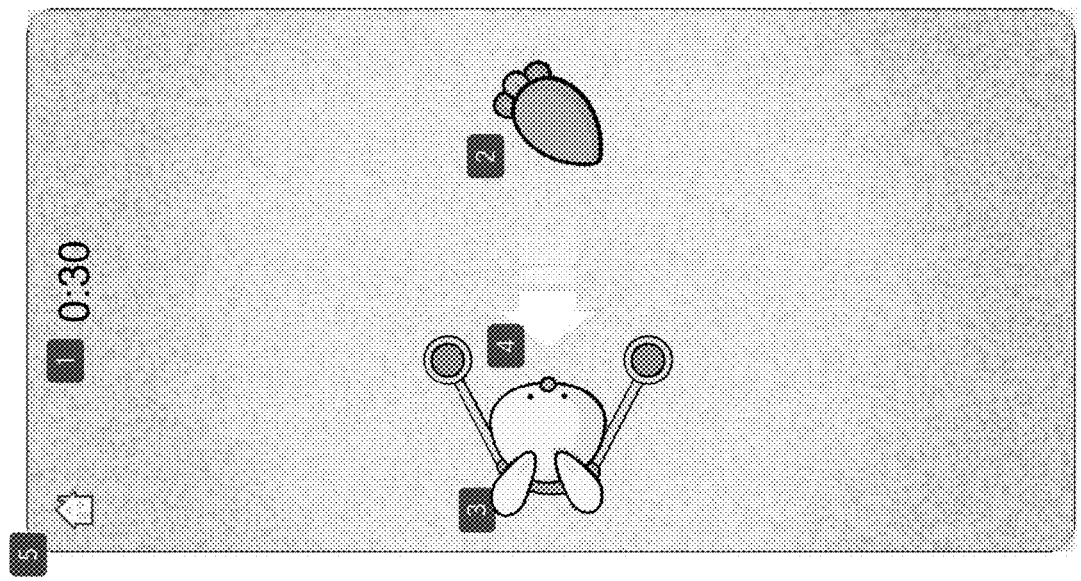

FIG. 32A

■ A cloud character appears
■ The cloud character seems as if it is actually blowing
■ The cloud character moves when it blows (when the user breathes out)

■ The cloud character gets larger and smaller for 105% every 300 ms so that it seems as if it is lightly floating in the air.

According to the voice guidance,
When the character breathes in ■ it gets larger, ■ the lines get shorter, and ■ the tree stands firmly. (2 seconds)
When the character breathes out ■ it gets smaller, ■ the lies get longer, and ■ the tree leans towards the right side. (2 seconds)

A total of two sets needs to be completed.

Estimation: 30 seconds

Reference video: <u>KIDS MEDITATION – COOLING OUT BREATH</u>

■ Adds a button which allows to stop the session during the program.
When clicking the button, the session is temporarily stopped and the 4.3.3. Session stop verification pop-up appears (add v1.3)

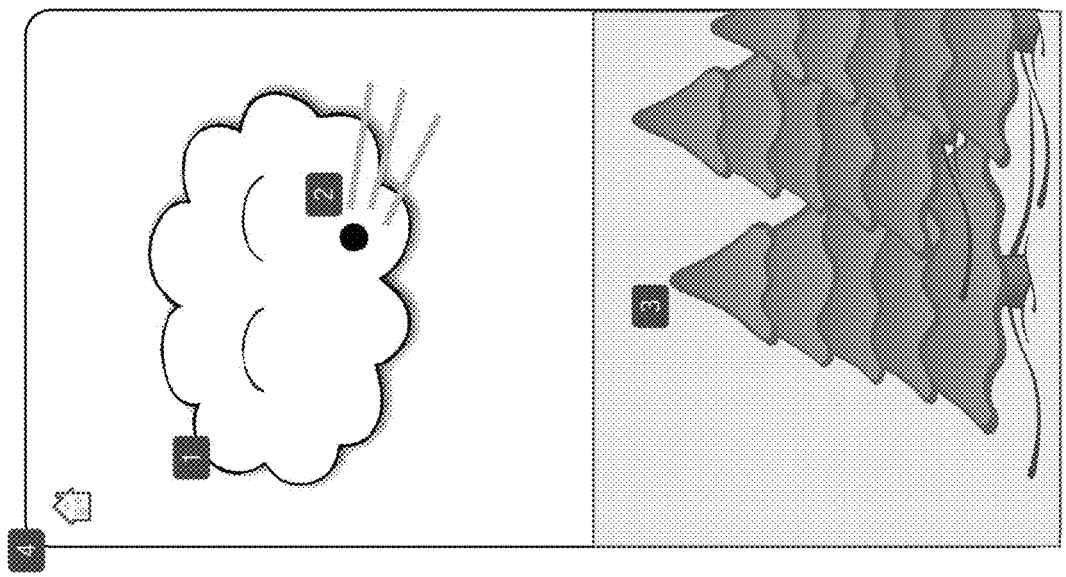

FIG. 33A

- The timer starts at 30 seconds and ends at 0 second.
- Place the windshield and ▓ the wiper in the middle of the screen.
  - Make ▓ the wiper move from side to side as the user's eyes move.
- Spray some water on the windshield so that it seems like raining.
  - Once the rain is dropped on the windshield, the user can wash them away by making the wiper (the eyes) move from right to left and right again.
  - After the droplets are washed out, new droplets are sprayed on the windshield and the user continues to play the game and exercise his/her eyes.

Make a clear difference between the wiped and the non-wiped windshield images to markedly show that the droplets disappear after wiping out. (Refer to the image on the right)

Estimation: 30 seconds

▓ Adds a button which allows to stop the session during the program.
When clicking the button, the session is temporarily stopped and the 4.3.3. Session stop verification pop-up appears (add v1.3)

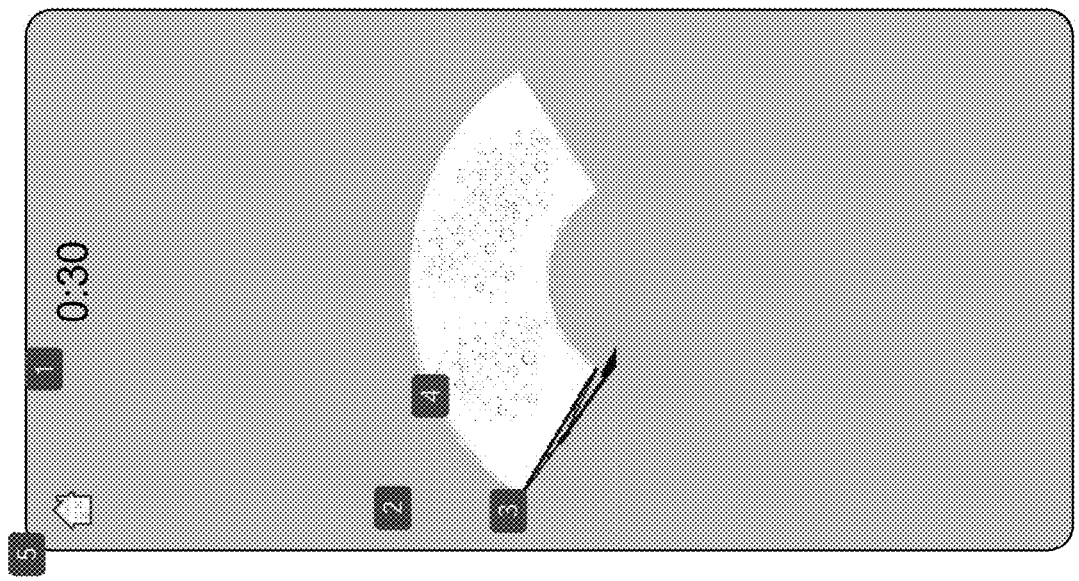

FIG. 34A

- The character appears in the middle of the screen.
- There are about three cloud icons in the sky all of which move towards the right side, each at a slightly different pace.

According to the voice guidance,
- The character blinks its eyes.
- The character stretches its arms.
- The character shakes the arms and hands.

Estimation: 30 seconds

- Adds a button which allows to stop the session during the program. When clicking the button, the session is temporarily stopped and the 4.3.3. Session stop verification pop-up appears (add v1.3)

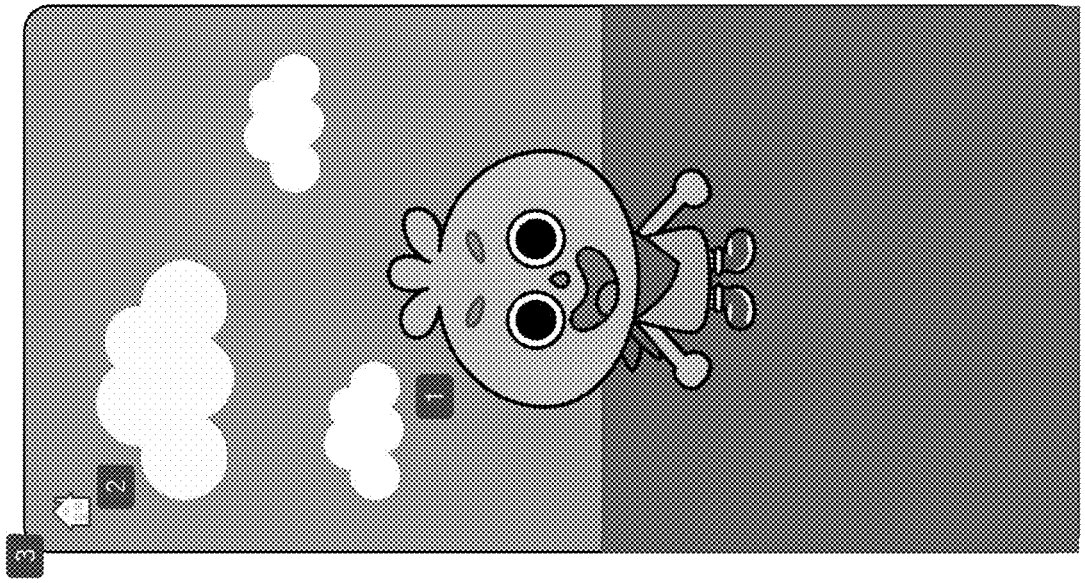

FIG. 35A

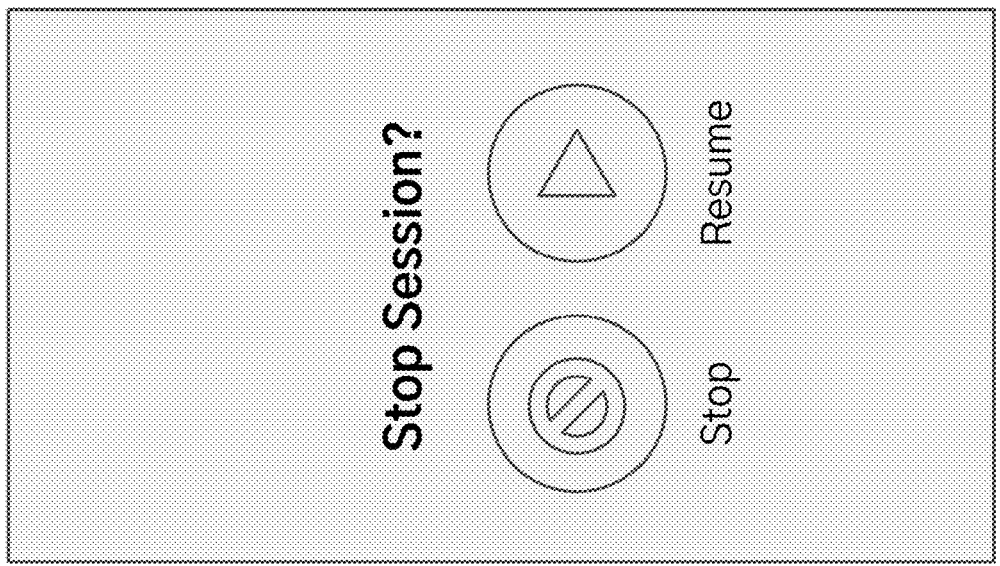
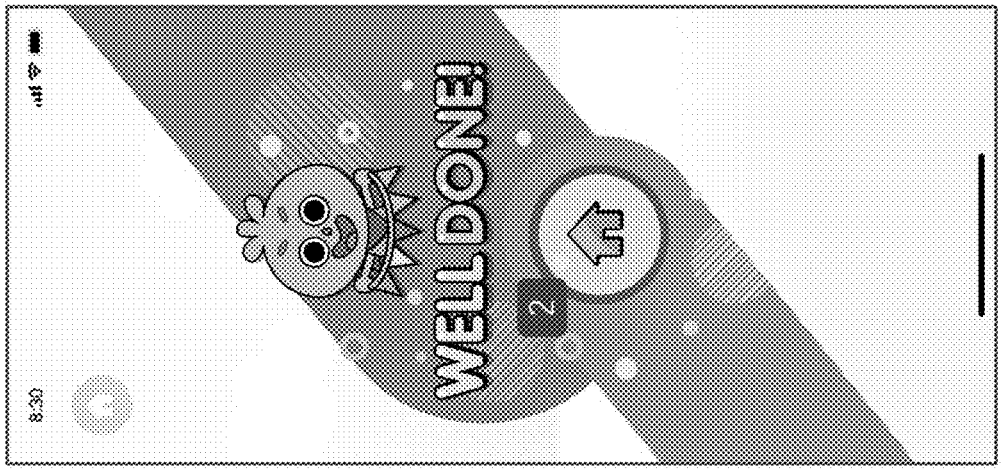
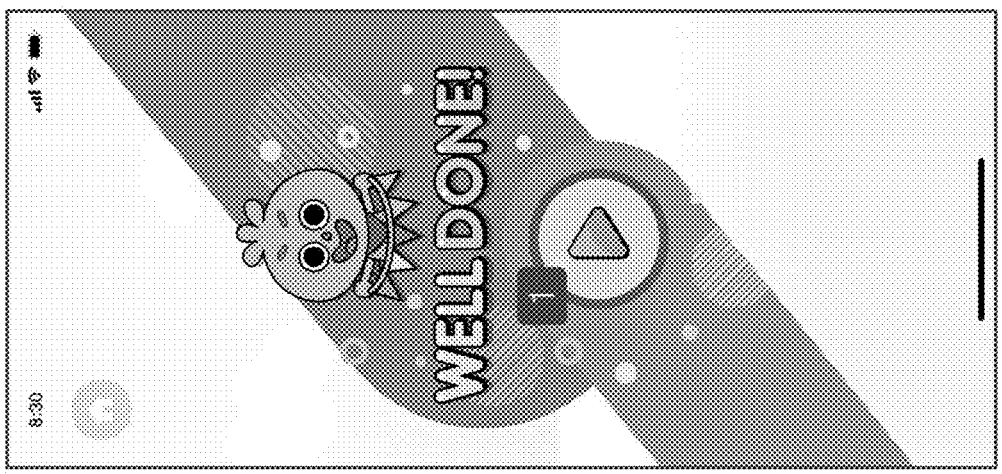
FIG. 36

4.4.1 Room Decoration Board

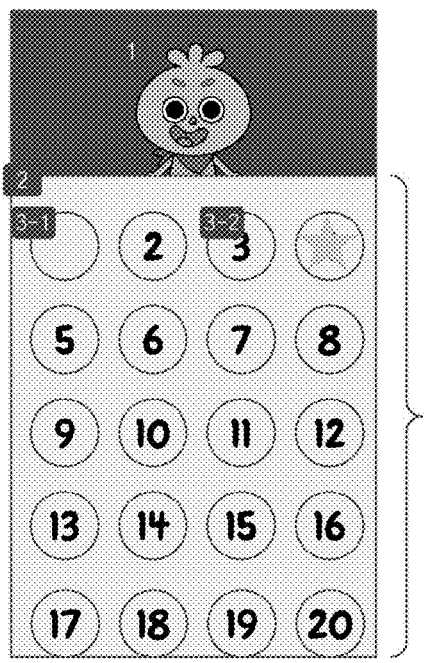

4.4.2 Room Decoration Item Acquirement

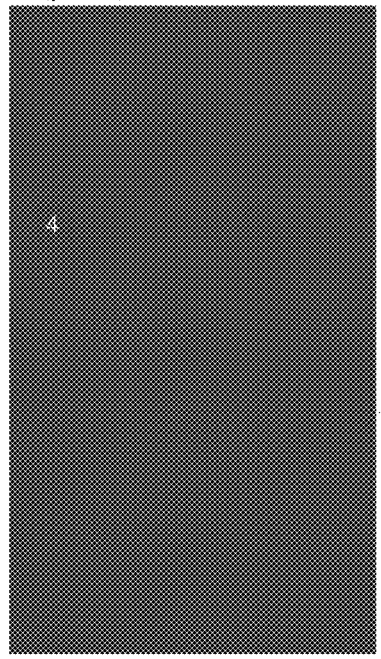

The current date appears on the very top
Can be scrolled down to number 84.

3-1. Moves to 4.4.2 after 3 seconds for room decoration days with items.
3-2. Adds a star mark on the date after a second for room decoration days without items. Moves to home screen two seconds later.

Automatically moves to home screen after 3 seconds
<The item is added in the room of home screen>

FIG. 37A

| Day | Item | Day | Item |
|---|---|---|---|
| day 1 | Bed | day 41 | Table > Items on the table |
| day 4 | Table | day 45 | Sofa |
| day 7 | Carpet | day 49 | Closet > Globe on the close |
| day 10 | Table > Chair | day 53 | TV |
| day 13 | Clock | day 57 | Window > Curtain |
| day 16 | Bed > Bunk bed | day 61 | Dog |
| day 19 | Closet | day 65 | Trash bin |
| day 22 | Toy train | day 69 | Cabinet next to the bed > Fish tank on the cabinet |
| day 25 | Blackboard | day 73 | Slide |
| day 29 | Soccer ball | day 77 | Frame |
| day 33 | Dresser next to the bed | day 81 | Lego |
| day 37 | Window | day 84 | Cat |

FIG. 37B

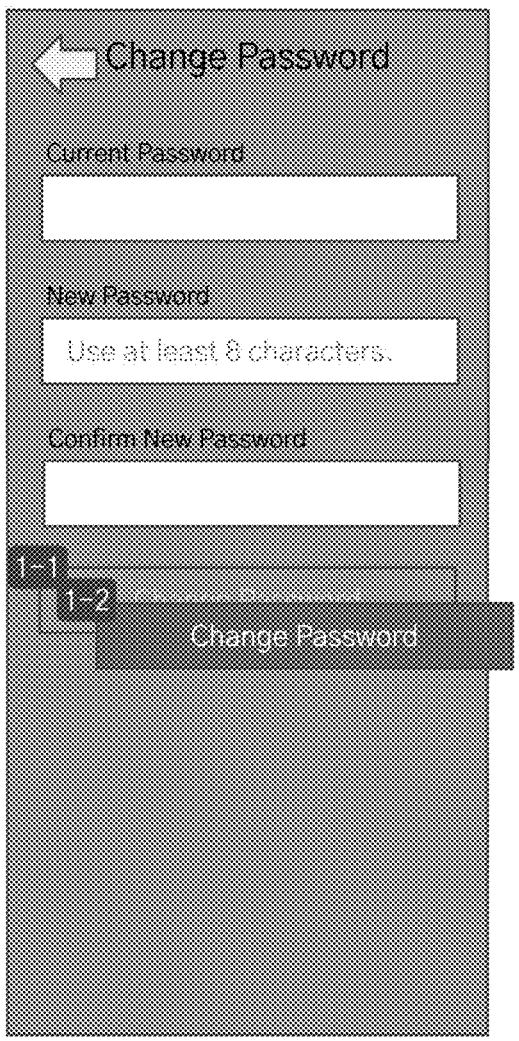

| ID | 3.2.2.1 Wrong password |
|---|---|
| Title | Current password is Wrong. |
| Button | [OK] : close the pop-up |
| ID | 3.2.2.2 Inadequate password |
| Title | Use at least 8 characters. |
| Button | [OK] : close the pop-up |
| ID | 3.2.2.3 Mismatch between new password and confirm new password |
| Title | The passwords you entered do not match. |
| Button | [OK] : close the pop-up |
| ID | 3.2.2.4 Change password |
| Title | The password has changed. |
| Button | [OK] : close the pop-up and move to 3.2.2 Parent Section |

FIG. 39

| Sending | Message | When push opened |
|---|---|---|
| The set time is part of the prescribed duration and the daily session has not been completed | It's time to exercise your eyes! Start eye exercises with your child now! | Enters to home screen after launching the app |
| When there is a paused session / An hour after pausing the session (However, the message is not sent after midnight 12) (add v1.3) | Please resume your eye exercise session! You have to complete the daily session. | Enters to home screen after launching the app |
| When there is a paused session / Three hours after pausing the session (However, the message is not sent after midnight 12) (add v1.3) | Please resume your eye exercise session! You have to complete the daily session. | Enters to home screen after launching the app |
| 1. Suggest Bright Environment | Oops! Why is the room so dirty? Please open the app in a bright environment! | Moves to screen 3.1.4 after launching the app |
| 2. Suggest Bright Environment | Dust and dirt dislikes bright environments! Please open the app in a bright environment! | Moves to screen 3.1.4 after launching the ap |
| 3. Suggest Bright Environment | Why don't you turn on all the lights in your room? Please open the app in a bright environment! | Moves to screen 3.1.4 after launching the ap |

| Doctors | Administrators |
|---|---|
| Login | Login |
| Reset password(click reset button of the email) | Reset password(click reset button of the email) |
| Check dashboard | Check dashboard |
| Check patient list | Check patient list (De-identification) |
| Check a particular patient | Check a particular patient (De-identification) |
| Re-send email/SMS of patient info | – |
| Add patient | – |
| Edit patient info | – |
| Rest patient's password | – |
| Delete patient | – |
| Add prescription | – |
| Check patient's prescription info | Check patient's prescription info (De-identification) |
| Forcibly terminate patient's prescription | – |
| Check patient's session | Check patient's session (De-identification) |
| – | Check doctor list |
| – | Check a particular doctor |
| – | Re-send email of doctor info |
| – | Add doctor |
| – | Edit doctor info |
| – | Deactivate doctor |
| – | Re-activate doctor |

DIGITAL APPARATUS AND APPLICATION FOR TREATING MYOPIA

CROSS-REFERENCE TO RELATED APPLICATION

This application claims under 35 U.S.C. § 19(a) priority to and the benefit of Korean Patent Application No. 10-2019-0130146, filed Oct. 18, 2019, the disclosure of which is incorporated herein by reference in its entirety. This application is related to U.S. application Ser. No. 16/747,980, filed Jan. 21, 2020, which is incorporated herein by reference in its entirety.

FIELD

The present disclosure relates to digital therapeutics (hereinafter referred to as DTx) intended for myopia therapy, which includes inhibition of progression of myopia. The present disclosure also relates to systems that integrate digital therapeutics with one or both of a healthcare provider portal and an administrative portal to treat myopia in a patient. In particular, embodiments of the present disclosure may comprise deducing a mechanism of action (hereinafter referred to as MOA) in axial myopia in childhood/adolescence stages through the literature search and expert reviews of basic scientific articles and related clinical trial articles to find the mechanism of action in myopia, and establishing a therapeutic hypothesis and a digital therapeutic hypothesis for inhibiting progression of axial myopia in the childhood/adolescence stages and treating the axial myopia based on these findings. The present disclosure also relates to a rational design of an application for clinically verifying a digital therapeutic hypothesis for axial myopia in the childhood/adolescence stages and realizing the digital therapeutic hypothesis for digital therapeutics, and to the provision of a digital apparatus and an application for inhibiting progression of axial myopia in childhood/adolescence stages and treating the axial myopia based on this rational design.

BACKGROUND

In Korea, myopic patients have very high morbidity. The results of data analysis in the years 2008 to 2012 show that the morbidity of myopia (−0.75 diopters or higher) in 12- to 18-year-old adolescents in Korea is 80.4%, which is 4.35 times higher than the morbidity of myopia (18.5%) in the 60-year-old elderly in demographic aspects, and that the morbidity in high myopia (−6 diopter or higher) is 12%, which is 8 times higher than that of the 60-year-old elderly (1.5%), and also is three times higher than the morbidity of myopia of the adolescents in U.S.A, the United Kingdom, etc.

It is more serious that approximately 70% of the adolescent myopic patients in Korea were surveyed to be medium- and high-myopic patients. Also, the morbidity of myopia in the elementary school students was approximately 23% in 1980, but steadily increased from 38% in 1990 to 46.2% in 2000.

The World Health Organization (WHO) has recognized myopia as one of diseases, but there is no potent therapeutics against myopia around the world. In recent years, the myopia began again to receive academic attention as the morbidity of myopia has increased suddenly in China, Singapore, Korea, etc. Also, the myopia has emerged as an ophthalmologic disease that may also cause the loss of eyesight in the future.

Types of myopia are divided into axial myopia caused due to the extending axis of eyeball and refractive myopia (i.e., indexmyopia) caused due to an increased refractive index of the eye lens or the cornea, etc. Types of the axial myopia are divided into simple myopia having no influence on the retina or the choroid, and degenerative myopia causing deformation in the retina to induce the loss of eyesight. Except for nuclear sclerosis and keratoconum caused by the diabetes, most of the myopia corresponds to simple axial myopia whose progression is accelerated from the elementary school ages.

As this method for delaying progression of or treating myopia, a method of using a drug (atropine) and a special lens (for example, a dream lens) was known. However, atropine causes serious dazzling with the pupil dilation. Also, because the dream lens has a high risk of damage to the cornea, it has limited clinical applications, compared to glasses for vision corrosion.

Separately, although a variety of apparatuses for treating myopia, eye exercise methods, eye exercise applications, and the like have been developed and sold in the market, most of them have insufficient grounds for the clinical efficacy, and are sold without any additional permission. However, there is no highly reliable therapeutic method that the childhood/adolescent patients who have been diagnosed as myopia in the hospitals can use to inhibit progression of and treat myopia.

SUMMARY OF THE DISCLOSURE

In some aspects, the present disclosure provides a system for treating myopia, comprising a digital apparatus configured to execute a digital application for treating myopia in a subject; a healthcare provider portal configured to provide one or more options to a healthcare provider to perform one or more tasks to prescribe treatment for the myopia in the subject based on information received from the digital application; and an administrative portal configured to provide one or more options to an administrator of the system to perform one or more tasks to manage access to the system by the healthcare provider.

In some aspects, the present disclosure provides a method of treating myopia in a subject in need thereof, the method comprising providing, by a digital apparatus to the subject, a digital application comprising modules for treating myopia based on a mechanism of action in and a therapeutic hypothesis for the myopia, each of the modules comprising one or more first instructions for the subject to follow, wherein the digital apparatus (i) comprises a sensor sensing adherence by the subject to the one or more first instructions of the modules, (ii) transmits adherence information, based on the adherence, to a server accessible by a healthcare provider through a healthcare provider portal, and (iii) receives one or more second instructions from the healthcare provider based on the adherence information.

In some aspects, the present disclosure provides a non-transitory computer readable medium having stored thereon software instructions for treating myopia in a subject in need thereof that, when executed by a processor, cause the processor to display, by an digital apparatus to the subject, modules for treating myopia based on a mechanism of action in and a therapeutic hypothesis for the myopia, each of the modules comprising one or more instructions for the subject to follow; sense, by a sensor in the digital apparatus, adherence by the subject to the instructions of the modules; transmit, by the digital apparatus, adherence information, based on the adherence, to a server accessible by a healthcare provider through a healthcare provider portal; and receive, from the server, one or more second instructions from the healthcare provider.

In some embodiments, the digital application for treating myopia instructs a processor of the digital apparatus to execute operations comprising generating digital therapeutic modules for treating myopia based on a mechanism of action in and a therapeutic hypothesis for the myopia. In some embodiments, the generating of the digital therapeutic modules comprises generating the digital therapeutic modules based on neurohumoral factors related to the myopia onset. In some embodiments, the operations further comprise generating a calibration module for calibrating one or more of an accuracy of measurement of the subject's eye position, and a light environment. In some embodiments, the calibration module is generated prior to generating the digital therapeutic modules. In some embodiments, the accuracy of measurement of the subject's eye position is calibrated, and said calibrating the accuracy of measurement of the subject's eye position comprises one or more of instructing the subject to position their face to appear on a screen of the digital apparatus, detecting the subject's eyes for a given period of time, instructing the subject to blink their eyes, detecting if the subject blinked their eyes, instructing the subject to stare at the screen, instructing the subject to move their eyes in a given direction or rotate their eyes, and determining a threshold for detecting the subject's eyes. In some embodiments, the digital apparatus comprises one or more sensors for tracking movement of the subject's eyeball. In some embodiments, the accuracy of measurement of the light environment is calibrated, and said calibrating the light environment comprises one or more of detecting light in the subject's environment using a light sensor of the digital apparatus, and instructing the subject to turn on one or more lights in their environment. In some embodiments, the digital application for treating myopia instructs a processor of the digital apparatus to execute operations comprising generating digital therapeutic modules for treating myopia based on a mechanism of action in and a therapeutic hypothesis for the myopia. In some embodiments, the digital application for treating myopia instructs a processor of the digital apparatus to execute operations comprising generating digital instructions based on the digital therapeutic modules. In some embodiments, the digital application for treating myopia instructs a processor of the digital apparatus to execute operations comprising providing the digital instruction to a subject. In some embodiments, the digital application for treating myopia instructs a processor of the digital apparatus to execute operations comprising collecting the subject's execution outcomes of the digital instructions. In some embodiments, the generating of the digital instructions and the collecting of the subject's execution outcomes of the digital instructions are repeatedly executed several with multiple feedback loops, and the generating of the digital instructions comprises generating the subject's digital instructions for this cycle based on the subject's digital instructions in the previous cycle and the collected execution outcome data on the subject's digital instructions provided in the previous cycle. In some embodiments, the collecting the subject's execution outcomes of the digital instructions comprises determining one or both of an exercise intensity (EI) and an average exercise intensity (AEI). In some embodiments, AEI is determined as an averaged sum of differences between a final location of an eyeball of the subject and a starting location of the eyeball measured at a given interval. In some embodiments, the interval is between about 10 milliseconds (ms) and about 500 ms. In some embodiments, the EI is determined according the formula $$EI = \frac{AEI \times 100}{145}$$

In some embodiments, the AEI is determined as a sum of static AEI and dynamic AEI. In some embodiments, the generating of the digital therapeutic modules comprises generating the digital therapeutic modules by applying imaginary parameters about the subject's environments, behaviors, emotions, and cognition to the mechanism of action in and the therapeutic hypothesis for the myopia. In some embodiments, the digital application for treating myopia instructs a processor of the digital apparatus to generate digital therapeutic modules comprising two or more modules selected from the group consisting of an eye exercise module, a relaxation module, and a light therapy module. In some embodiments, the eye exercise module comprises one or more exercise instructions for one or more of: eyeball exercise instructions, biofeedback control instructions, and eyeball-related behavior control instructions. In some embodiments, the relaxation module comprises one or more relaxation instructions for one or more of: physical exercise instructions, ego enhancement instructions, safety feeling instructions, comfort feeling instructions, and fun instructions. In some embodiments, the light therapy module comprises one or more light therapy instructions for controlling a light environment of the subject. In some embodiments, the one or more relaxation instructions comprise one or more of playing a sound or song, inducing blinking, and instructing the subject to perform gymnastics. In some embodiments, the digital therapeutic modules further comprise an accomplishment module comprising one or more accomplishment instructions for task accomplishment and for providing compensation for the subject's adherence to the instructions of the two or more first modules. In some embodiments, the digital therapeutic modules further comprise a fun module comprising one or more fun instructions for music, games, or videos. In some embodiments, the one or more options provided to the healthcare provider are selected from the group consisting of adding or removing the subject, viewing or editing personal information for the subject, viewing adherence information for the subject, viewing a result of the subject for one or more at least partially completed digital therapeutic modules, prescribing one or more digital therapeutic modules to the subject, altering a prescription for one or more digital therapeutic modules, and communicating with the subject. In some embodiments, the one or more options comprise the viewing or editing personal information for the subject, and the personal information comprises one or more selected from the group consisting of an identification number for the subject, a name of the subject, a date of birth of the subject, an email of the subject, an email of the guardian of the subject, a contact phone number for the subject, a prescription for the subject, and one or more notes made by the healthcare provider about the subject. In some embodiments, the personal information comprises the prescription for the subject, and the prescription for the subject comprises one or more selected from the group consisting of a prescription identification number, a prescription type, a start date, a duration, a completion date, a number of scheduled or prescribed digital therapeutic modules to be performed by the subject, and a number of scheduled or prescribed digital therapeutic modules to be performed by the subject per day. In some embodiments, the one or more options comprise the viewing the adherence information, and the adherence information of the subject comprises one or more of a number of scheduled or prescribed digital therapeutic modules completed by the subject, and a calendar identifying one or more days on which the subject completed, partially completed, or did not complete one or more scheduled or prescribed digital therapeutic modules. In some embodiments, the one or more options comprise the viewing the result of the subject, and the result of the subject for one or more at least partially completed digital therapeutic modules comprises one or more selected from the group consisting of a time at which the subject started a scheduled or prescribed digital therapeutic module, a time at which the subject ended a scheduled or prescribed digital therapeutic module, an indicator of whether the scheduled or prescribed digital therapeutic module was fully or partially completed, and an exercise intensity (EI). In some embodiments, the one or more options provided to the administrator of the system are selected from the group consisting of adding or removing the healthcare provider, viewing or editing personal information for the healthcare provider, viewing or editing de-identified information of the subject, viewing adherence information for the subject, viewing a result of the subject for one or more at least partially completed digital therapeutic modules, and communicating with the healthcare provider. In some embodiments, the one or more options comprise the viewing or editing the personal information, and the personal information of the healthcare provider comprises one or more selected from the group consisting of an identification number for the healthcare provider, a name of the healthcare provider, an email of the healthcare provider, and a contact phone number for the healthcare provider. In some embodiments, the one or more options comprise the viewing or editing the de-identified information of the subject, and the de-identified information of the subject comprises one or more selected from the group consisting of an identification number for the subject, and the healthcare provider for the subject. In some embodiments, the one or more options comprise the viewing the adherence information for the subject, and the adherence information of the subject comprises one or more of a number of scheduled or prescribed digital therapeutic modules completed by the subject, and a calendar identifying one or more days on which the subject completed, partially completed, or did not complete one or more scheduled or prescribed digital therapeutic modules. In some embodiments, the one or more options comprise the viewing the result of the subject, and the result of the subject for one or more at least partially completed digital therapeutic modules comprises one or more selected from the group consisting of a time at which the subject started a scheduled or prescribed digital therapeutic module, a time at which the subject ended a scheduled or prescribed digital therapeutic module, an indicator of whether the scheduled or prescribed digital therapeutic module was fully or partially completed, and an exercise intensity (EI). In some embodiments, the digital application further comprises a push alarm for one or more of reminding the subject complete a digital therapeutic module and adjusting the light settings of the subject's environment. In some embodiments, the push alarm is activated to remind the subject to adjust the light settings such that the subject is exposed to sufficiently bright light at least 3 times per day. In some embodiments, the subject is a child. In some embodiments, the subject is less than about 20 years old, less than about 15 years old, less than about 10 years old, or less than about 5 years old. In some embodiments, the subject is assisted or supervised by an adult. In some embodiments, the digital apparatus comprises a digital instruction generation unit configured to generate digital therapeutic modules for treating myopia based on a mechanism of action (MOA) in and a therapeutic hypothesis for the myopia, generate digital instructions based on the digital therapeutic modules, and provide the digital instructions to the subject. In some embodiments, the digital apparatus comprises an outcome collection unit configured to collect the subject's execution outcomes of the digital instructions. In some embodiments, the digital instruction generation unit generates the digital therapeutic modules based on neurohumoral factors related to the myopia onset. In some embodiments, the neurohumoral factors comprise insulin-like growth factor (IGF), cortisol, and dopamine. In some embodiments, the digital instruction generation unit generates the digital therapeutic modules based on the inputs from the healthcare provider. In some embodiments, the digital instruction generation unit generates the digital therapeutic modules based on information received from the subject. In some embodiments, the information is received from the subject comprises at least one of basal factors, medical information, and digital therapeutics literacy of the subject, the basal factors including the subject's activity, heart rate, sleep, and diet (including nutrition and calories), the medical information including the subject's electronic medical record (EMR), family history, genetic vulnerability, and genetic susceptibility, and the digital therapeutics literacy including the subject's accessibility, and technology adoption to the digital therapeutics and the apparatus. In some embodiments, the digital instruction generation unit generates the digital therapeutic modules matching to imaginary parameters which correspond to the mechanism of action in and the therapeutic hypothesis for the myopia. In some embodiments, the imaginary parameters are deduced in relation to the subject's environment, behaviors, emotions, and cognition. In some embodiments, the outcome collection unit collects the execution outcomes of the digital instructions by monitoring the subject's adherence to the digital instructions or allowing the subject to directly input the subject's adherence to the digital instructions. In some embodiments, the generation of the digital instructions at the digital instruction generation unit and the collection of the subject's execution outcomes of the digital instructions at the outcome collection unit are repeatedly executed several times with multiple feedback loops, and the digital instruction generation unit generates the subject's digital instructions for this cycle based on the subject's digital instructions in the previous cycle and the execution outcome data on the subject's digital instructions in the previous cycle collected at the outcome collection unit.

BRIEF DESCRIPTION OF THE DRAWINGS

The above and other objects, features and advantages of the present disclosure will become more apparent to those of ordinary skill in the art by describing in detail exemplary embodiments thereof with reference to the attached drawings, in which:

FIG. 7A shows execution environment setups according to one embodiment of the present disclosure, and FIGS. 7B to 7G show examples of specific instructions for each module, and methods of collecting output data according to one embodiment of the present disclosure;

FIG. 21 depicts a splash screen of a digital application of the present disclosure, wherein the splash screen comprises a company logo, loading icon, and/or information on the version of the digital application.

FIG. 22 depicts TrueDepth Camera Notification Screens of a digital application of the present disclosure.

FIG. 24 depicts a Bright Environment Requirement Notification screen of a light therapy module of a digital application of the present disclosure, wherein the Bright Environment Requirement Notification screen indicates the amount of light detected by the digital apparatus.

FIG. 25 depicts a Calibration Notification screen of a digital application of the present disclosure, wherein the Calibration Notification screen indicates whether a subject's eye and/or movement of the eye are detectable by the camera.

FIGS. 26A-B depict (A) a screenshot of an eye exercise digital therapeutic module of the present disclosure, and (B) a flow chart illustrating an execution flow for an eye exercise digital therapeutic module.

FIGS. 27A-B depict (A) a screenshot of a rest with relaxation digital therapeutic module of the present disclosure, and (B) a flow chart illustrating an execution flow for a rest with relaxation digital therapeutic module.

FIGS. 28A-B depict (A) a screenshot of an eye exercise digital therapeutic module of the present disclosure, and (B) a flow chart illustrating an execution flow for an eye exercise digital therapeutic module.

FIGS. 29A-B depict (A) a screenshot of a rest with relaxation using sounds digital therapeutic module of the present disclosure, and (B) a flow chart illustrating an execution flow for a rest with relaxation using sounds digital therapeutic module.

FIGS. 30A-B depict (A) a screenshot of an eye exercise digital therapeutic module of the present disclosure, and (B) a flow chart illustrating an execution flow for an eye exercise digital therapeutic module.

FIGS. 31A-B depict (A) a screenshot of a deep breathing digital therapeutic module of the present disclosure, and (B) a flow chart illustrating an execution flow for a deep breathing digital therapeutic module.

FIGS. 32A-B depict (A) a screenshot of an eye exercise digital therapeutic module of the present disclosure, and (B) a flow chart illustrating an execution flow for an eye exercise digital therapeutic module.

FIGS. 33A-C depict (A) a screenshot of a deep breathing digital therapeutic module of the present disclosure, (B) screenshots of a deep breathing digital therapeutic module when instructing the subject to inhale (left) and exhale (right), and (C) a flow chart illustrating an execution flow for a deep breathing digital therapeutic module.

FIGS. 34A-B depict (A) a screenshot of an eye exercise digital therapeutic module of the present disclosure, and (B) a flow chart illustrating an execution flow for an eye exercise digital therapeutic module.

FIGS. 35A-B depict (A) a screenshot of a rest with relaxation digital therapeutic module of the present disclosure, and (B) a flow chart illustrating an execution flow for a rest with relaxation digital therapeutic module.

FIG. 36 depicts screenshots shown at the completion of a single session, at the completion of all daily sessions, and at stop/start verification in a digital application of the present disclosure.

FIGS. 37A-B depict (A) a screenshot of a Room Decoration Board in an accomplishment module in a digital application of the present disclosure, and (B) a timeline showing the days on which a subject may acquire a given Room Decoration item.

FIG. 39 depicts a screenshot of a Change Password Section in a digital application of the present disclosure.

FIG. 40 is a table showing push messages, a time when a given push message is sent to a subject, and an outcome when a given push message is opened.

FIGS. 45A-I depicts (A) a dashboard of a healthcare provider portal, (B) a patient tab in a healthcare provider portal, the patient tab displaying a list of patients, (C) a patient tab in a healthcare provider portal, the patient tab displaying detailed information on a given patient, (D) a patient tab in a healthcare provider portal for adding a new patient, (E) a patient tab in a healthcare provider portal for editing information of an existing patient, (F) a patient tab in a healthcare provider portal that displays detailed prescription information for a given patient, (G-H) a patient tab in a healthcare provider portal for editing prescription information for a given patient, and (I) a patient tab in a healthcare provider portal for viewing details (e.g., date, status, duration, results) of a given session for a given patient.

FIGS. 47A-I depict (A) a dashboard of an administrative portal, (B) a doctor tab in an administrative portal, the doctor tab displaying a list of doctors, (C) a doctor tab in an administrative portal, the doctor tab displaying a list of patients being cared for by a given doctor, with patient-identifying information redacted (*), (D) a doctor tab in an administrative portal for adding a new doctor, (E) a doctor tab in an administrative portal for editing information of an existing doctor, (F) a patient tab in an administrative portal that displays information for one or more patients, wherein sensitive information is redacted, (G) a patient tab in an administrative portal that displays detailed patient or prescription information for a given patient, (H) a patient tab in an administrative portal that displays detailed prescription information for a given patient, and (I) a patient tab in an administrative portal for viewing details (e.g., date, status, duration, results) of a given session for a given patient.

FIG. 48 is a table showing privileges for the doctors using the healthcare provider portal and the administrators using the administrative portal.

Figure 1A:
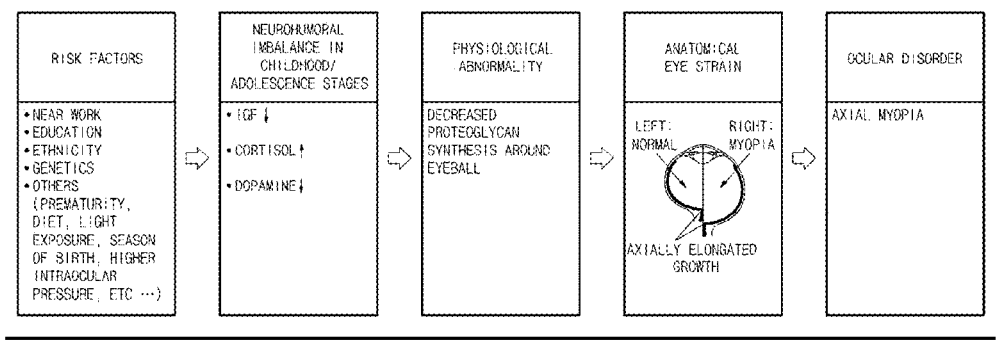
FIG. 1A is a diagram showing a mechanism of action in axial myopia in the childhood/adolescence stages proposed in the present disclosure.

While the above-identified drawings set forth presently disclosed embodiments, other embodiments are also contemplated, as noted in the discussion. This disclosure presents illustrative embodiments by way of representation and not limitation. Numerous other modifications and embodiments may be devised by those skilled in the art which fall within the scope and spirit of the principles of the presently disclosed embodiments.

DETAILED DESCRIPTION

Hereinafter, exemplary embodiments of the present disclosure will be described in detail. However, the present disclosure is not limited to the embodiments disclosed below, but may be implemented in various forms. The following embodiments are described in order to enable those of ordinary skill in the art to embody and practice embodiments of the present disclosure.

Definitions

Although the terms first, second, etc. may be used to describe various elements, these elements are not limited by these terms. These terms are only used to distinguish one element from another. For example, a first element could be termed a second element, and, similarly, a second element could be termed a first element, without departing from the scope of exemplary embodiments. The term "and/or" includes any and all combinations of one or more of the associated listed items.

The terminology used herein is for the purpose of describing particular embodiments only and is not intended to be limiting of exemplary embodiments. The singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, components and/or groups thereof, but do not preclude the presence or addition of one or more other features, integers, steps, operations, elements, components and/or groups thereof.

As used herein, the term "about" generally refers to a particular numeric value that is within an acceptable error range as determined by one of ordinary skill in the art, which will depend in part on how the numeric value is measured or determined, i.e., the limitations of the measurement system. For example, "about" may mean a range of ±20%, ±10%, or ±5% of a given numeric value.

Overview

With reference to the appended drawings, exemplary embodiments of the present disclosure will be described in detail below. To aid in understanding the present disclosure, like numbers refer to like elements throughout the description of the figures, and the description of the same elements will be not reiterated.

In the prior art, the development of new drugs starts with confirming a medial demand in situ, proposing a mechanism of action based on the expert reviews and meta-analysis on the corresponding disease, and deducing a therapeutic hypothesis based on the expert reviews and the meta-analysis. Also, after a library of drugs whose therapeutic effects are expected is prepared based on the therapeutic hypothesis, a candidate material is found through screening, and the corresponding candidate material is subjected to optimization and preclinical trials to check its effectiveness and safety from a preclinical stage, thereby deciding the candidate material as a final candidate drug. To mass-produce the corresponding candidate drug, a CMC (chemistry, manufacturing, and control) process is also established, a clinical trial is carried out on the corresponding candidate drug to verify a mechanism of action and a therapeutic hypothesis of the candidate drug, thereby ensuring the clinical effectiveness and safety of the candidate drug.

From the point of view of this patent, drug targeting and signaling, which fall upstream of the development of new drugs, have many uncertainties. In many cases, because the drug targeting and signaling take a methodology of putting together the outcomes, which have been reported in the art, and interpreting the outcomes, it may be difficult to guarantee the novelty of disclosure. On the contrary, the disclosure of drugs capable of regulating the drug targeting and signaling to treat a disease requires the highest level of creativity except for the field of some antibody or nucleic acid (DNA, RNA) therapeutics in spite of the development of research methodology for research and development of numerous new drugs. As a result, the molecular structures of the drugs are the most critical factors that constitute the most potent substance patent in the field of new drugs.

Unlike the drugs whose rights are strongly protected through this substance patent, digital therapeutics are basically realized using software. Due to the nature of the digital therapeutics, the rational design of digital therapeutics against the corresponding disease, and the software realization of the digital therapeutics based on the rational design may be considered to be a very creative process of disclosure to be protected as a patent when considering the clinical verification and approval processes as the therapeutics.

That is, the core of the digital therapeutics as in the present disclosure depends on the rational design of digital therapeutics suitable for treatment of the corresponding disease, and the development of specific software capable of clinically verifying the digital therapeutics based on the rational design. Hereinafter, a digital apparatus and an application for treating myopia according to the present disclosure realized in this aspect will be described in detail.

Figure 12:
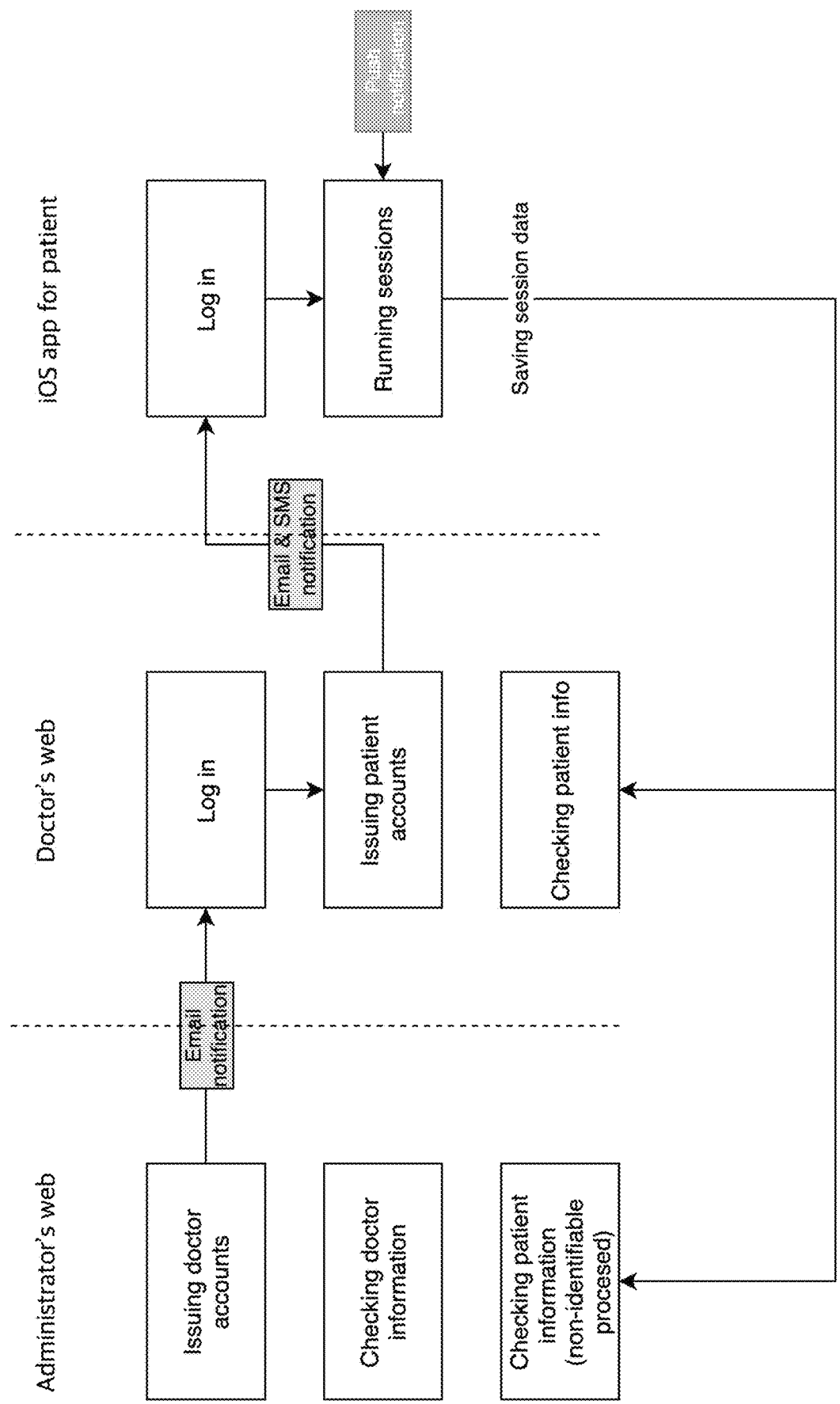
FIG. 12 is a flow chart illustrating a system for treating myopia, the system comprising an administrative portal (e.g., Administrator's web), a healthcare provider portal (e.g., Doctor's web) and a digital apparatus configured to execute a digital application (e.g., an application or 'app') for treating myopia in a subject.
Figure 13:
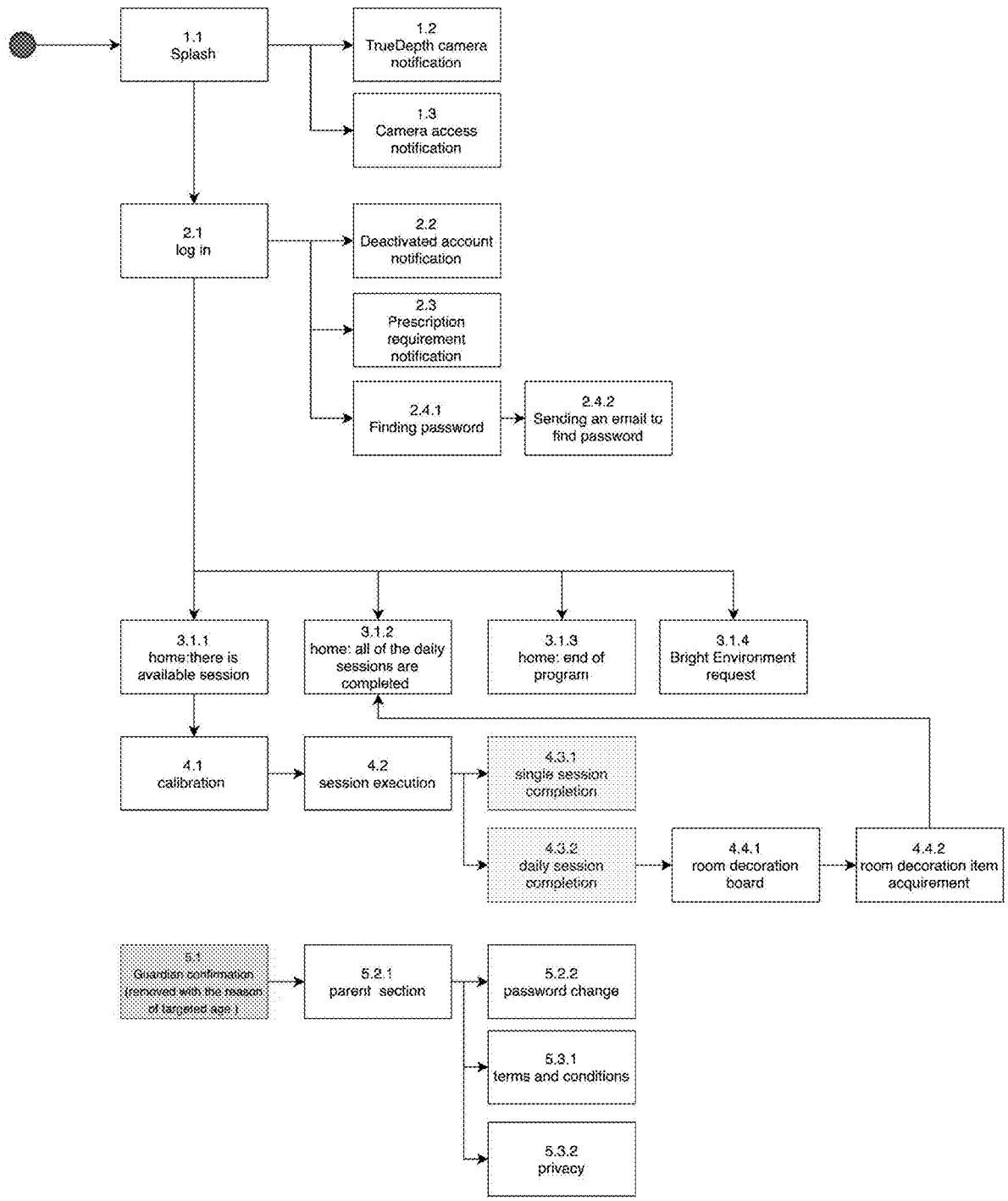
FIG. 13 is a flow chart illustrating an execution flow for a digital application of the present disclosure.
Figure 14:
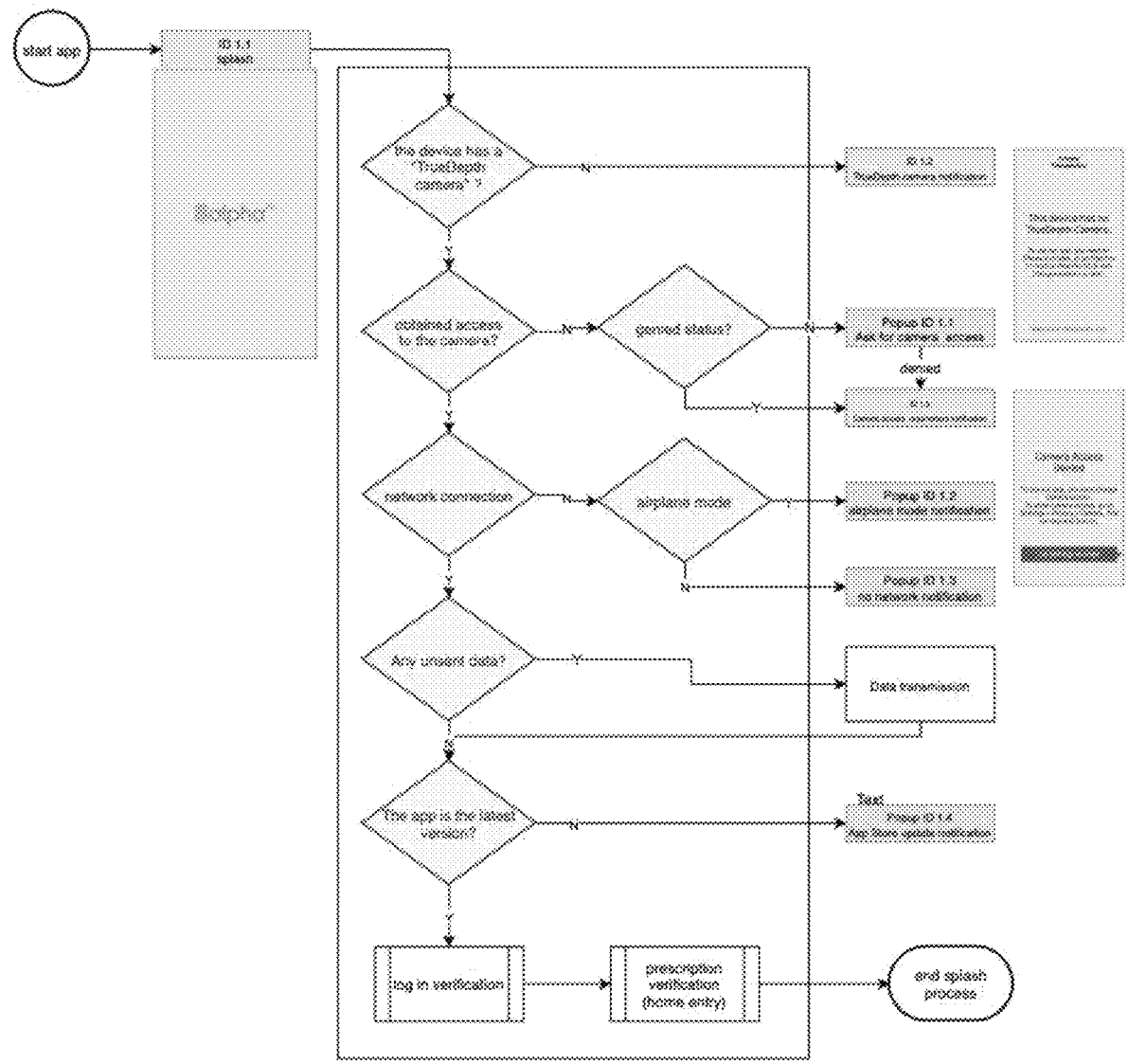
FIG. 14 is a flow chart illustrating an execution flow for a splash process at the starting of a digital application of the present disclosure.
Figure 15:
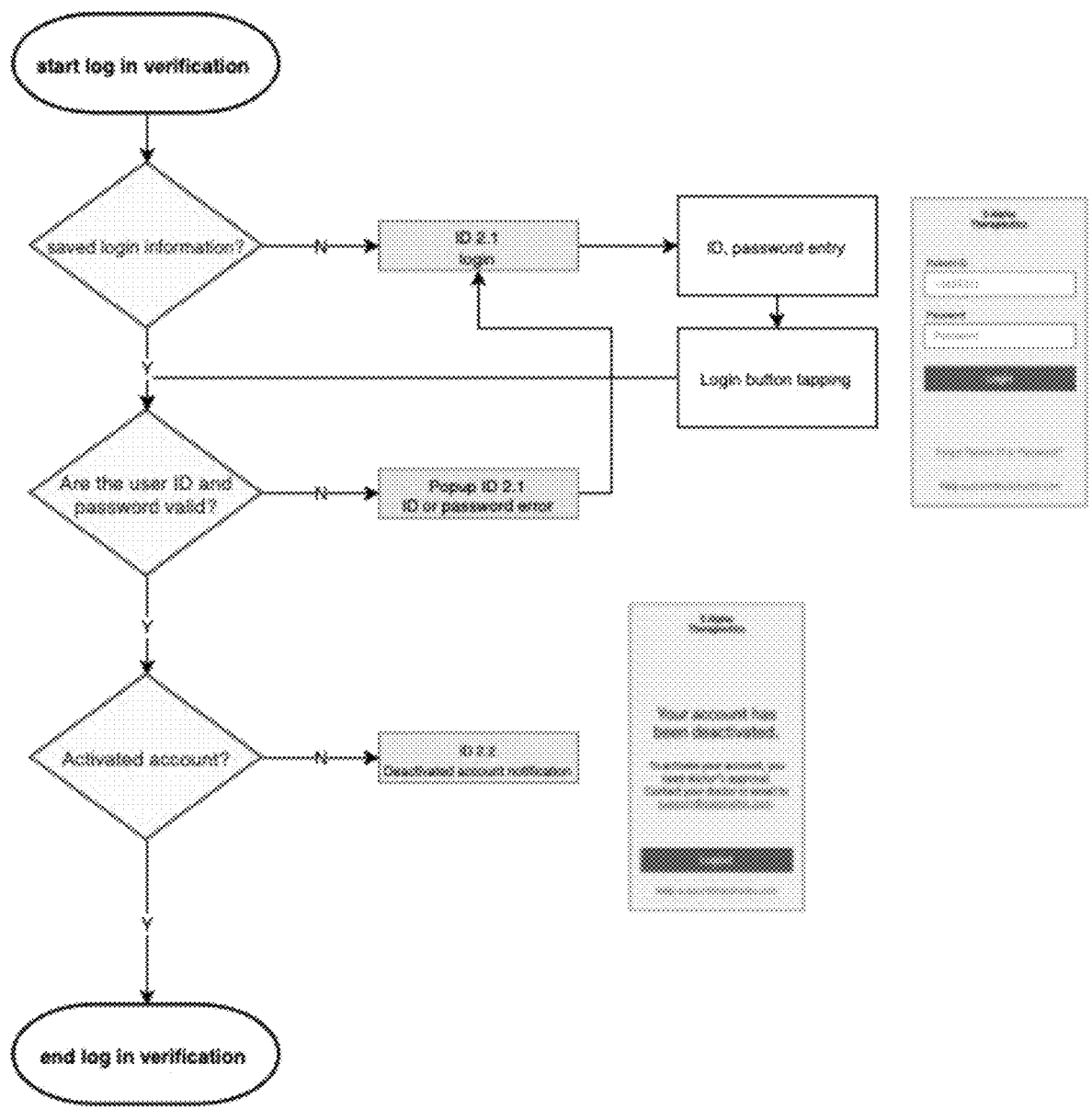
FIG. 15 is a flow chart illustrating an execution flow for a login verification during a splash process at the starting of a digital application of the present disclosure.
Figure 16:
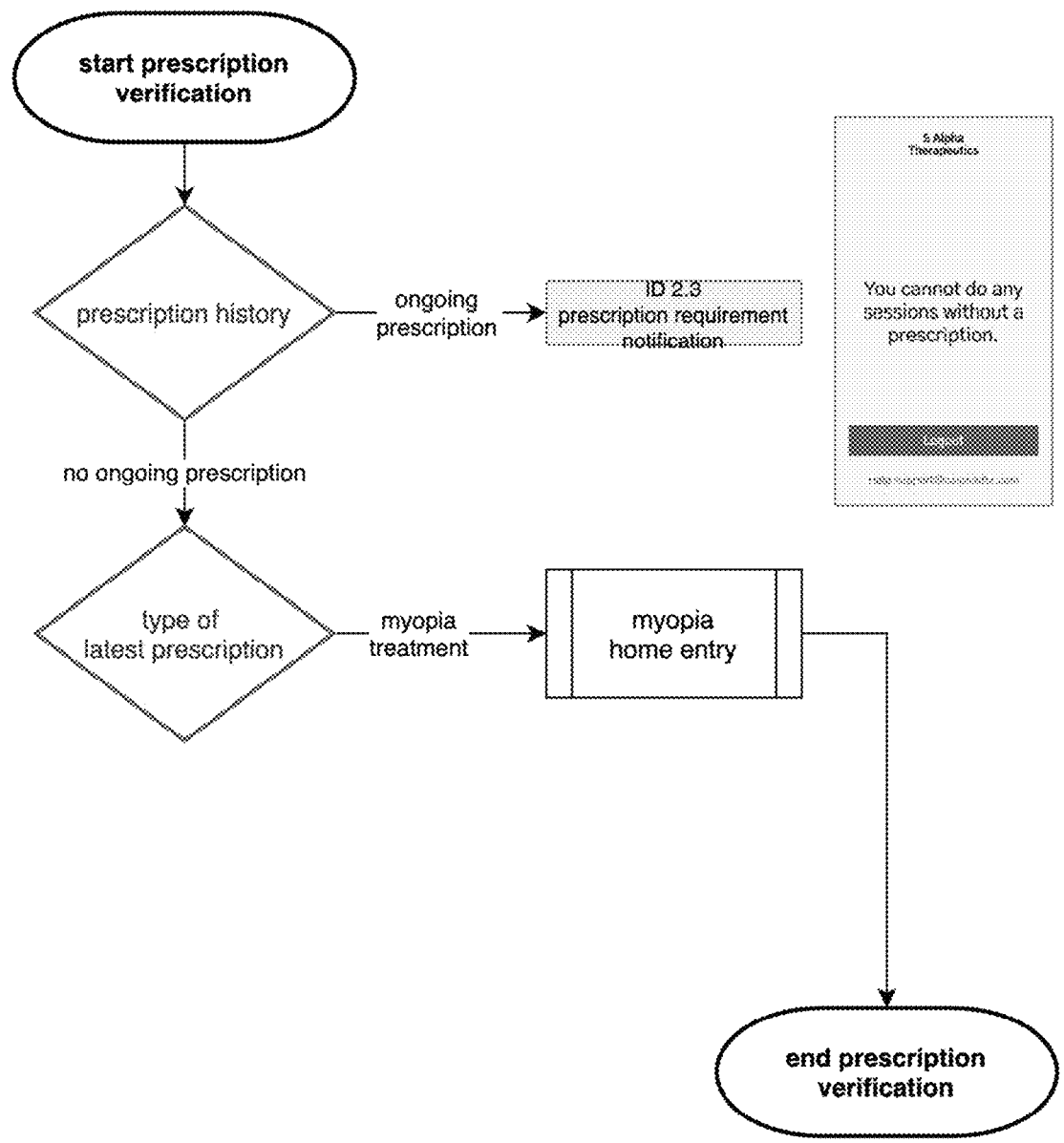
FIG. 16 is a flow chart illustrating an execution flow for a prescription verification during a splash process at the starting of a digital application of the present disclosure.
Figure 17:
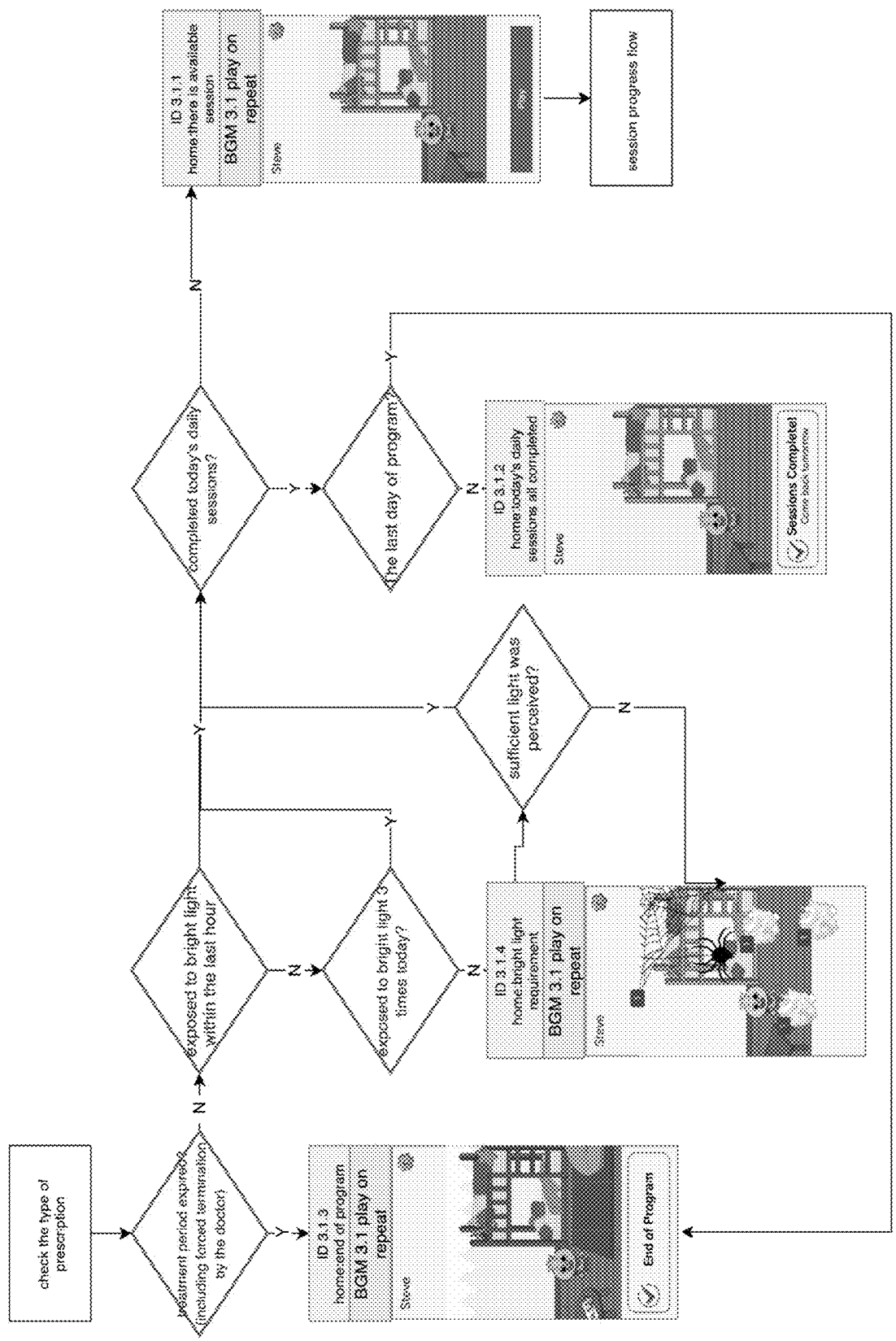
FIG. 17 is a flow chart illustrating an execution flow for home entry during a prescription verification in a digital application of the present disclosure.
Figure 18:
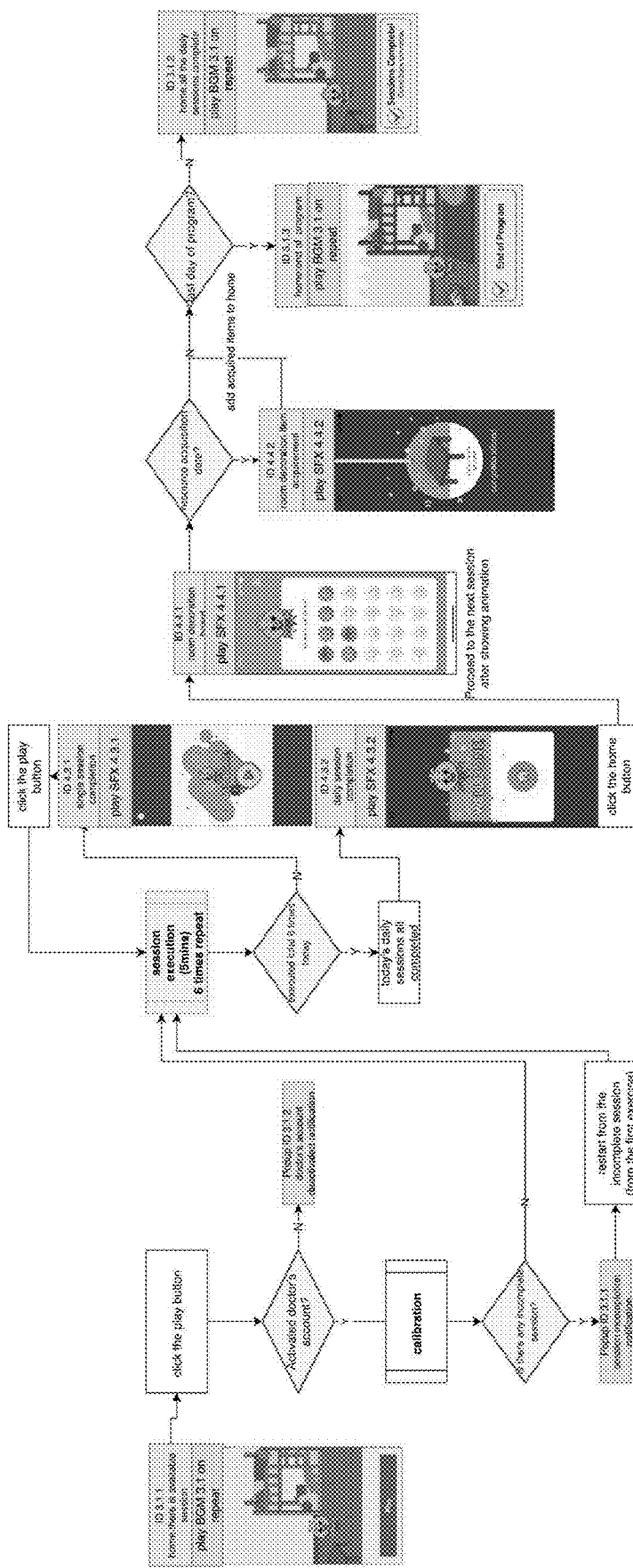
FIG. 18 is a flow chart illustrating an execution flow for sessions in a digital application of the present disclosure.

In certain aspects, the present disclosure provides a system for treating myopia. In some embodiments, the system comprises a digital apparatus configured to execute a digital application for treating myopia in a subject. In some embodiments, the system comprises a healthcare provider portal configured to provide one or more options to a healthcare provider to perform one or more tasks to prescribe treatment for the myopia in the subject based on information received from the digital application. In some embodiments, the system comprises an administrative portal configured to provide one or more options to an administrator of the system to perform one or more tasks to manage access to the system by the healthcare provider. FIG. 12 depicts a flow chart illustrating a system for treating myopia, the system comprising an administrative portal (e.g., Administrator's web), a healthcare provider portal (e.g., Doctor's web) and a digital apparatus configured to execute a digital application (e.g., an application or 'app') for treating myopia in a subject. Among other things, the Administrator's portal allows an administrator to issue doctor accounts, review doctor information, and review de-identified patient information. Among other things, the Healthcare Provider's portal allows a healthcare provider (e.g., a doctor) to issue patient accounts, and review patient information (e.g., age, prescription information, and status for having completed one or more digital therapeutic modules or sessions). Among other things, the digital application allows a patent access to complete one or more digital therapeutic modules or sessions. FIG. 13 depicts a flow chart illustrating an execution flow for the digital application. Upon opening the digital application, a splash screen is displayed, followed by a request for log in information, as well as a verification of prescription information for the subject. FIG. 14 depicts a flow chart illustrating an execution flow for a splash process at the starting of the digital application. The splash process may comprise detecting whether the digital apparatus comprises a TrueDepth camera, detecting whether the digital application has access to the camera, detecting whether the digital application has a network connection, whether the digital application has been updated to the latest version, login verification, and prescription verification. FIG. 15 depicts a flow chart illustrating an execution flow for login verification during a splash process at the starting of the digital application. Similarly, FIG. 16 depicts a flow chart illustrating an execution flow for prescription verification during a splash process at the starting of the digital application. The prescription verification process may comprise, for example, determining if the treatment period has expired, determining whether the subject has been recently (e.g., within the last hour) been exposed to bright light), determining if, based on the prescription, the subject's sessions for the day have been completed (e.g., the subject is compliant with the prescription). In such instances, the digital apparatus may notify the subject that there are no sessions available to be completed, and/or expose the subject to a light therapy module prior to beginning any digital therapeutic modules. FIG. 21 depicts a splash screen of a digital application of the present disclosure, wherein the splash screen comprises a logo (labeled 1), loading icon (labeled 2), and/or information on the version of the digital application (labeled 3). The splash entry process checks the network, version, login verification and others based on the execution flow. If there are data which had not been sent due to forced app termination, network errors, etc., the data are checked and sent during splash entry. During the splash entry process, the loading icon is shown when the process takes too long. In certain embodiments, appropriate pop-ups are shown for different situations of application execution flow. The splash entry process may also include camera detection. FIG. 22 depicts TrueDepth Camera Notification Screens of a digital application of the present disclosure. In devices that do not support TrueDepth Camera, eye exercises cannot be conducted, and thus prevent further application execution from appearing on the screen. The camera (also referred to as a sensor, a depth sensor, or a range sensor) can generate depth data indicating distance to points in a surrounding. In some embodiments, the digital apparatus includes (i) a camera that faces a user (e.g., to obtain facial data about the user's face, such as the location of the eyeball, hand data about the user's hand, or other data about other parts of the user's body) and/or (i) a camera that faces a user's environment (e.g., to obtain location data about the user's physical environment, such as the location of a light). In certain embodiments, the camera comprises a three dimensional camera system, such as the TrueDepth® camera system manufactured by Apple, Inc., Cupertino, Calif. (USA). In another embodiment, the camera comprises a time-of-flight (ToF) camera that measures the time-of-flight of a light signal between the ToF camera and a target in an environment (e.g., the eyeball of the subject). In yet another embodiment, the camera comprises a structured-light 3D scanner (e.g., an infrared emitter and infrared camera) to implement a structured-light technique that projects a known pattern (e.g., structured light) onto a surface and captures image(s). A person of skill in the art will appreciate that the camera can implement other techniques, such as sheet of light triangulation, stereo triangulation, interferometry, and the like. As non-limiting examples, the camera can implement techniques and/or components used by a RealSense® camera from Intel®, a Hololens® from Microsoft®, a TrueDepth® camera from Apple®, a Tango® system from Google®, a Kinect® system from Microsoft®, and the like. In some embodiments, the camera is configured to capture an image. In some embodiments, the camera is configured to generate depth data, such as a range image, depth map, or the like. The depth data may indicate one or more distances to one or more points (e.g., the distance moved by an eyeball over a given interval of time) represented in the depth data, respectively. In some examples, depth data may be used to identify distances to points in an environment, identify an object or surface in the environment, determine distance travelled by an object over a given interval, and/or position and/or maintain a representation of user or other content in relation to the object or the surface as the digital apparatus moves within the environment (e.g., in an AR or VR implementation).

A Mailto link (labeled 1) may be included to help the subject send mail to a support team. Camera access may be allowed/disallowed (e.g., turned on/off) by the user whenever he/she wants. Camera access status is checked every time the app launches, and if the access is disallowed (off), a screen indicating that camera access is denied is displayed and the application is prevented from further execution. A button (labeled 2) may also be displayed to assist the subject in jumping to the settings panel of the digital apparatus to adjust the settings (e.g., allow camera access).

Figure 23:
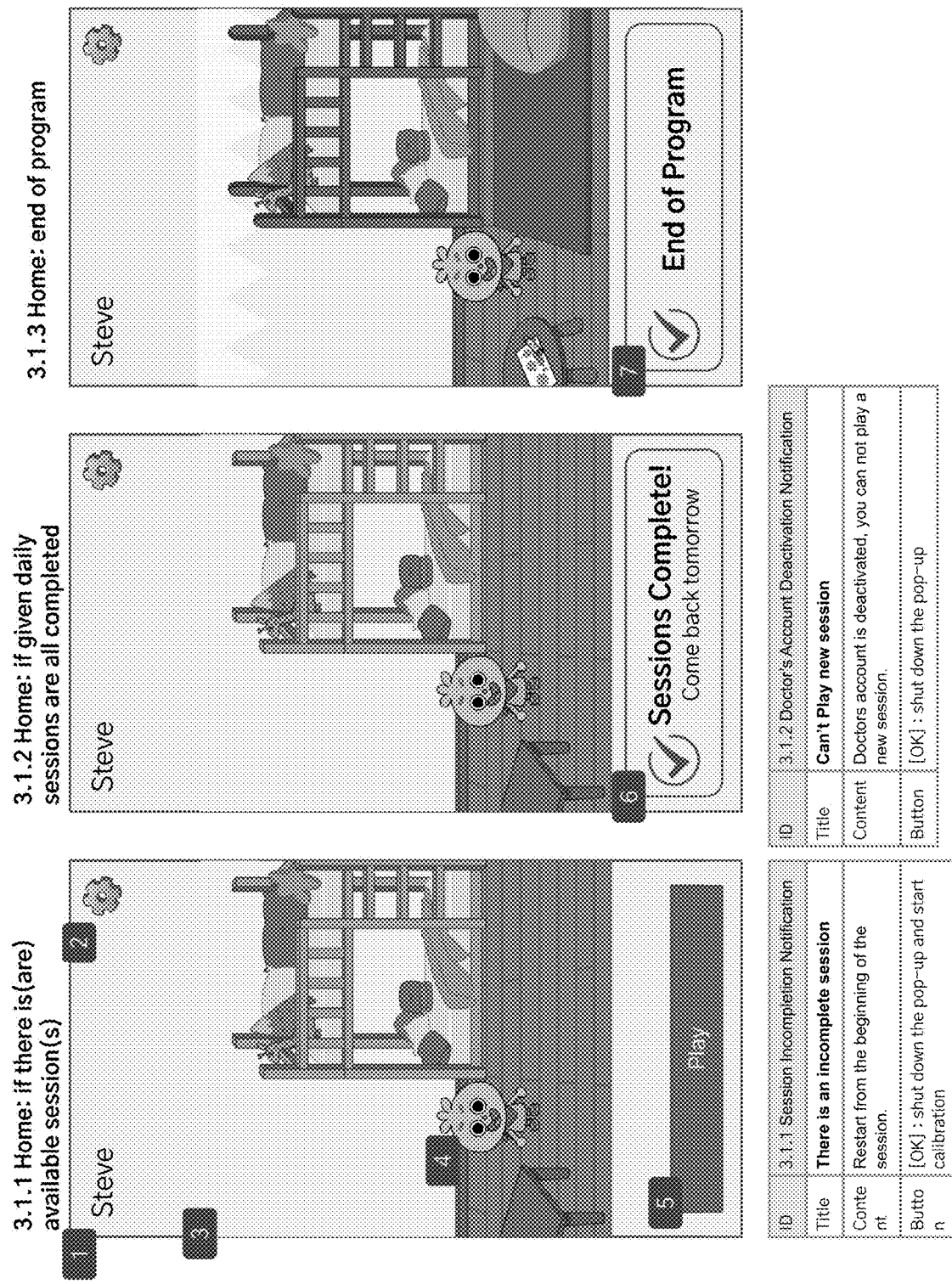
FIG. 23 depicts Home screens of a digital application of the present disclosure, wherein the Home screen indicates the availability of sessions for a subject to complete.
Figure 26B:
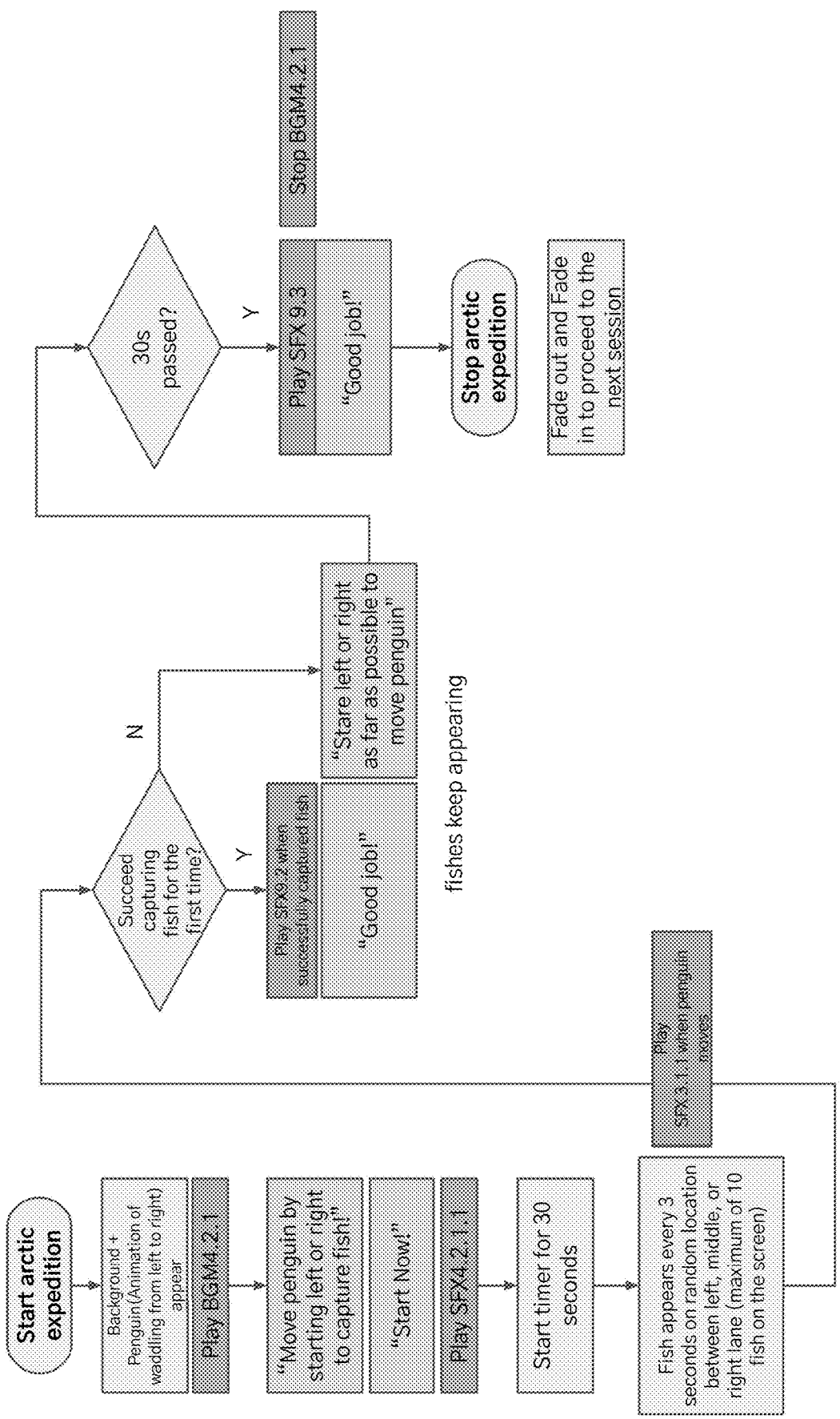
Figure 27B:
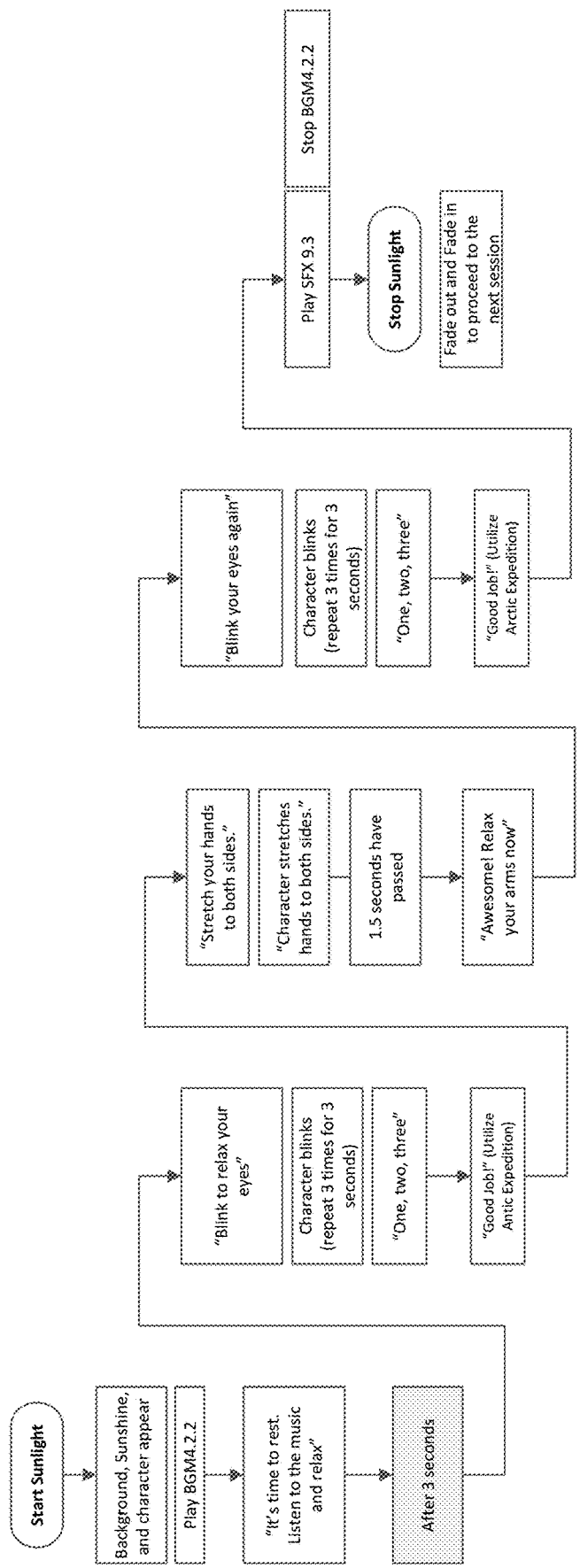
Figure 28B:
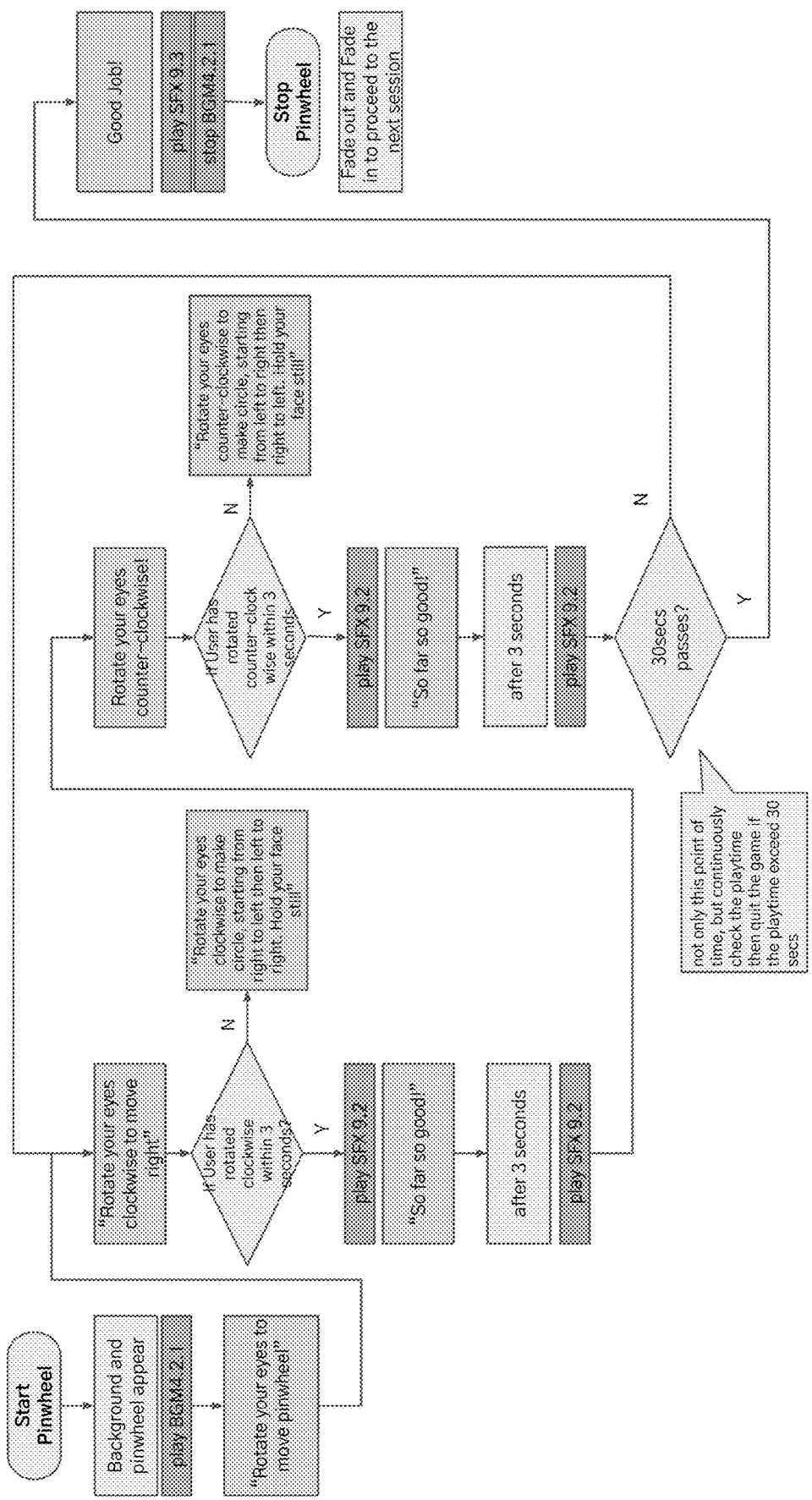
Figure 29B:
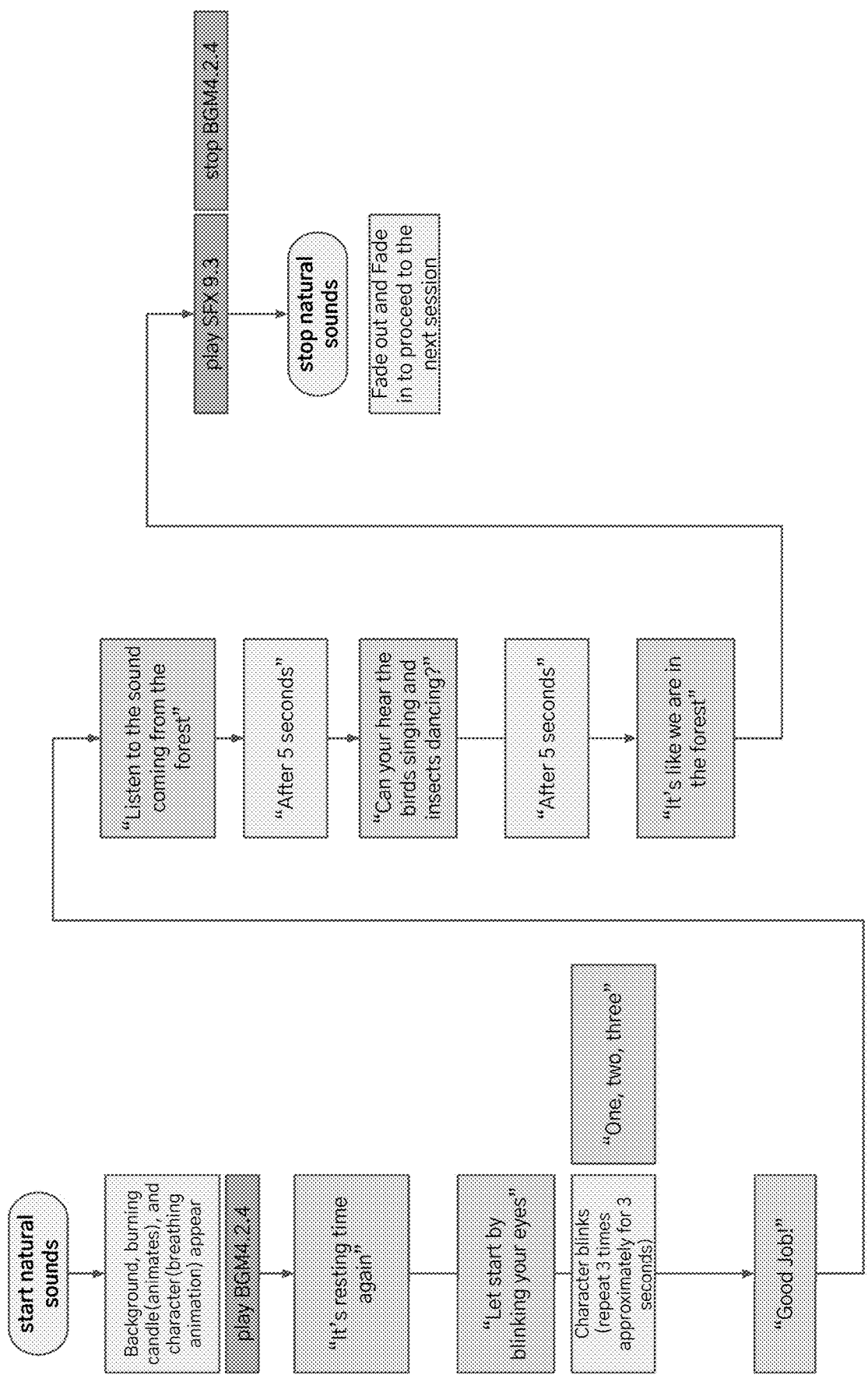
Figure 30B:
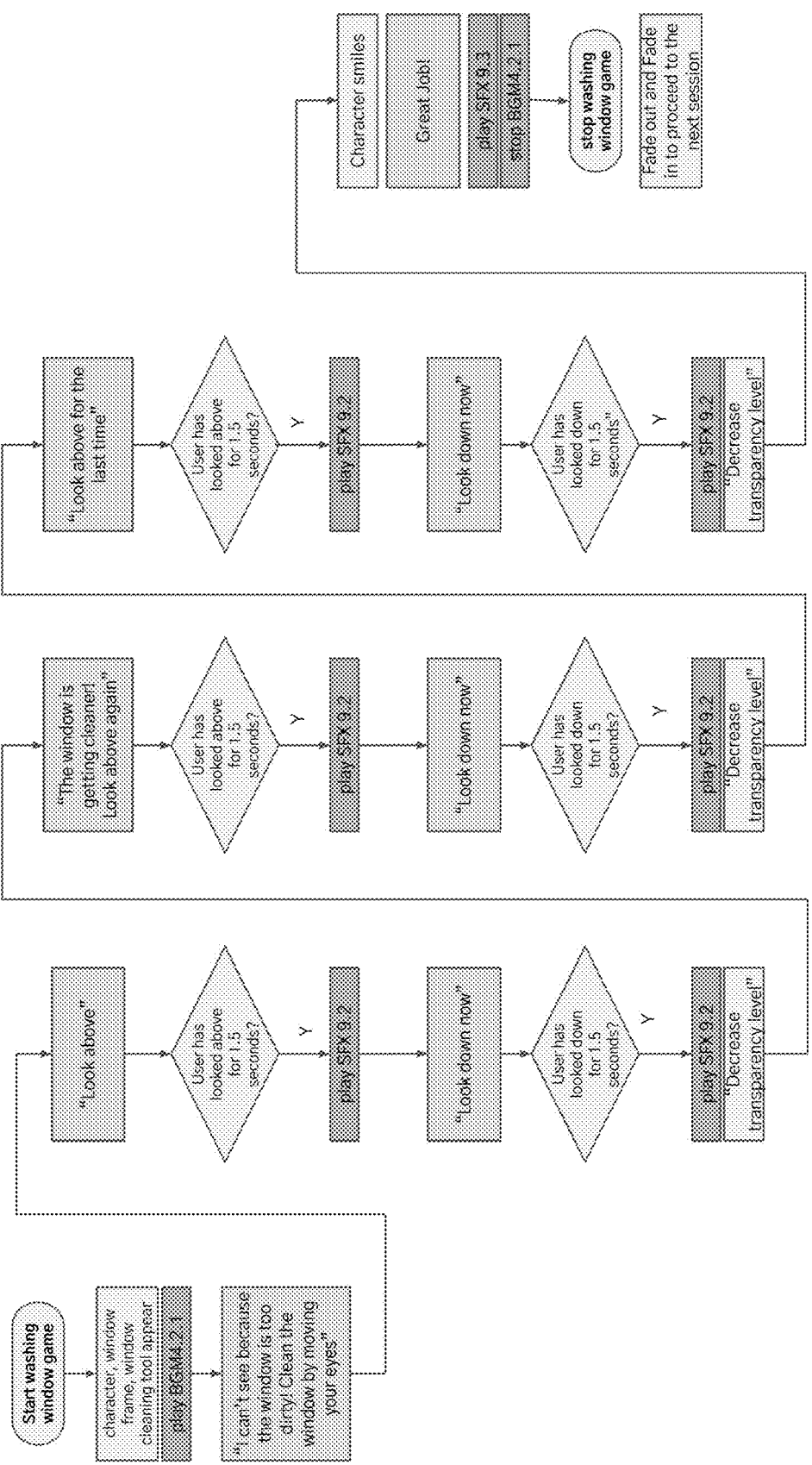
Figure 31B:
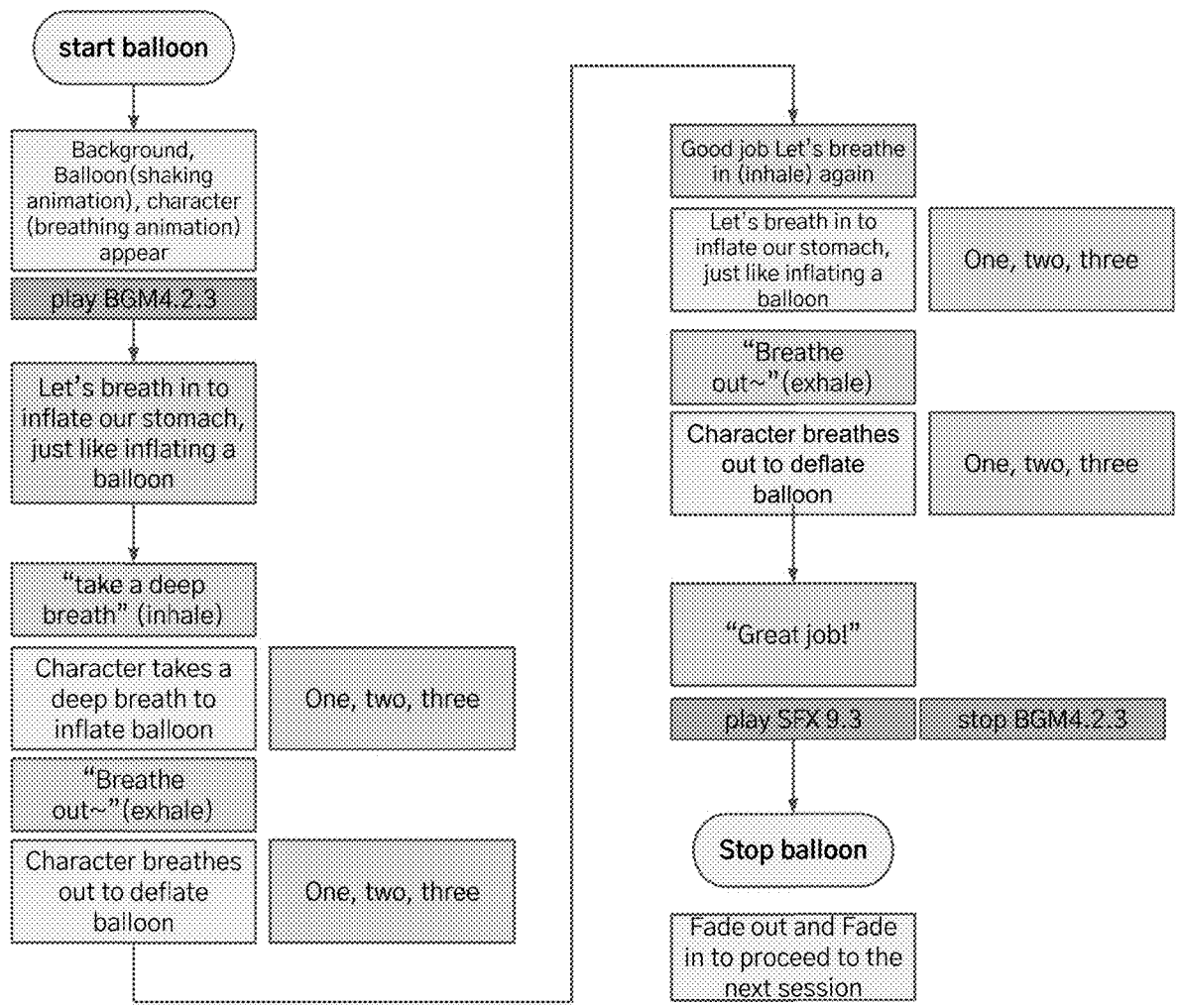
Figure 32B:
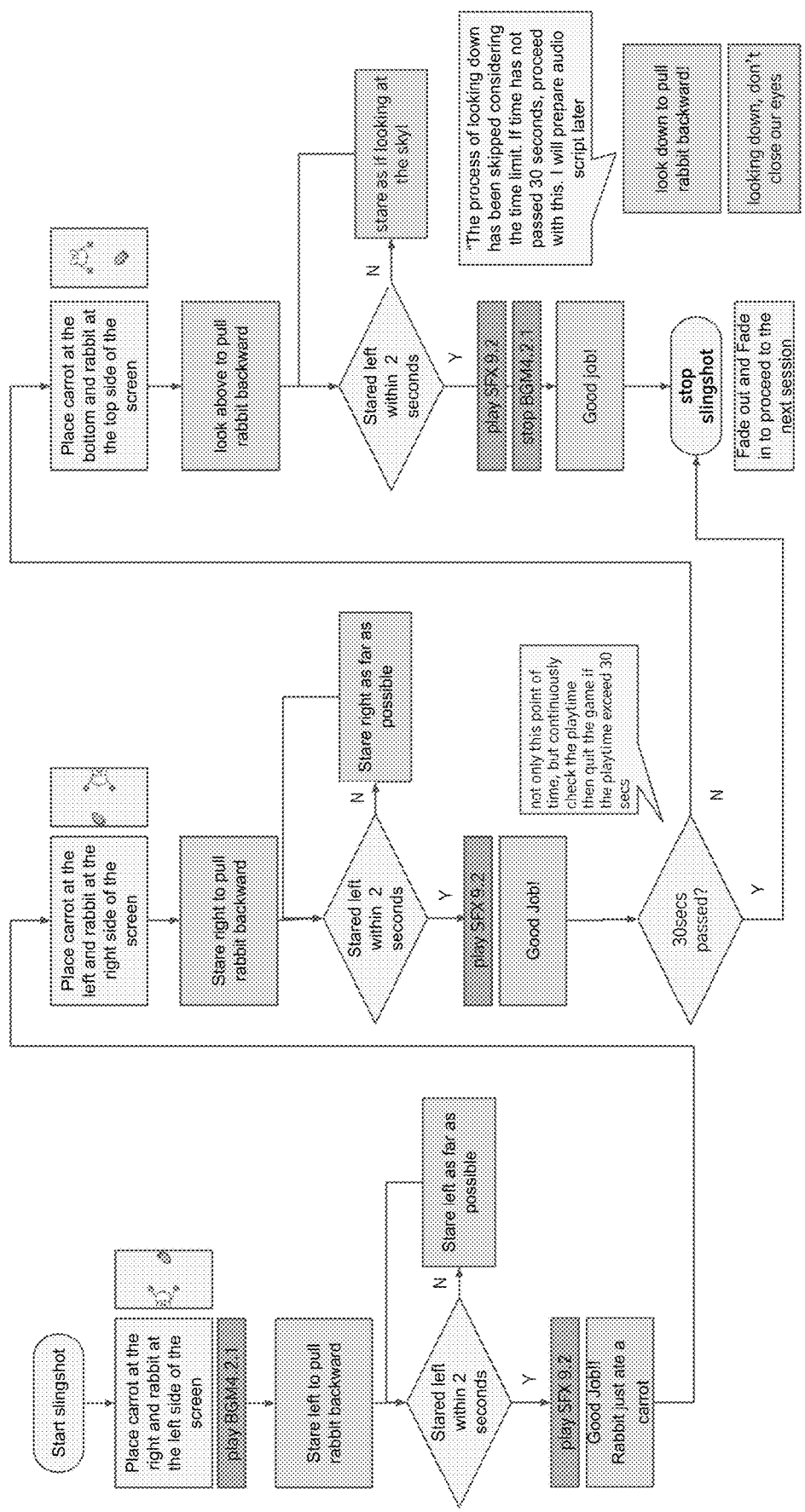
Figure 33B:
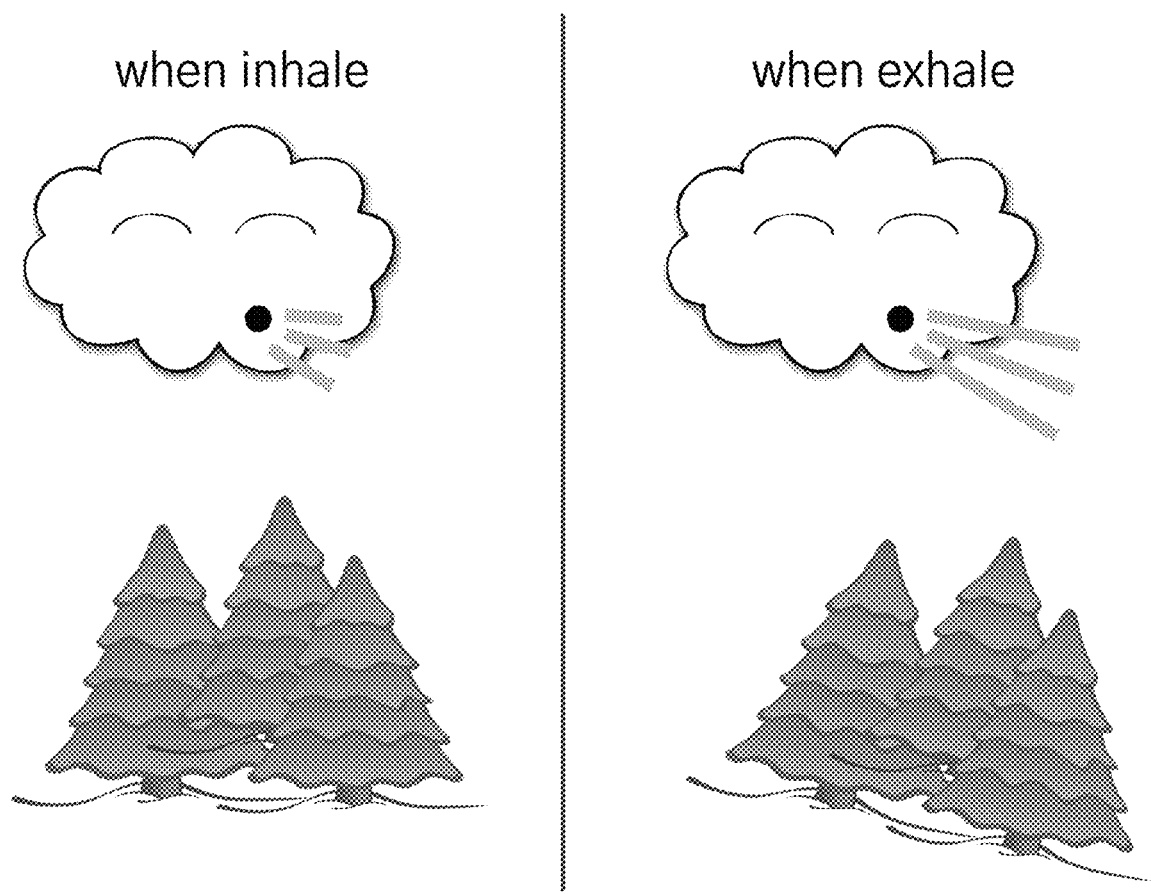
Figure 33C:
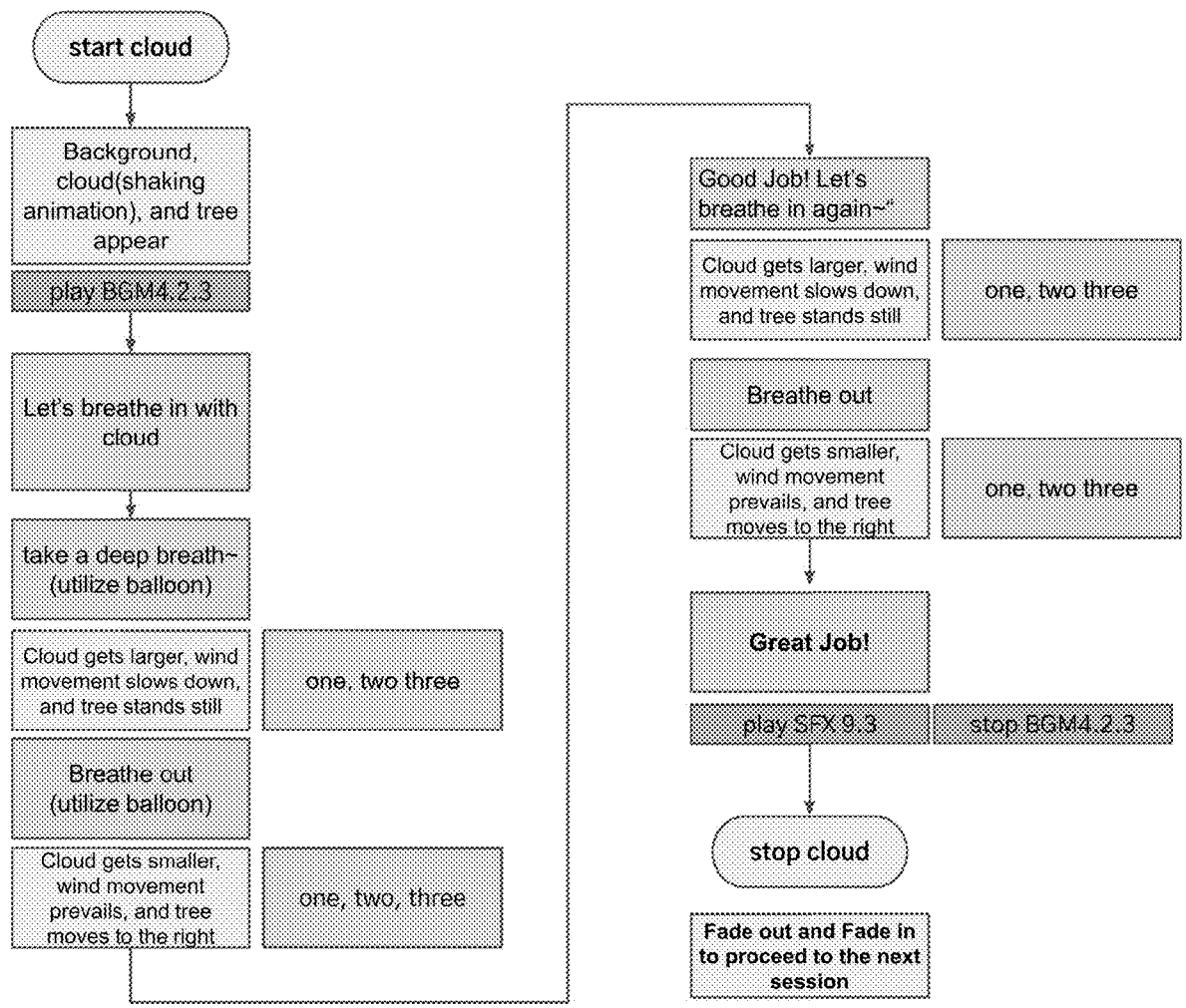
Figure 34B:
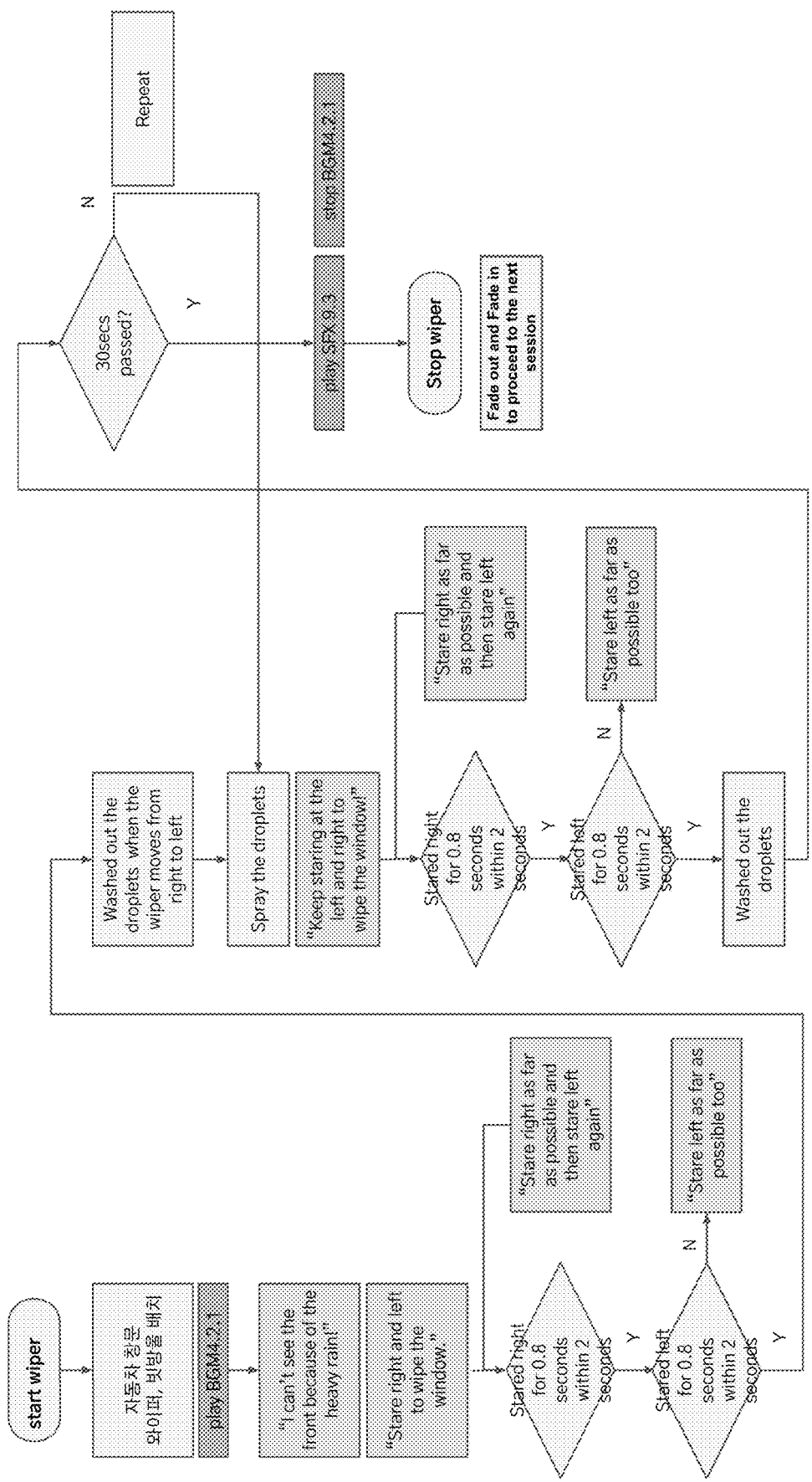
Figure 35B:
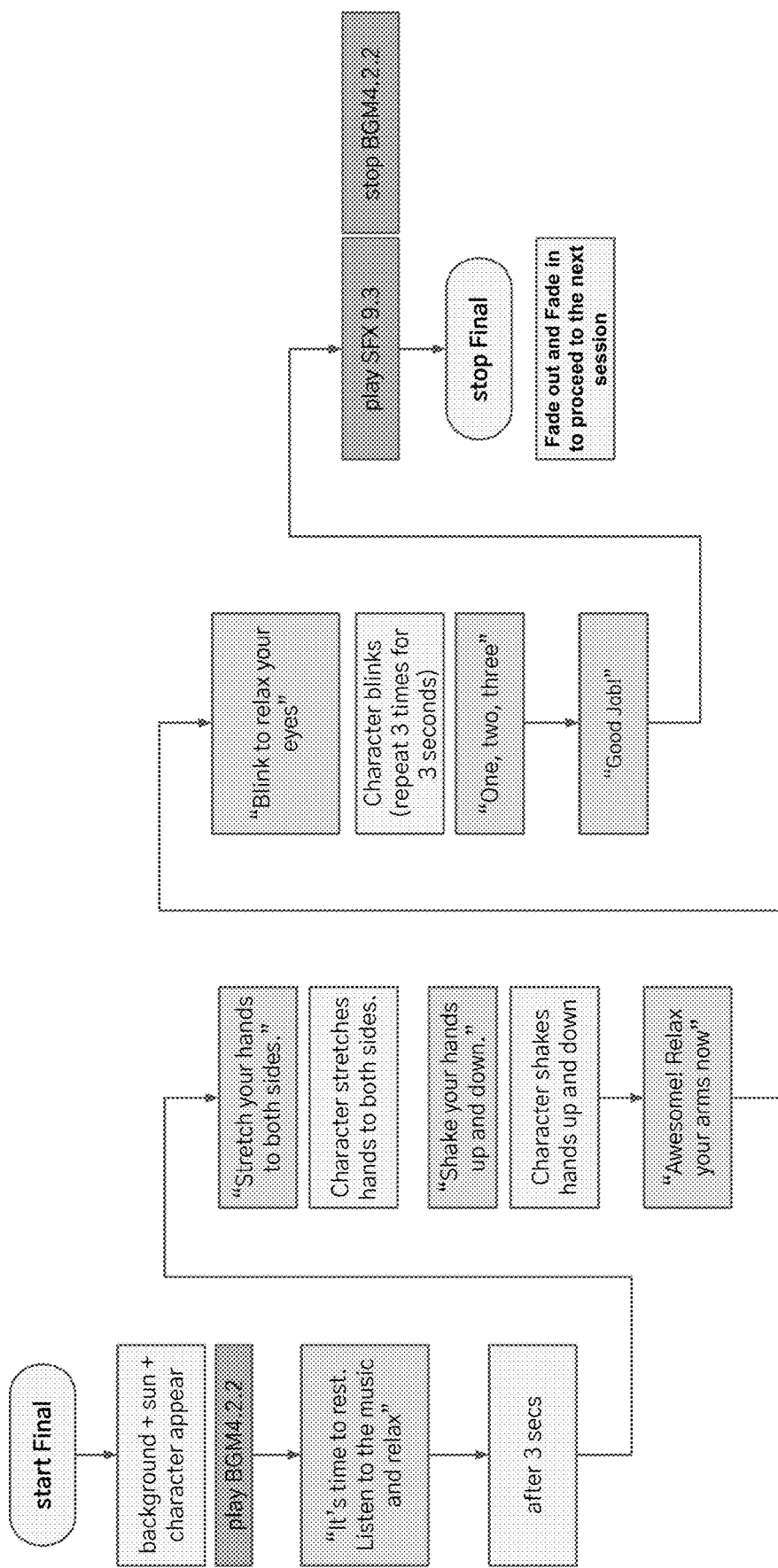
Figure 38:
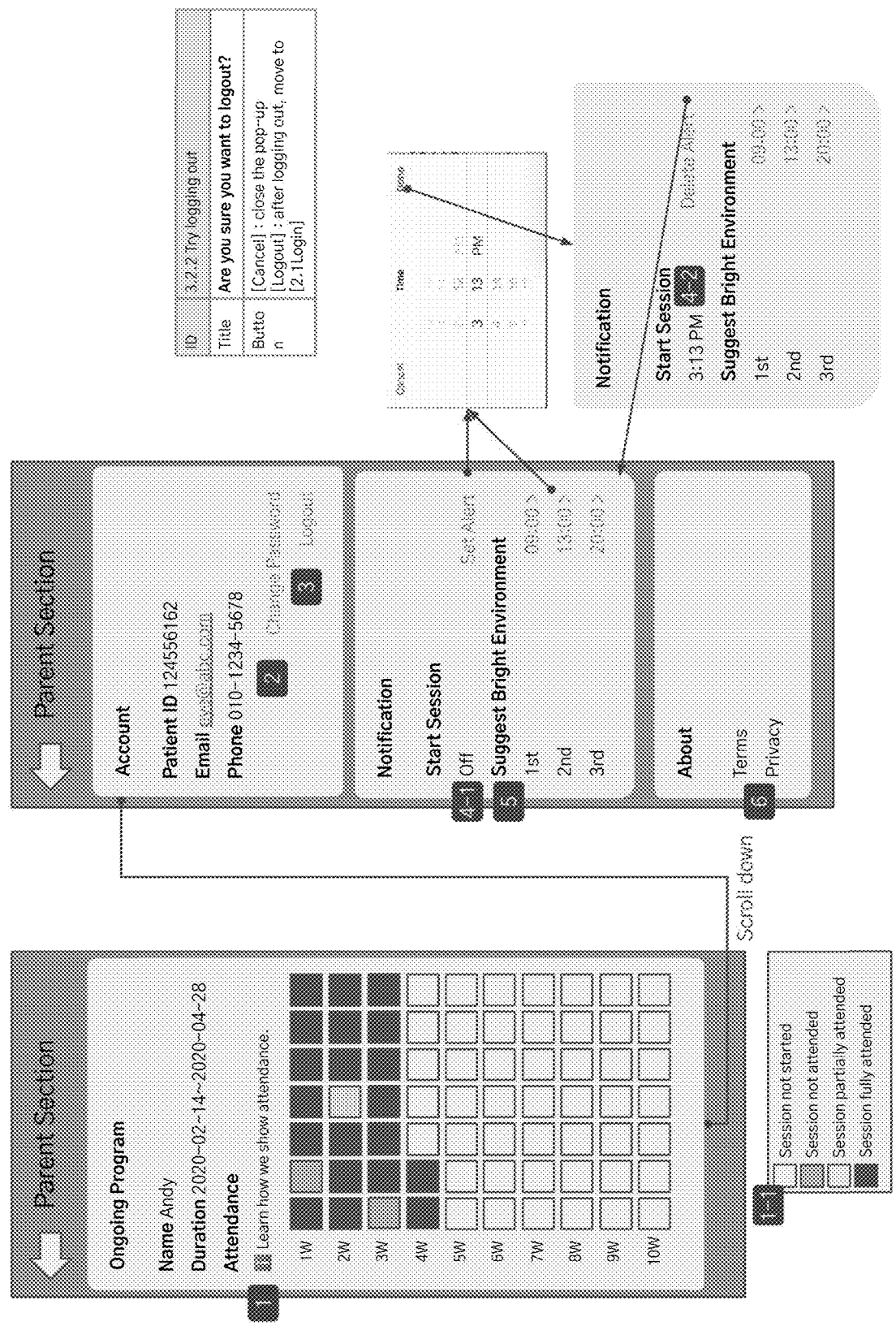
FIG. 38 depicts a screenshot of a Parent Section in a digital application of the present disclosure.
Figure 41:
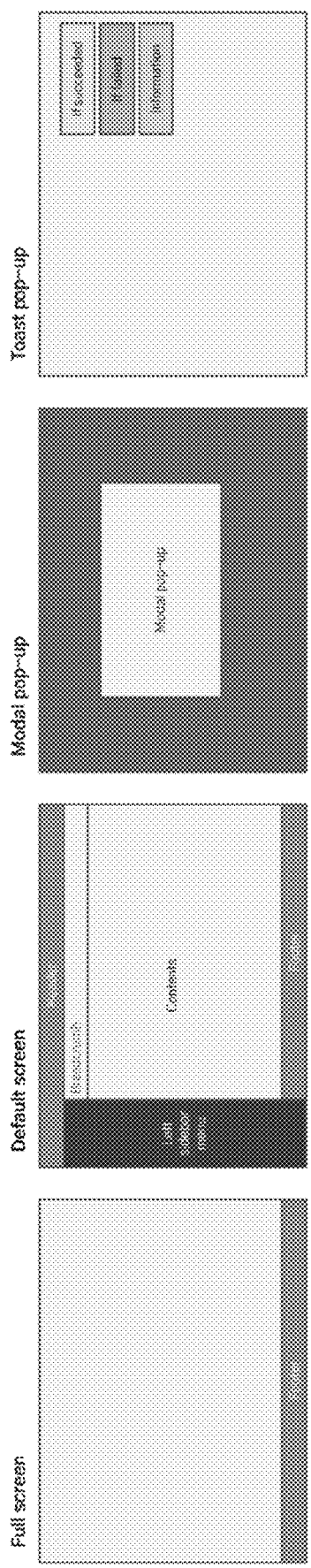
FIG. 41 depicts the layout for an exemplary healthcare provider portal and/or an administrative portal of the present disclosure. The full screen may be used in login screen, etc., and there may be no headers or side bar menus. The default screen may be used in almost all screens after logging in such as dashboard, patient list, etc. The modal pop-up may be used in situations where the user's click is needed such as checking before deleting a patient from the patient list. The toast pop-up may be used to provide adequate notifications to the users and may use different colors for each situation such as success or failure in order for the users to easily check.
Figure 42:
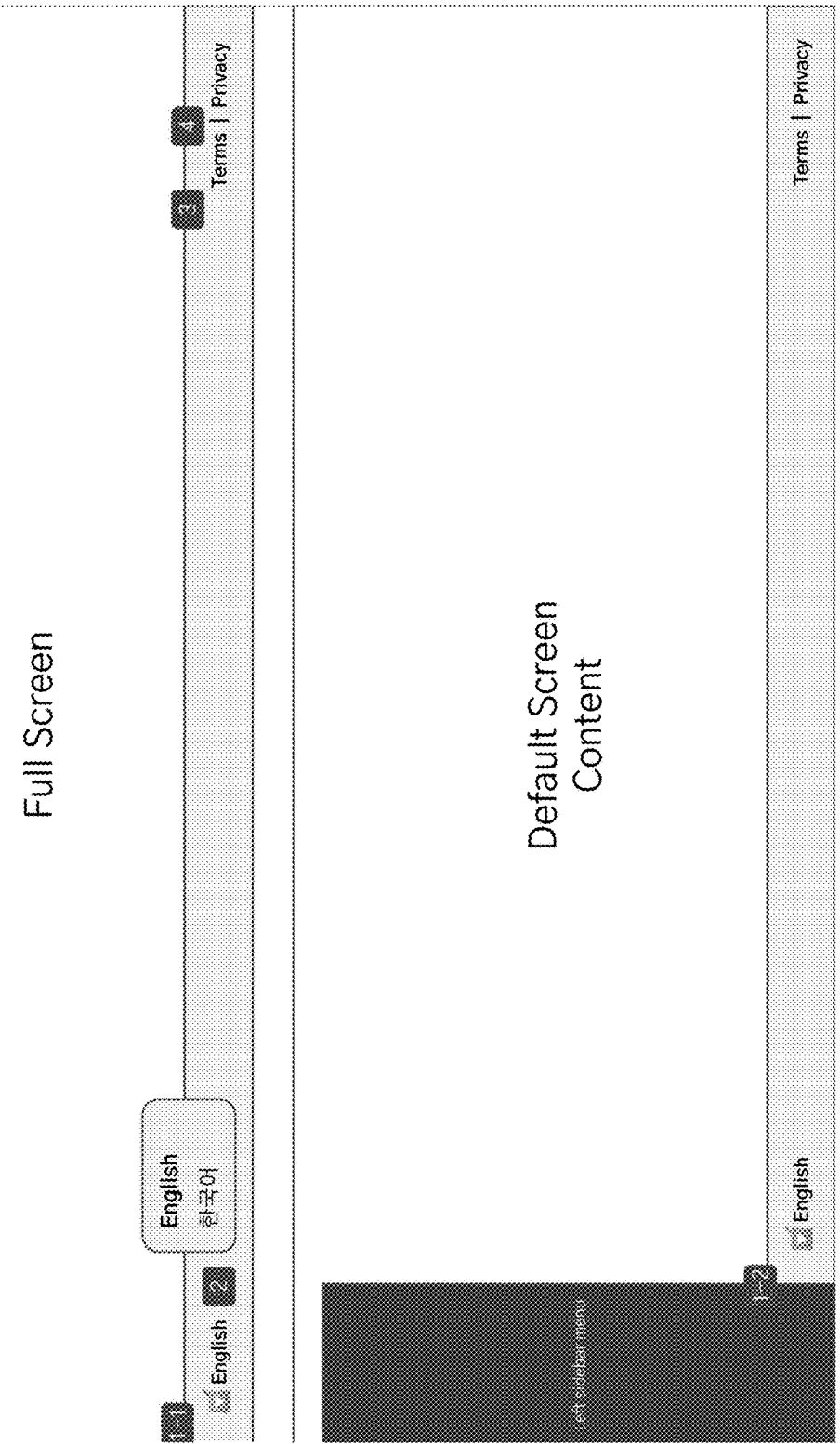
FIG. 42 depicts the layout for a healthcare provider portal and/or an administrative portal of the present disclosure.
Figure 43:
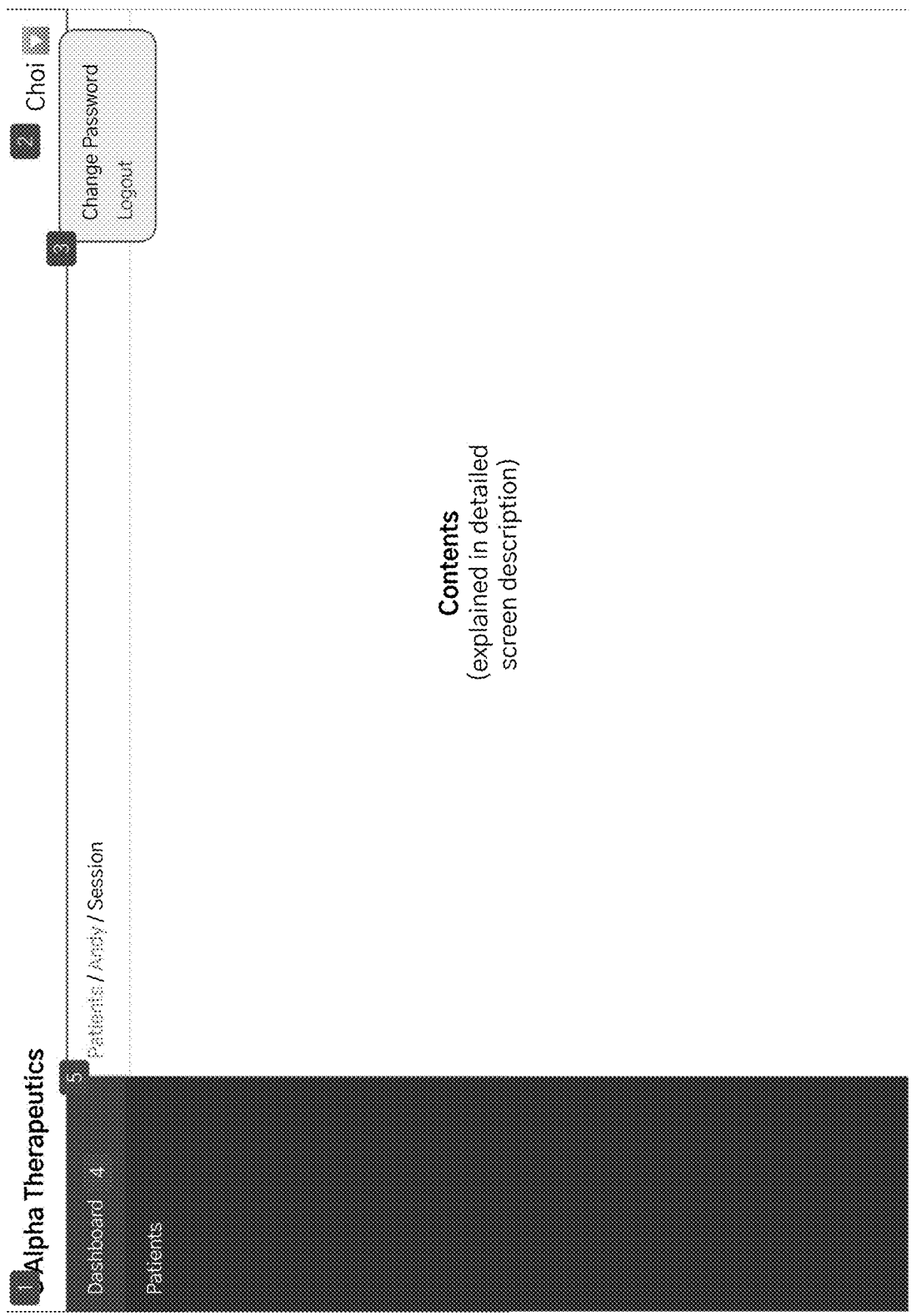
FIG. 43 depicts the layout for a healthcare provider portal and/or an administrative portal of the present disclosure.
Figure 44:
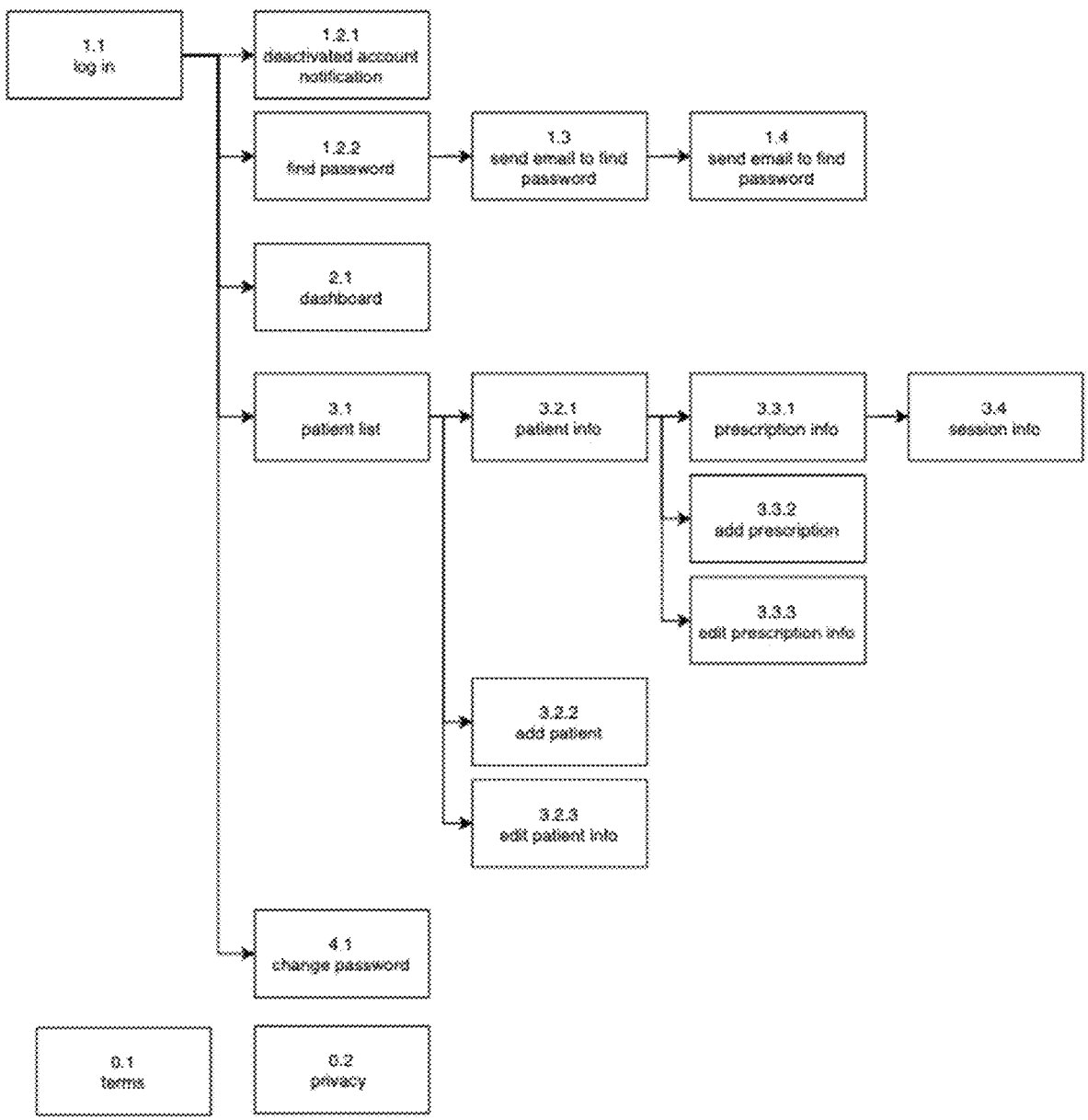
FIG. 44 is a flow chart illustrating an execution flow for a healthcare provider portal in a system of the present disclosure.

As described above, the availability of sessions may be determined during the prescription verification process. FIG. 23 depicts Home screens of the digital application of the present disclosure, wherein the Home screen indicates the availability of sessions for a subject to complete. As shown in FIG. 23, (1) Patient name: no tapping required, (2) Guardian mode entry button, (3) Room, which gets decorated as the treatment proceeds (decorations are automatically added or upgraded as the sessions are completed, and the decorations may display simple movements), (4) a character, which appears in the middle of the room, undergoes no changes during the treatment, and jumps up when tapped, (5) a Play button, (6) Notifications that the given daily sessions are completed, and (7) Notification of the end of the treatment program.

FIGS. 37A-B depict (A) a screenshot of a Room Decoration Board in an accomplishment module in a digital application of the present disclosure, and (B) a timeline showing the days on which a subject may acquire a given Room Decoration item. As shown, (1) a character, (2) a Room Decoration Board, where the numbers are presented like a calendar, and the Decoration Board maps a number or room decoration item for each date; the user cannot acquire the item on days with only numbers (3-2.) and vice versa on days with decoration items (3-1), and (4) shows items of 3-1 (room decoration items received) in close-up (e.g., a magnified view of the room decoration item(s) obtained).

In some embodiments, the digital application for treating myopia instructs a processor of the digital apparatus to execute operations comprising generating digital therapeutic modules for treating myopia based on a mechanism of action in and a therapeutic hypothesis for the myopia. In some embodiments, the digital therapeutic modules comprises generating the digital therapeutic modules based on neurohumoral factors related to the myopia onset.

Figure 19:
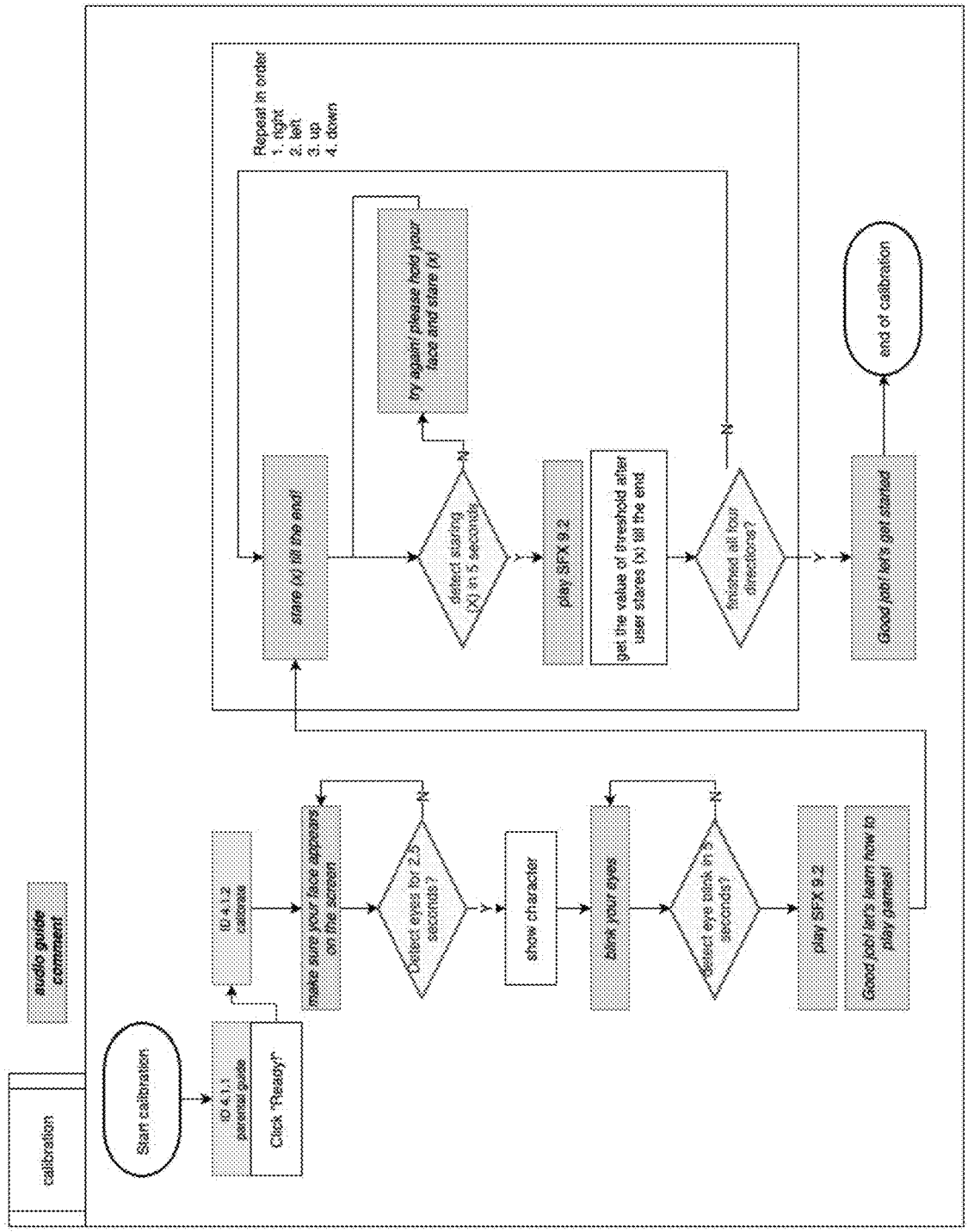
FIG. 19 is a flow chart illustrating an execution flow for a calibration module in a digital application of the present disclosure.

In some embodiments, the operations further comprise generating a calibration module for calibrating one or more of an accuracy of measurement of the subject's eye position, and a light environment. In some embodiments, the calibration module may be generated prior to generating the digital therapeutic modules. In some embodiments, the calibration module may not performed, and calibration settings from a previous session are used. Calibration may be performed at any time before, during, or after a session comprising two or more digital therapeutic modules. For example, calibration may precede the session. In another example, if the results from a digital therapeutic module exhibit large variability, the digital application may stop the session, and initiate calibration to confirm that the results of the digital therapeutic module are true, and not a result of poor calibration. FIG. 19 depicts a flow chart illustrating an execution flow for a calibration module in the digital application. Calibration may proceed at the start of the session each day for accuracy of eye measurement. Calibration may take between 35 and 60 seconds depending on the execution of outcomes. As shown in FIG. 19, the calibration module may comprise a series of instructions from the digital application to the subject such as orienting the subjects face in a particular direction (e.g., for better detection of the subject's eye(s)), or blinking the subject's eyes. FIG. 25 depicts a Calibration Notification screen of the digital application, wherein the Calibration Notification screen indicates whether a subject's eye and/or movement of the eye are detectable by the camera. As shown in FIG. 25, (1) a ready button, (2) a display of the Front Camera view on screen, (3) a character that is only shown when the digital application perceives the pupil (the character may be a 2D character with big eyes, which copy the user's eye movements, and may appear in a semi-transparent manner so that the user's face may be seen), and (4) a notice that provides action guides for user's guardian.

Figure 20:
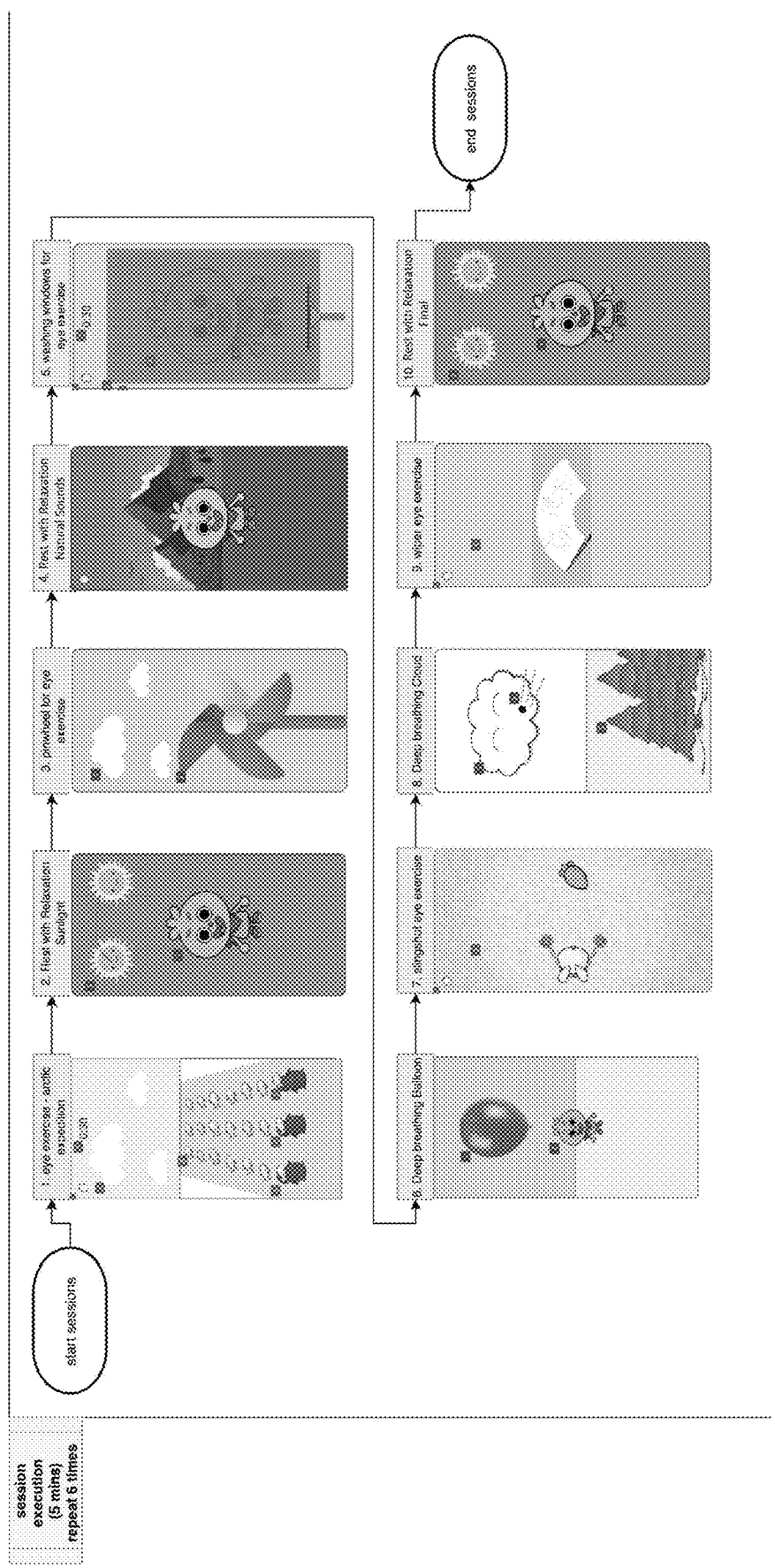
FIG. 20 is a flow chart illustrating an execution flow for a session in a digital application of the present disclosure, wherein the session comprises 2 or more digital therapeutic modules.

A session may comprise any number of digital therapeutic modules. In some embodiments, a session may comprise two or more digital therapeutic modules. In some embodiments, a session may comprise 3 or more, 4 or more, 5 or more, 6 or more, 7 or more, 8 or more, 9 or more, 10 or more, 11 or more, 12 or more, 13 or more, 14 or more, 15 or more, 20 or more, or 25 or more digital therapeutic modules. A session may comprise any number of digital therapeutic modules, and the digital therapeutic modules may be independently selected from an eye exercise module, a relaxation module, a deep breathing module, and a light therapy module. FIG. 20 depicts a flow chart illustrating an execution flow for a session in a digital application, wherein the session comprises 10 digital therapeutic modules. In some embodiments, a session may consist of 10 digital therapeutic modules, and the digital therapeutic modules comprise 5 eye exercise modules, 3 relaxation modules, and 2 deep breathing modules. A person of skill in the art will appreciate that there are a vast number of combinations for the number and type(s) of digital therapeutic modules that may go into a particular session. FIG. 26A through FIG. 35B depict various types of digital therapeutic modules (e.g., eye exercise, relaxation, and deep breathing).

In some embodiments, the accuracy of measurement of the subject's eye position may be calibrated, and said calibrating comprises determining threshold for detecting the subject's eyes. In additional embodiments, said calibrating the accuracy of measurement of the subject's eye position comprises one or more of instructing the subject to position their face to appear on a screen of the digital apparatus, detecting the subject's eyes for a given period of time, instructing the subject to blink their eyes, detecting if the subject blinked their eyes, instructing the subject to stare at the screen, instructing the subject to move their eyes in a given direction or rotate their eyes, and determining a threshold for detecting the subject's eyes. In some embodiments, the digital apparatus comprises one or more sensors for tracking movement of the subject's eyeball. The threshold for detecting the subject's eyes may be determined in a variety of ways. For example, the movement of eyes left to right may be scaled to 100 out of a maximum horizontal view. The movement of eyes from the top to bottom may also be scaled to 100 out of a maximum vertical view. Movement of the eyes for an average person is about 70 based on the scale of 100. For children and patients having myopia, movement of the eyes is less than 70. In one example, a threshold may be 70% of 70 (e.g., about 49). In another example, a threshold may be 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99% of a predetermined value based on the scale of 100. The predetermined value may be 70. In other embodiments, the threshold may be about 40, about 45, about 50, about 55, about 60, about 65, about 70, about 75, about 80, about 85, or about 90. In other embodiments, the threshold may be 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99 based on the scale of 100.

In one aspect, the digital therapeutic modules is generated based on the threshold. For example, an eye exercise module is generated based on the threshold. The eye exercise may include moving an object within 10, 9, 8, 7, 6, 5, 4, 3, 2, or 1 from a boundary of the threshold of the subject based on the scale of 100 in order to increase the threshold of the subject. The eye exercise may include moving an object within 10, 9, 8, 7, 6, 5, 4, 3, 2, or 1 from a boundary of the threshold of the subject after a sensor detects a gaze of eyes within 10, 9, 8, 7, 6, 5, 4, 3, 2, or 1 from a boundary of the threshold.

In some embodiments, the accuracy of measurement of the light environment may be calibrated, and said calibrating the light environment comprises one or more of detecting light in the subject's environment using a light sensor of the digital apparatus, and instructing the subject to turn on one or more lights in their environment. FIG. 24 depicts a Bright Environment Requirement Notification screen of a light therapy module of a digital application of the present disclosure, wherein the Bright Environment Requirement Notification screen indicates the amount of light detected by the digital apparatus. It is important to be exposed to bright light while performing eye exercise. The room starts at a very messy state, and becomes clean as the digital apparatus perceives the light. The digital application exposes the patient to bright light at least 3 times a day. After launching the app, the camera sensor perceives bright light and the lights that are off turn on. As shown in FIG. 24, (1) the light bulb helps induce the user to be exposed to bright light 3 times a day. All lights are off on the very first launch of the digital application (1-1), and the light bulbs start to go on after perceiving sufficient light (1-2), (2) an inducement element help induce the user to be exposed to bright light (e.g., dark background, spider, spider web, dust, etc.), (3) skipping the bottom of home element (e.g., play button, and completion notifications are left out on this page).

In some embodiments, the digital application for treating myopia instructs a processor of the digital apparatus to execute operations. In some embodiments, the executed operations comprise generating digital therapeutic modules for treating myopia based on a mechanism of action in and a therapeutic hypothesis for the myopia. In some embodiments, the executed operations comprise generating digital instructions based on the digital therapeutic modules. In some embodiments, the executed operations comprise providing the digital instruction to a subject. In some embodiments, the executed operations comprise collecting the subject's execution outcomes of the digital instructions. In some embodiments, the generating of the digital instructions and the collecting of the subject's execution outcomes of the digital instructions are repeatedly executed several with multiple feedback loops. In some embodiments, the generating of the digital instructions comprises generating the subject's digital instructions for this cycle based on the subject's digital instructions in the previous cycle and the collected execution outcome data on the subject's digital instructions provided in the previous cycle.

In some embodiments, the given interval at which a location of the eyeball is measured is about 10 milliseconds (ms), 25 ms, 50 ms, 60 ms, 70 ms, 80 ms, 90 ms, 100 ms, 110 ms, 120 ms, 130 ms, 140 ms, 150 ms, 175 ms, 200 ms, 250 ms, 300 ms, 350 ms, 400 ms, or a range of two values therebetween. In some embodiments, the given interval at which a location of the eyeball is measured is between about 10 ms, and about 500 ms, about 50 ms and about 250 ms, about 75 and about 150 ms, or about 90 ms and about 110 ms.

In some embodiments, the generating of the digital therapeutic modules comprises generating the digital therapeutic modules by applying imaginary parameters about the subject's environments, behaviors, emotions, and cognition to the mechanism of action in and the therapeutic hypothesis for the myopia.

In some embodiments, the digital application for treating myopia instructs a processor of the digital apparatus to generate digital therapeutic modules comprising two or more modules selected from the group consisting of an eye exercise module, a relaxation module, and a light therapy module.

In some embodiments, the eye exercise module comprises one or more exercise instructions for one or more of: eyeball exercise instructions, biofeedback control instructions, and eyeball-related behavior control instructions.

In some embodiments, the relaxation module comprises one or more relaxation instructions for one or more of: physical exercise instructions, ego enhancement instructions, safety feeling instructions, comfort feeling instructions, and fun instructions. In some embodiments, the light therapy module comprises one or more light therapy instructions for controlling a light environment of the subject. In some embodiments, the one or more relaxation instructions comprise one or more of playing a sound or song, inducing blinking, and instructing the subject to perform gymnastics.

In some embodiments, the digital therapeutic modules further comprise an accomplishment module comprising one or more accomplishment instructions for task accomplishment and for providing compensation for the subject's adherence to the instructions of the two or more first modules. In some embodiments, the digital therapeutic modules further comprise a fun module comprising one or more fun instructions for music, games, or videos.

In some embodiments, the healthcare provider portal provides a healthcare provider with one or more options, and the one or more options provided to the healthcare provider are selected from the group consisting of adding or removing the subject, viewing or editing personal information for the subject, viewing adherence information for the subject, viewing a result of the subject for one or more at least partially completed digital therapeutic modules, prescribing one or more digital therapeutic modules to the subject, altering a prescription for one or more digital therapeutic modules, and communicating with the subject. In some embodiments, the one or more options comprise the viewing or editing personal information for the subject, and the personal information comprises one or more selected from the group consisting of an identification number for the subject, a name of the subject, a date of birth of the subject, an email of the subject, an email of the guardian of the subject, a contact phone number for the subject, a prescription for the subject, and one or more notes made by the healthcare provider about the subject. In some embodiments, the personal information comprises the prescription for the subject, and the prescription for the subject comprises one or more selected from the group consisting of a prescription identification number, a prescription type, a start date, a duration, a completion date, a number of scheduled or prescribed digital therapeutic modules to be performed by the subject, and a number of scheduled or prescribed digital therapeutic modules to be performed by the subject per day. In some embodiments, the one or more options comprise the viewing the adherence information, and the adherence information of the subject comprises one or more of a number of scheduled or prescribed digital therapeutic modules completed by the subject, and a calendar identifying one or more days on which the subject completed, partially completed, or did not complete one or more scheduled or prescribed digital therapeutic modules. In some embodiments, the one or more options comprise the viewing the result of the subject, and the result of the subject for one or more at least partially completed digital therapeutic modules comprises one or more selected from the group consisting of a time at which the subject started a scheduled or prescribed digital therapeutic module, a time at which the subject ended a scheduled or prescribed digital therapeutic module, an indicator of whether the scheduled or prescribed digital therapeutic module was fully or partially completed, and an exercise intensity (EI).

Figure 45A:
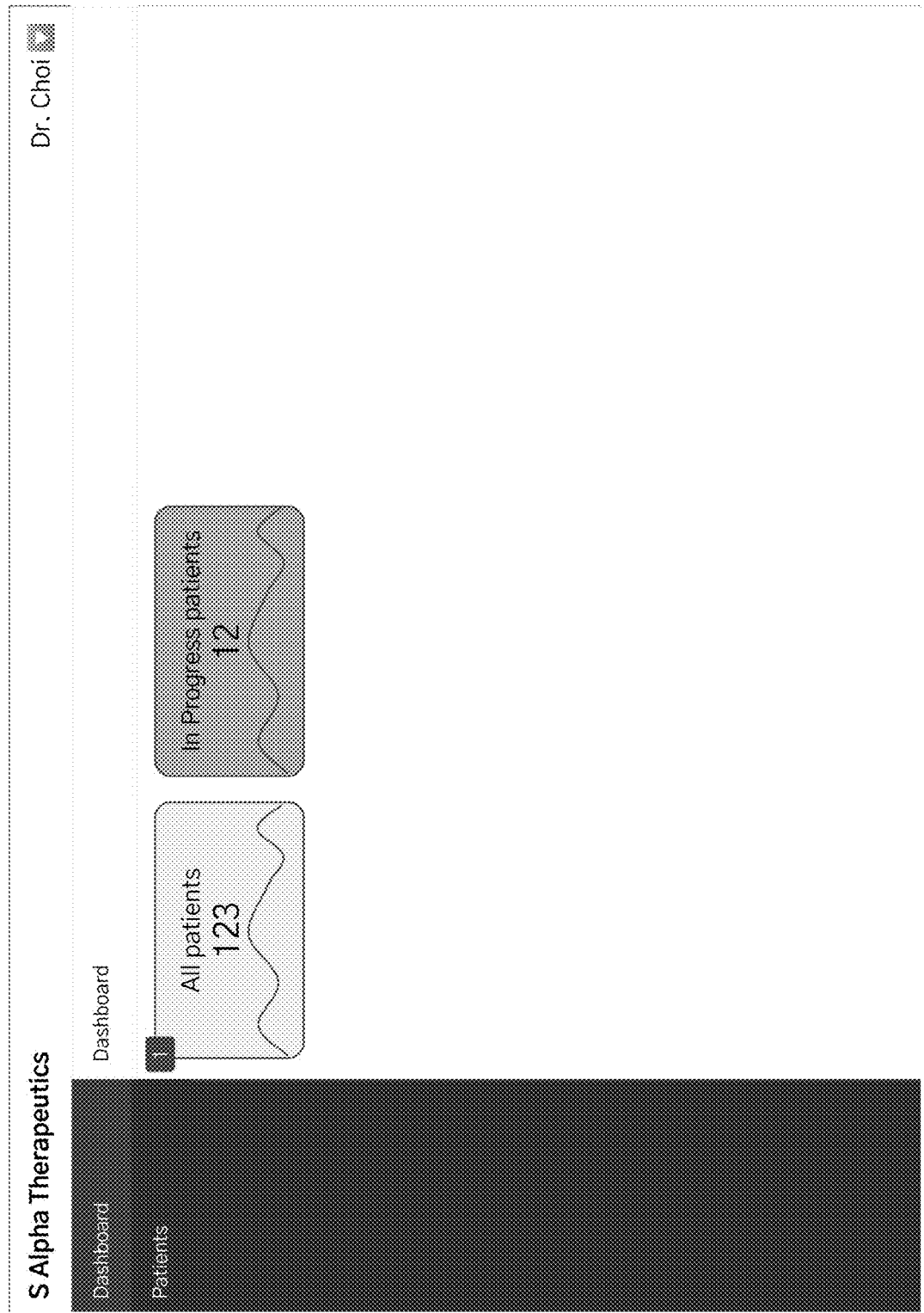
Figure 45B:
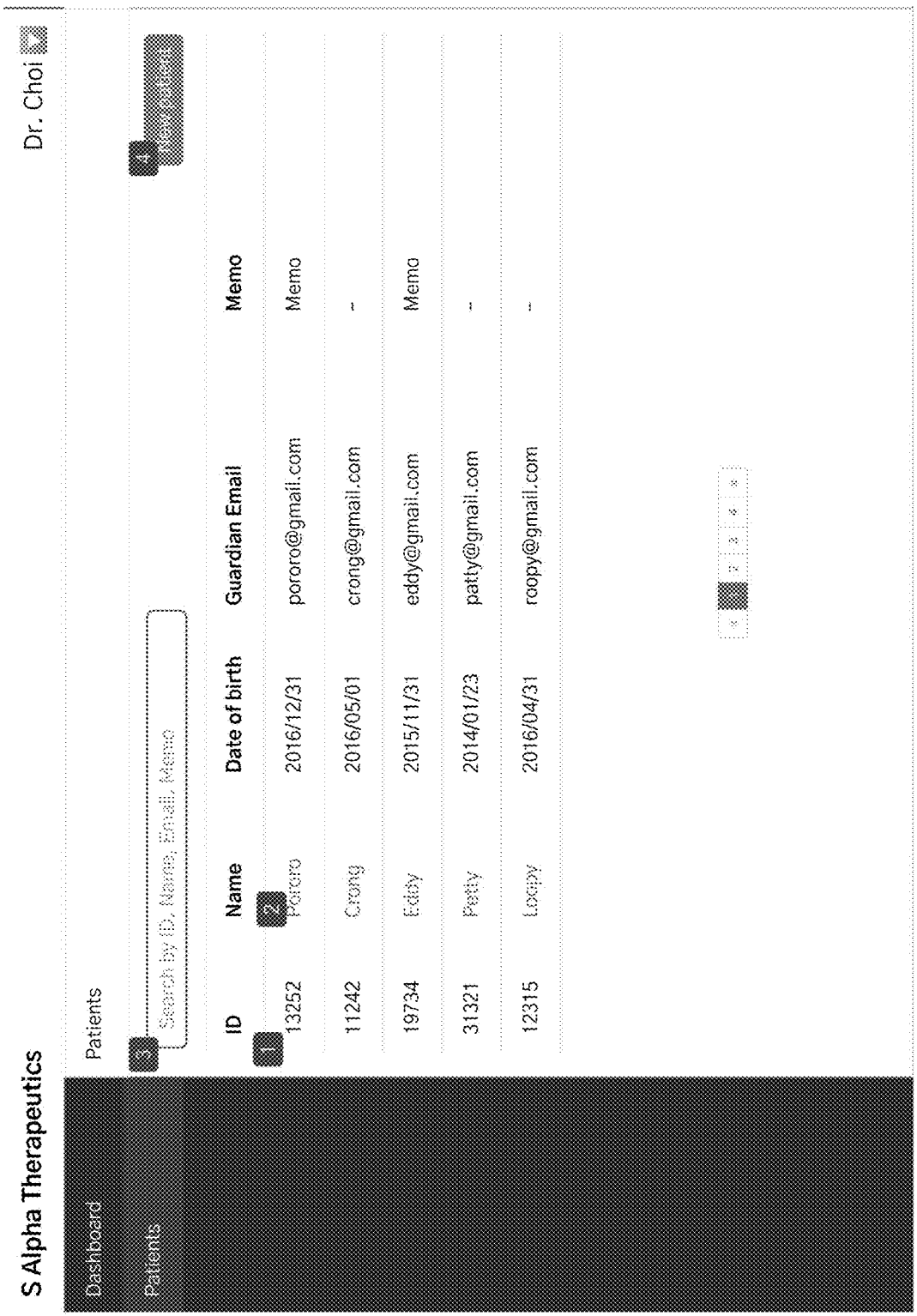
Figure 45C:
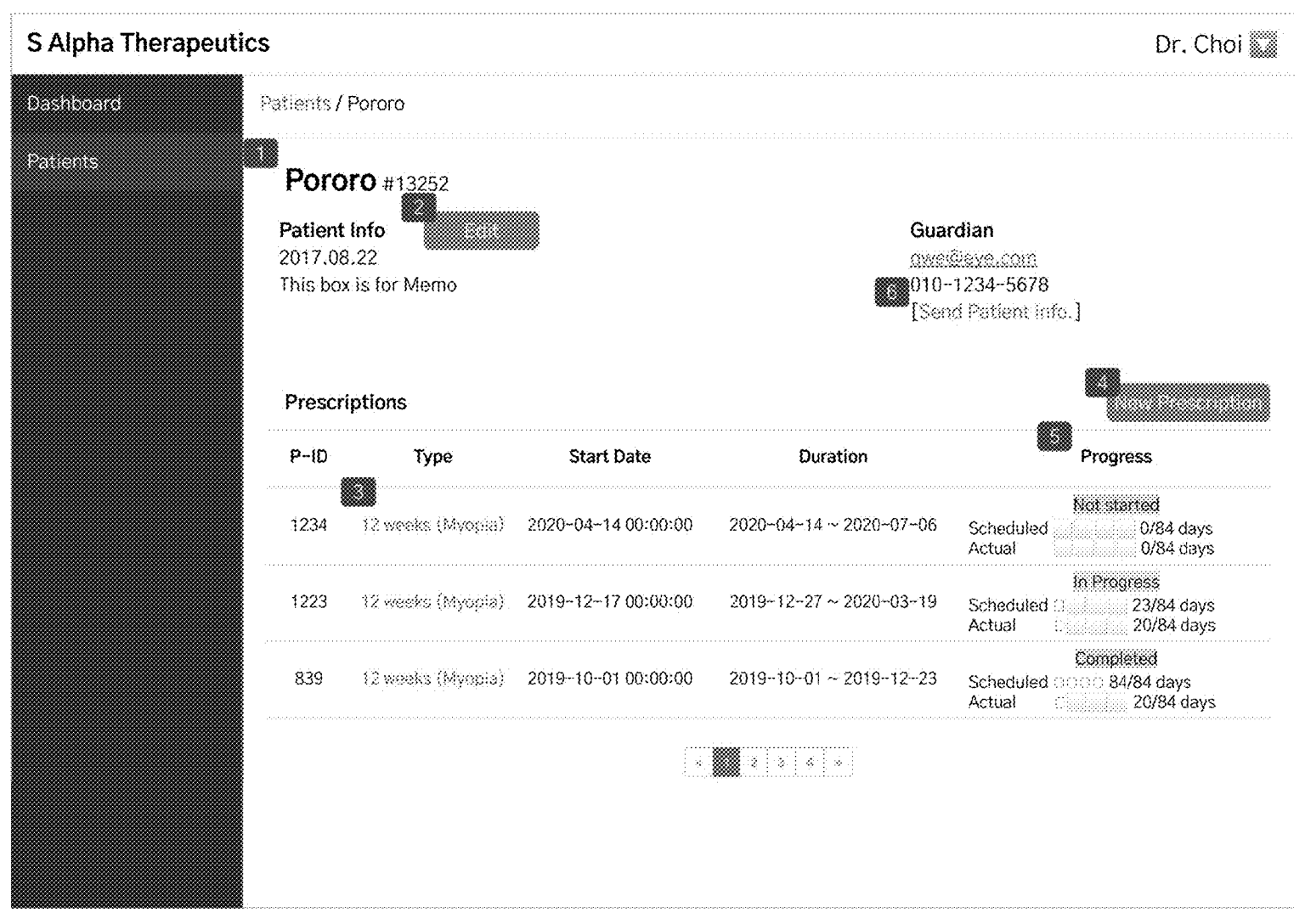
Figure 45D:
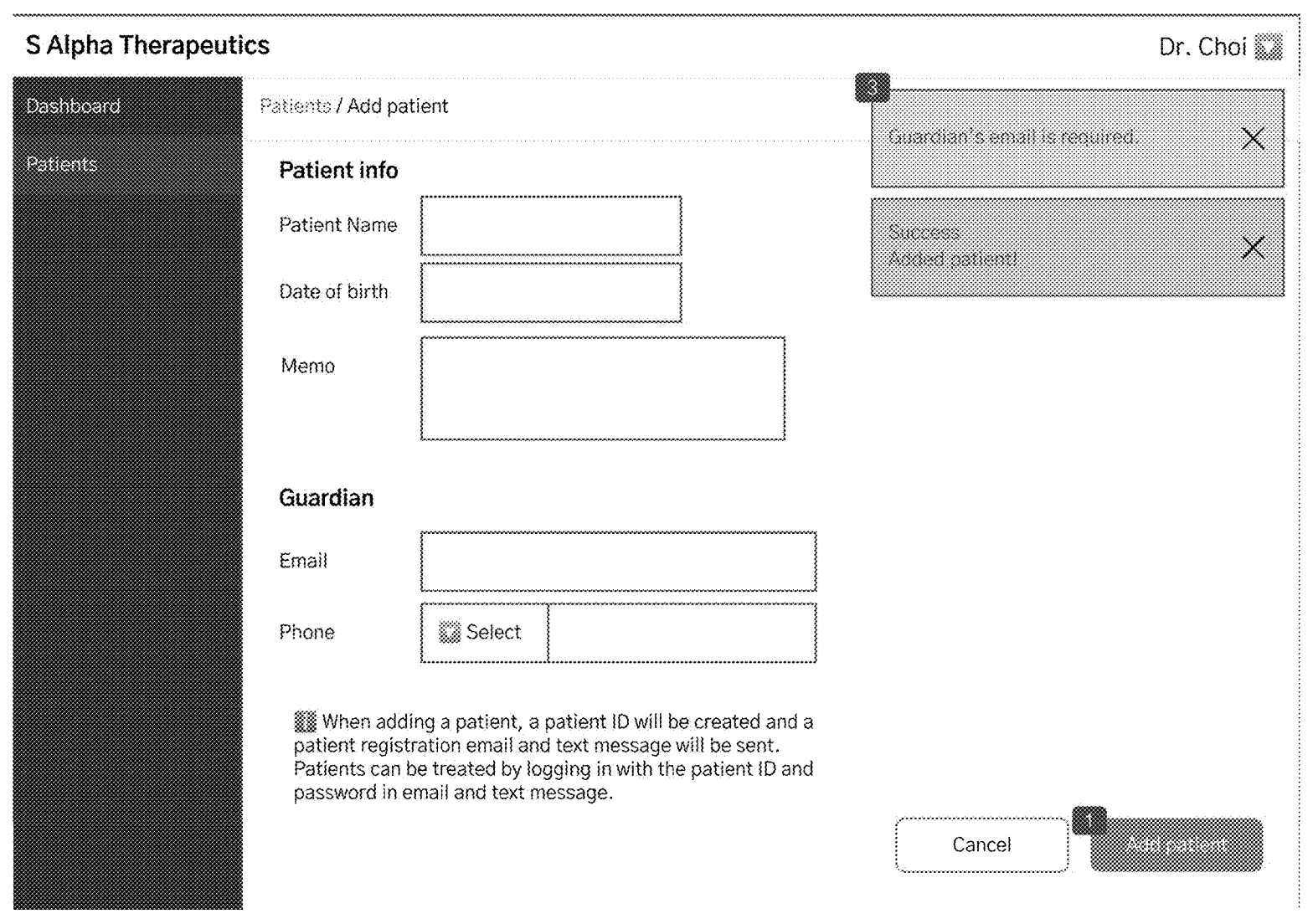
Figure 45E:
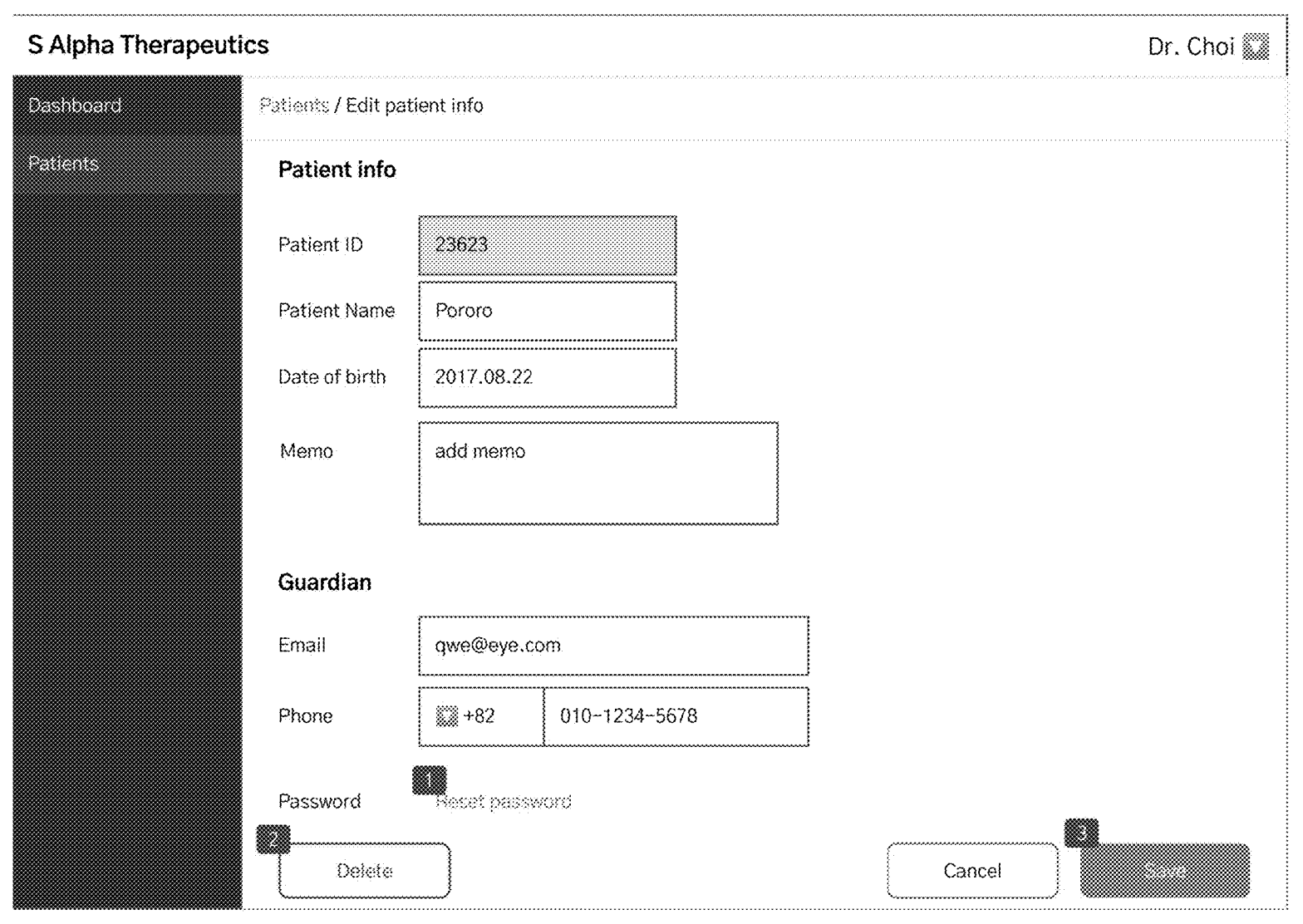
Figure 45F:
Figure 45G:
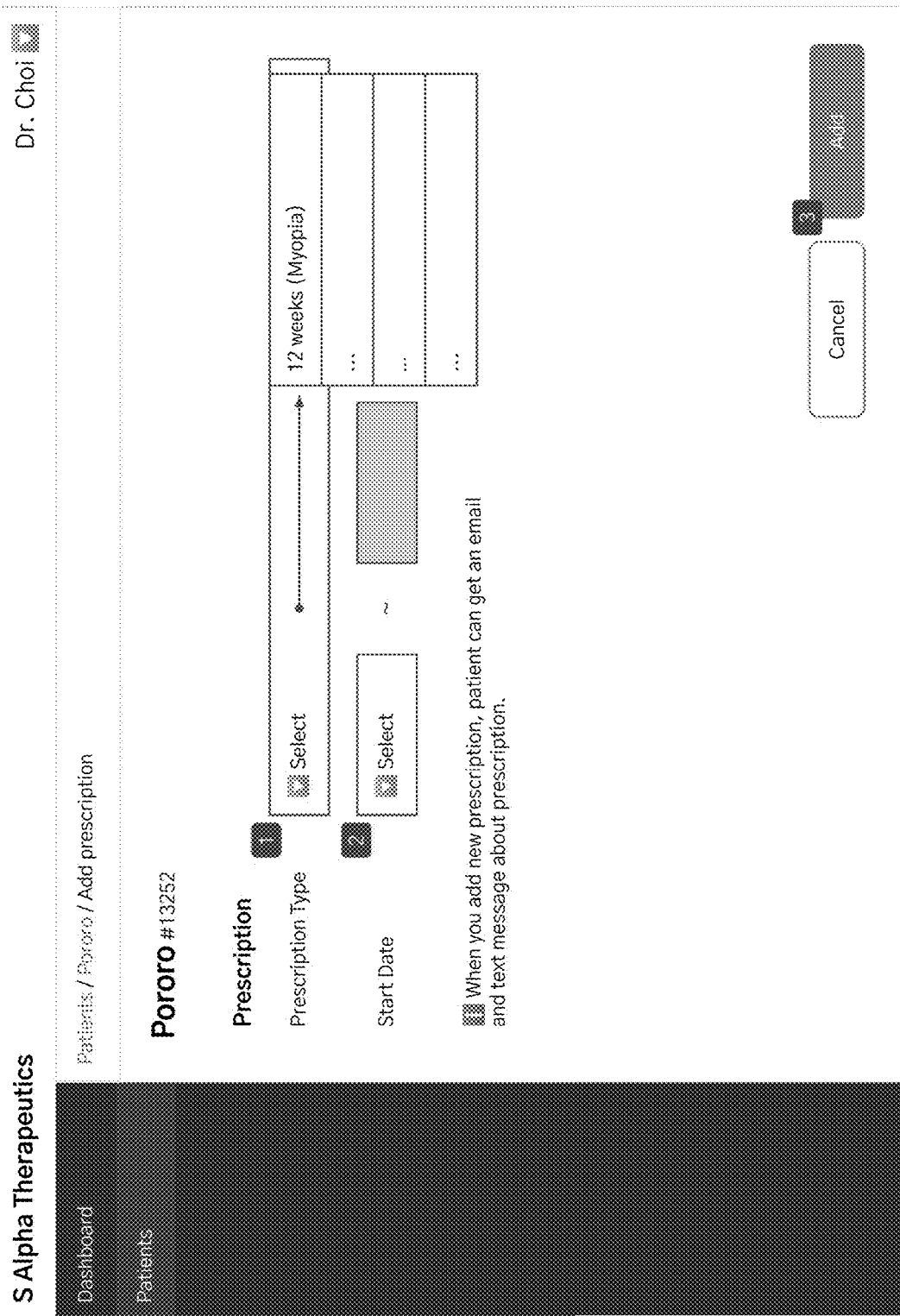
Figure 45H:
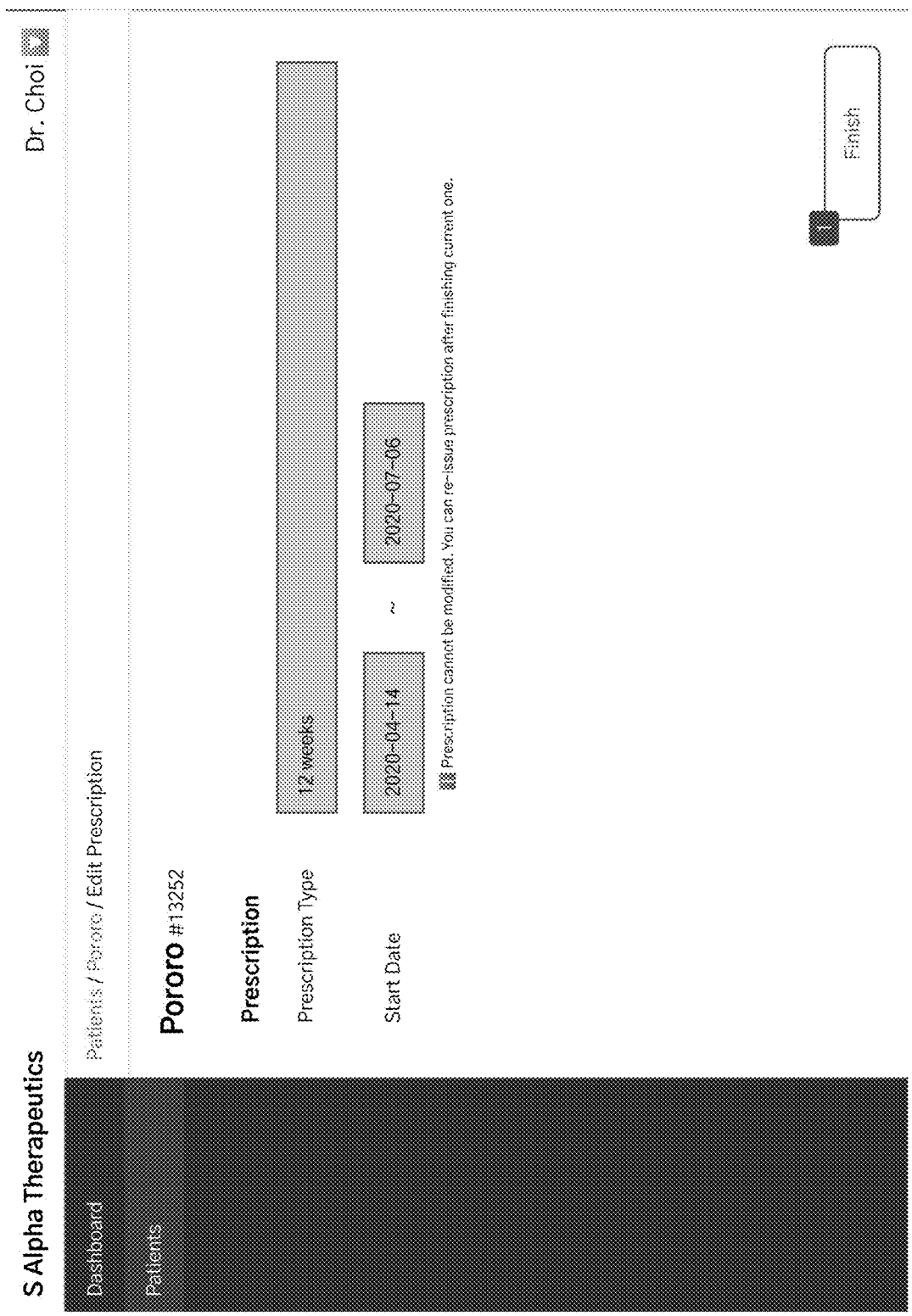
Figure 45I:
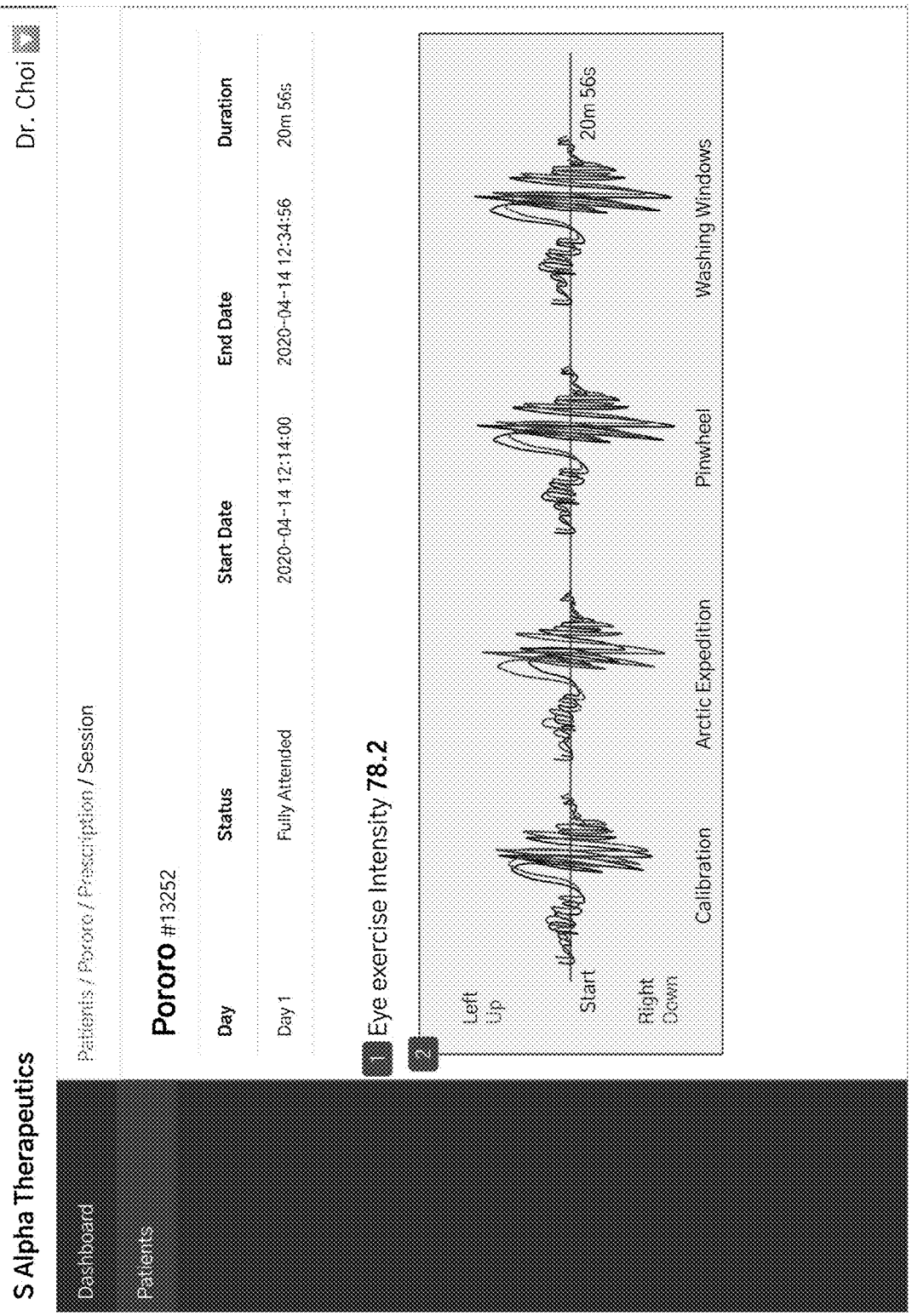
Figure 46:
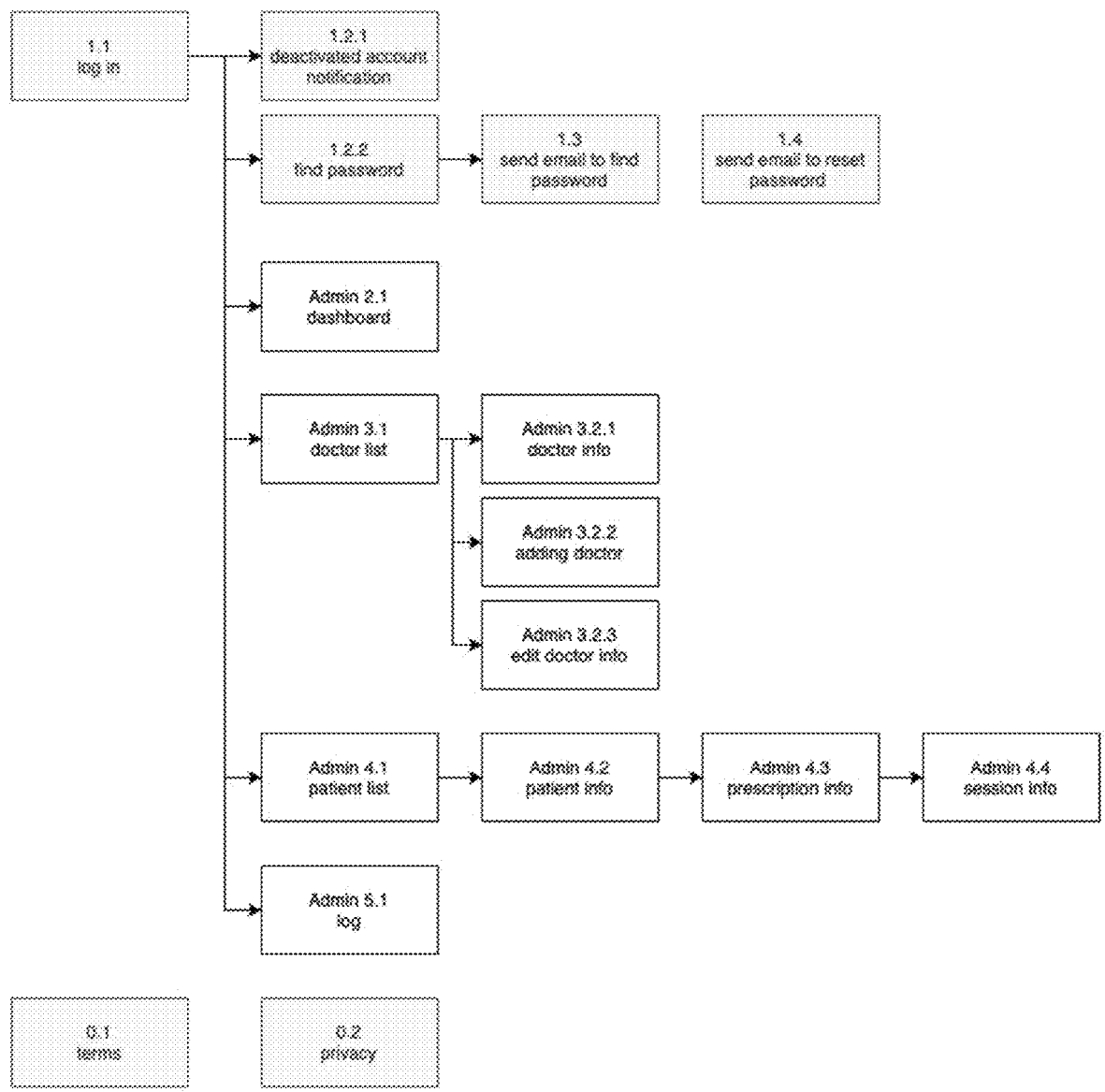
FIG. 46 is a flow chart illustrating an execution flow for an administrative portal in a system of the present disclosure.

FIG. 45A depicts a dashboard of a healthcare provider portal. (1) The number of all patients associated with the present doctor's account. A graph may be used to show the number of patients who have opened the digital application for patient per day in the most recent 90 days. The number of patients in progress may also be viewed. A graph may be used to show the number of patients who have completed the daily sessions per day in the most recent 90 days. FIG. 45B depicts a patient tab in a healthcare provider portal, the patient tab displaying a list of patients. As shown, (1) Patient ID (the unique identification number temporarily given to each patient when adding them on the list), (2) Patient Name, (3) Search bar for searching by ID, Name, Email, Memo, etc., and (4) Add New Patient button for adding new patients. FIG. 45C depicts a patient tab in a healthcare provider portal, the patient tab displaying detailed information on a given patient. As shown, (1) detailed patient information, (2) a button for editing patient information, (3) prescription information, (4) a button for adding a new prescription, (5) displays a progress status for different each prescription, and (6) a button or link for sending an email to the patient. FIG. 45D depicts a patient tab in a healthcare provider portal for adding a new patient. As shown, (1) shows a button for adding a new patient, and (3) shows an error message displayed when required patient information has not been provided. FIG. 45E depicts a patient tab in a healthcare provider portal for editing information of an existing patient. As shown, (1) is a button or link for resetting a password, (2) is a button for deleting a given patient, and (3) is a button for saving changes. FIG. 45F depicts a patient tab in a healthcare provider portal that displays detailed prescription information for a given patient. As shown, (1) is a button for editing prescription information, (2) displays the duration of the sessions attended by the patient or subject, and (3) shows an overview the treatment progress. Seven days are represented as a line or row of 7 squares. For 12 weeks, each 6 weeks may be presented separately. Different colors may be used to discern session statuses (e.g., grey for sessions not started, red for sessions not attended, yellow for sessions partially attended, and green for sessions fully attended). FIGS. 45G-H depict a patient tab in a healthcare provider portal for editing prescription information for a given patient. FIG. 45I depicts a patient tab in a healthcare provider portal for viewing details (e.g., date, status, duration, results such as EI or AEI) of a given session for a given patient. As shown, (1) is the eye exercise intensity, and (2) is a graph of the exercise intensity. Different colors may be used in the graph to differentiate between up/down or right/left movement of the eye. In the graph, the larger the amplitude, the more the eye has been exercised.

In some embodiments, collecting the subject's execution outcomes of the digital instructions comprises determining one or both of an exercise intensity (EI) and an average exercise intensity (AEI). In some embodiments, AEI may be determined as an averaged sum of differences between a final location of an eyeball of the subject and a starting location of the eyeball measured at a given interval. The EI may be determined according the formula:

$$EI = \frac{AEI \times 100}{145}$$

In certain embodiments, total AEI can be determined as a sum of dynamic AEI and static AEI. Dynamic AEI may be determined based on the eyeball movement over a given time, and static AEI may be determined based on holding a stretched position for an eyeball over a given time. For example, while dynamic AEI can be determined as the averaged sum of differences between a final location of an eyeball of the subject and a starting location of the eyeball measured over given interval (e.g., corresponding to a measure of the how much an eyeball is moving), static AEI can be determined as the averaged sum of distances of the eyeball from a resting position (e.g., looking straight ahead) measured over given interval as the eyeball is fixed in place (e.g., not moving). With respect to dynamic AEI, when the eyeball tracking is started with the eye in a resting position (time=0), AEI is calculated by measuring changes in distance travelled by the eyeball (d) over a given interval (e.g., 10 to 500 msec). That is, if d is large, a lot of eye movement is measured, resulting in a high AEI. Small changes in d (e.g., when the eyeball moves less or not at all) result in a low AEI. However, dynamic AEI does not account for exercise of the eye muscles when the eye is fixed at a location that is not the resting position. In other words, over a given interval, the subject's eye can be held at a position that is not the resting state (e.g., d=0), however eye muscles are still being exercised in order to hold the eye at that position. Static AEI accounts exercise of the eye that is not related to eye movement.

In some embodiments, the administrative portal provides an administrator with one or more options, and the one or more options provided to the administrator of the system are selected from the group consisting of adding or removing the healthcare provider, viewing or editing personal information for the healthcare provider, viewing or editing de-identified information of the subject, viewing adherence information for the subject, viewing a result of the subject for one or more at least partially completed digital therapeutic modules, and communicating with the healthcare provider. In some embodiments, the one or more options comprise the viewing or editing the personal information, and the personal information of the healthcare provider comprises one or more selected from the group consisting of an identification number for the healthcare provider, a name of the healthcare provider, an email of the healthcare provider, and a contact phone number for the healthcare provider. In some embodiments, the one or more options comprise the viewing or editing the de-identified information of the subject, and the de-identified information of the subject comprises one or more selected from the group consisting of an identification number for the subject, and the healthcare provider for the subject. In some embodiments, the one or more options comprise the viewing the adherence information for the subject, and the adherence information of the subject comprises one or more of a number of scheduled or prescribed digital therapeutic modules completed by the subject, and a calendar identifying one or more days on which the subject completed, partially completed, or did not complete one or more scheduled or prescribed digital therapeutic modules. In some embodiments, the one or more options comprise the viewing the result of the subject, and the result of the subject for one or more at least partially completed digital therapeutic modules comprises one or more selected from the group consisting of a time at which the subject started a scheduled or prescribed digital therapeutic module, a time at which the subject ended a scheduled or prescribed digital therapeutic module, an indicator of whether the scheduled or prescribed digital therapeutic module was fully or partially completed, and an exercise intensity (EI).

Figure 47A:
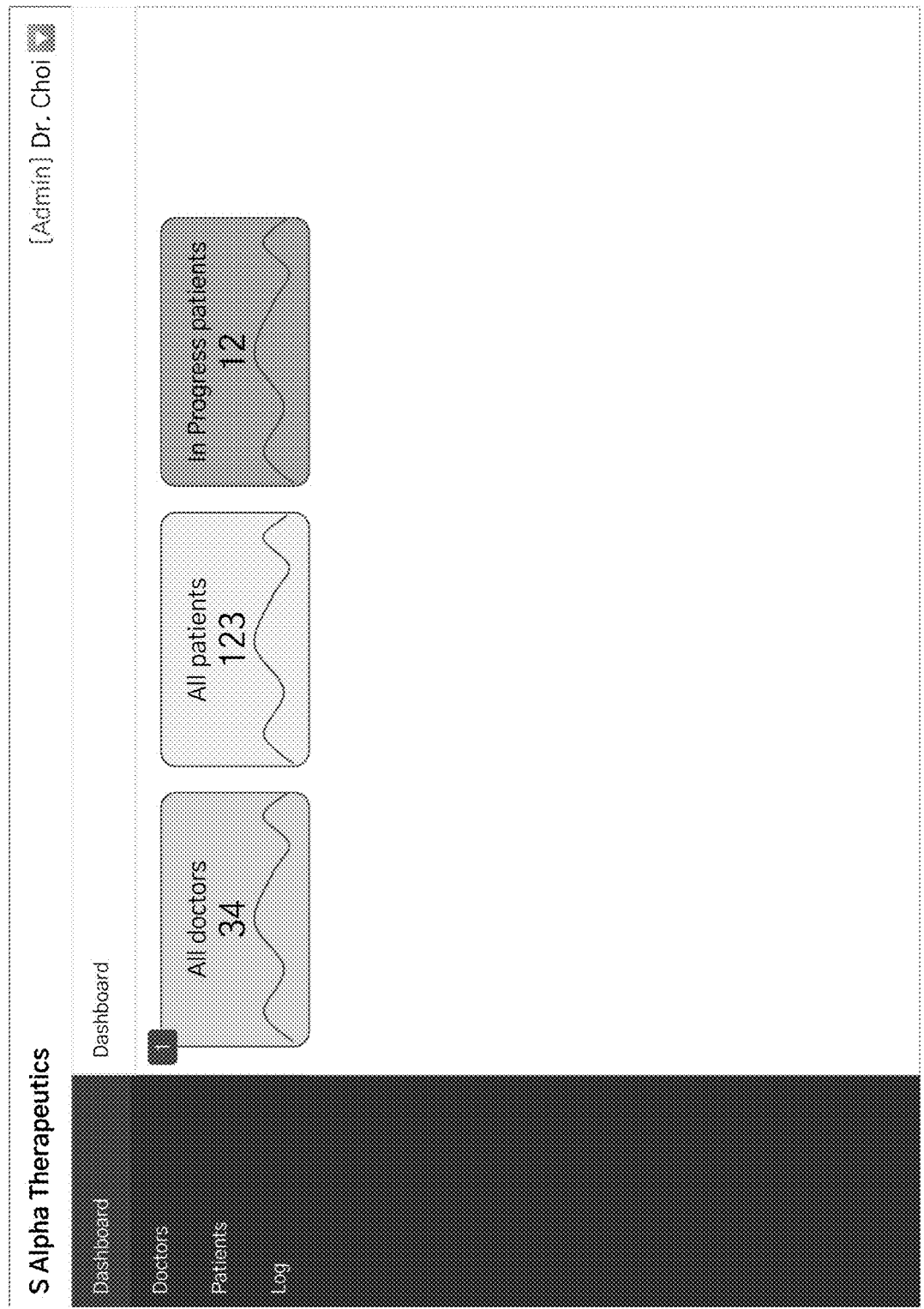
Figure 47B:
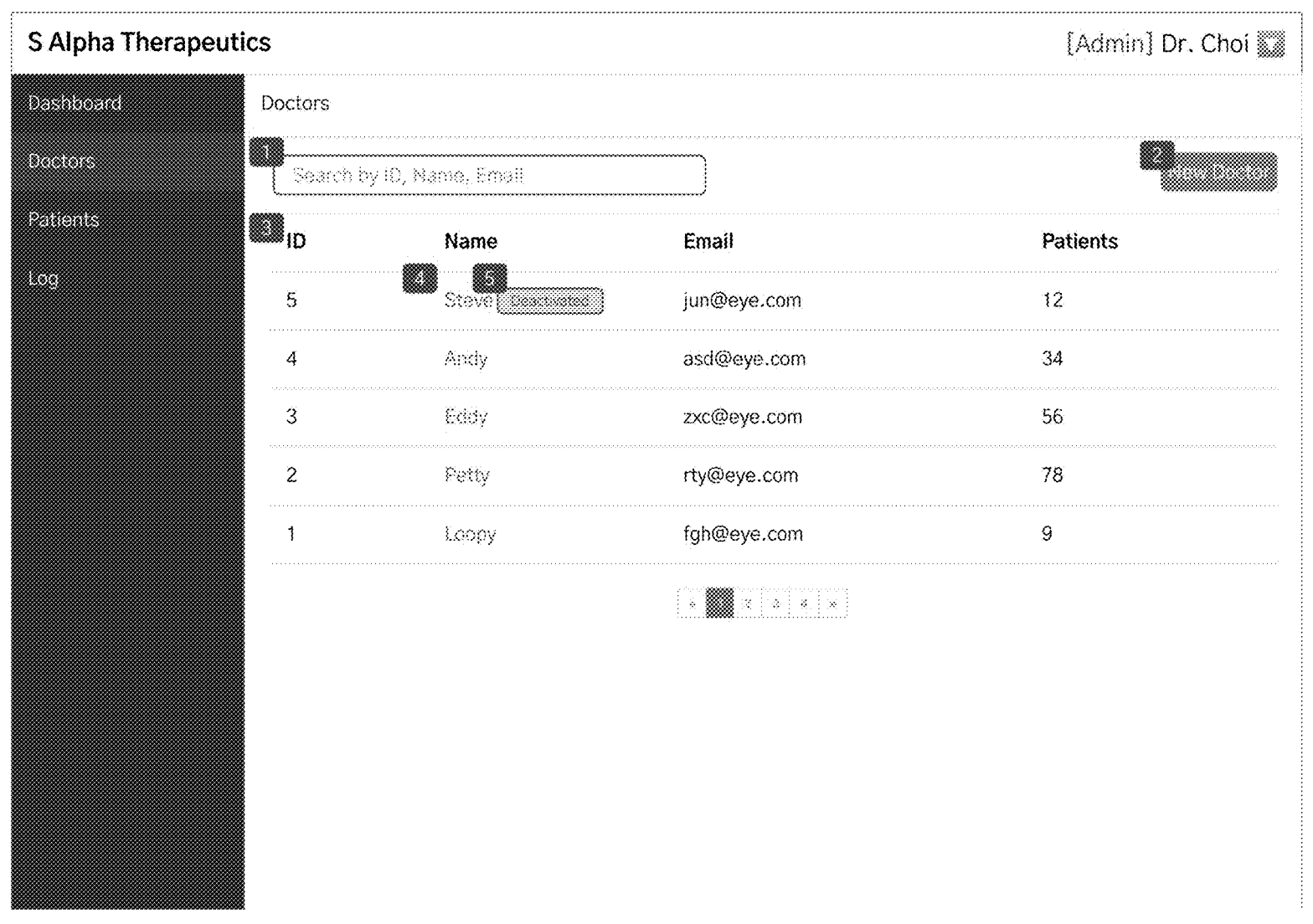
Figure 47C:
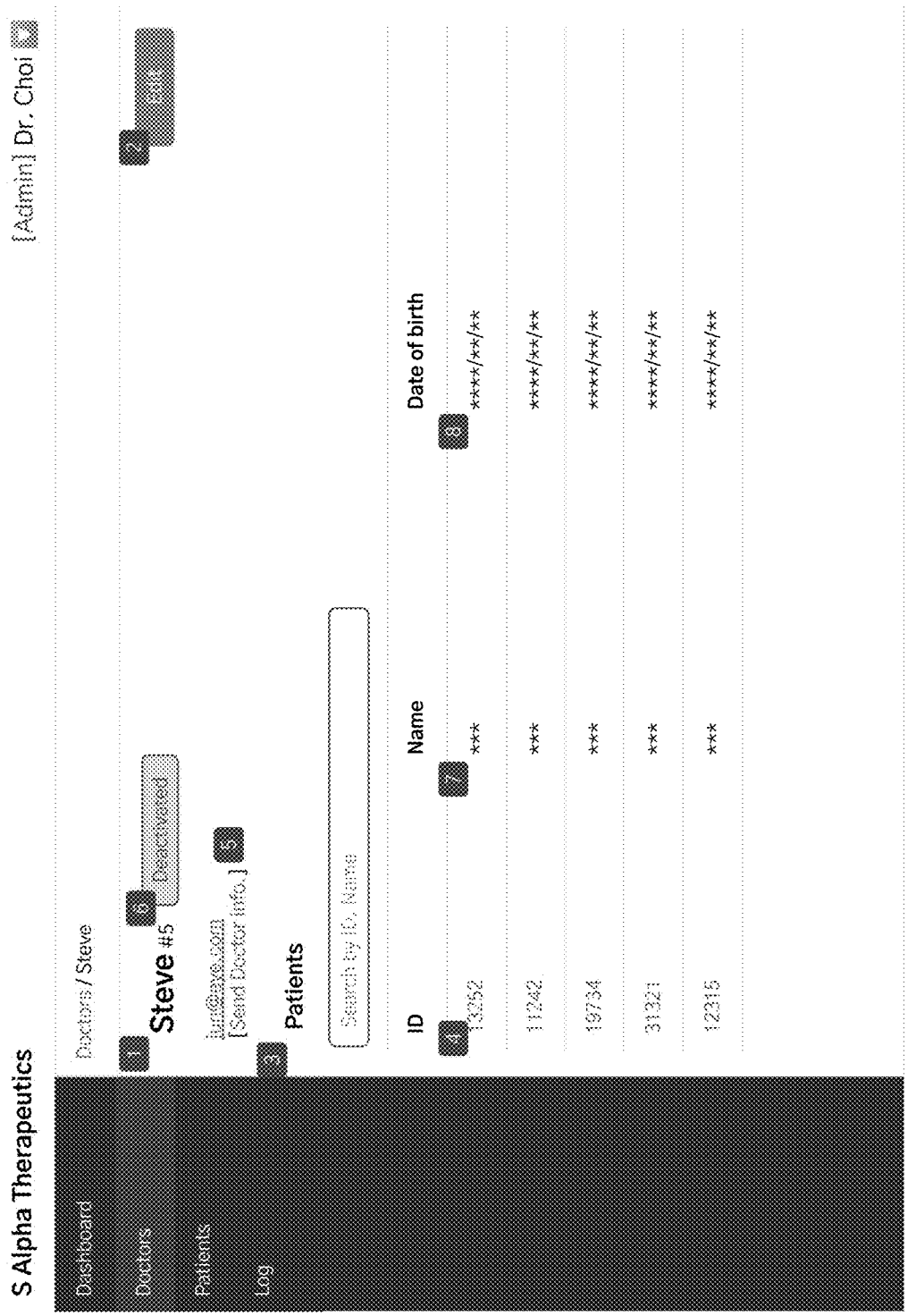
Figure 47D:
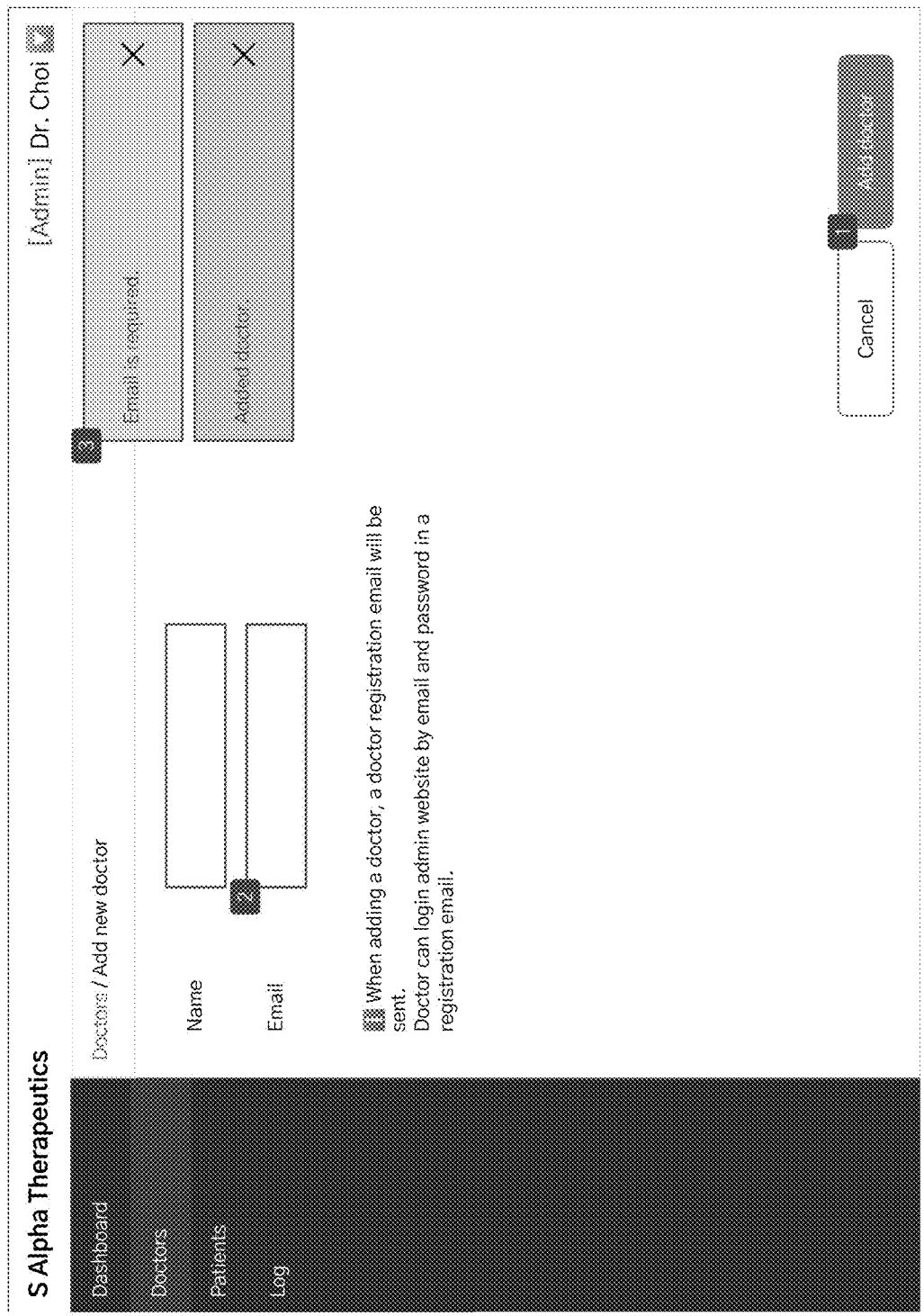
Figure 47E:
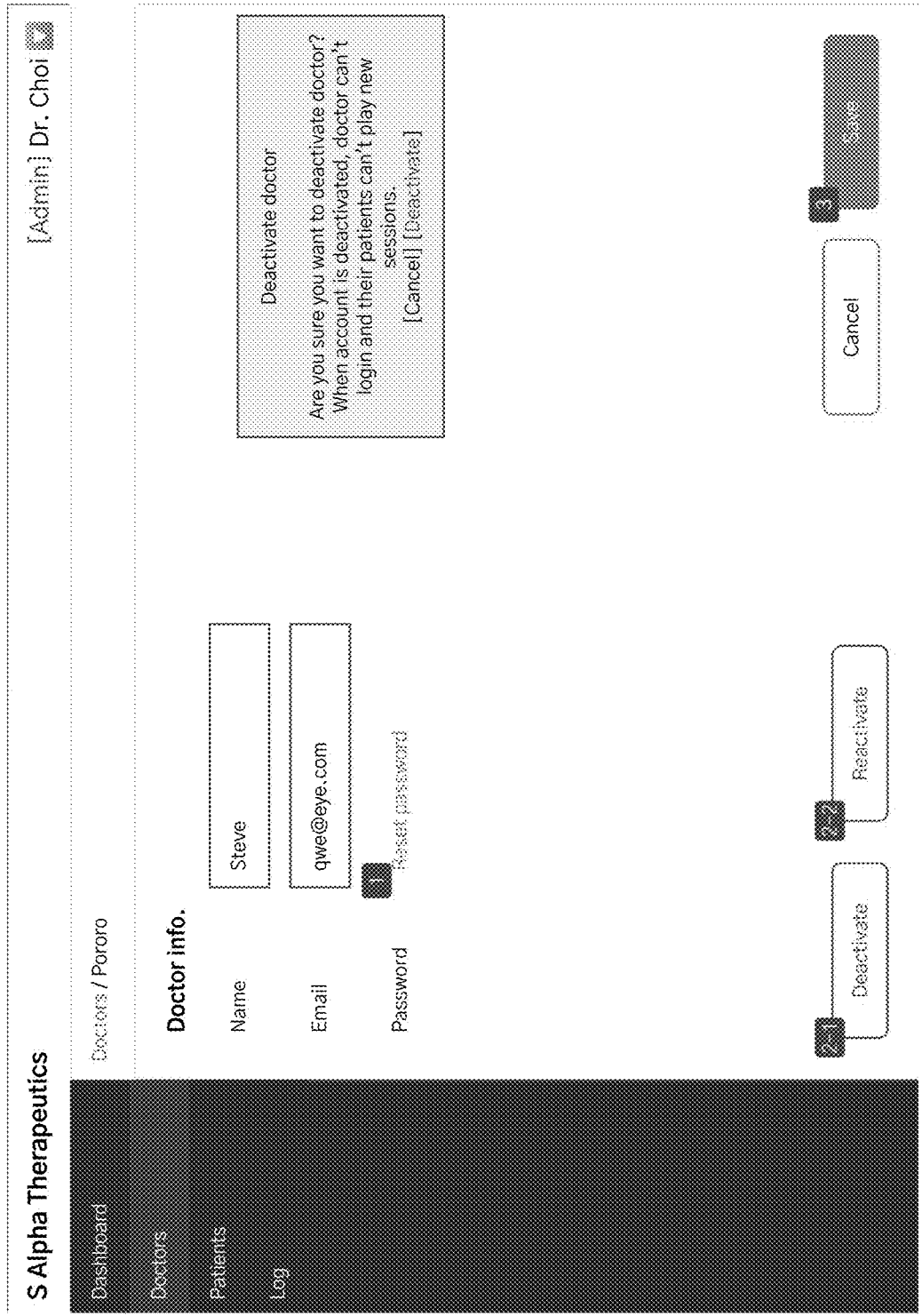
Figure 47F:
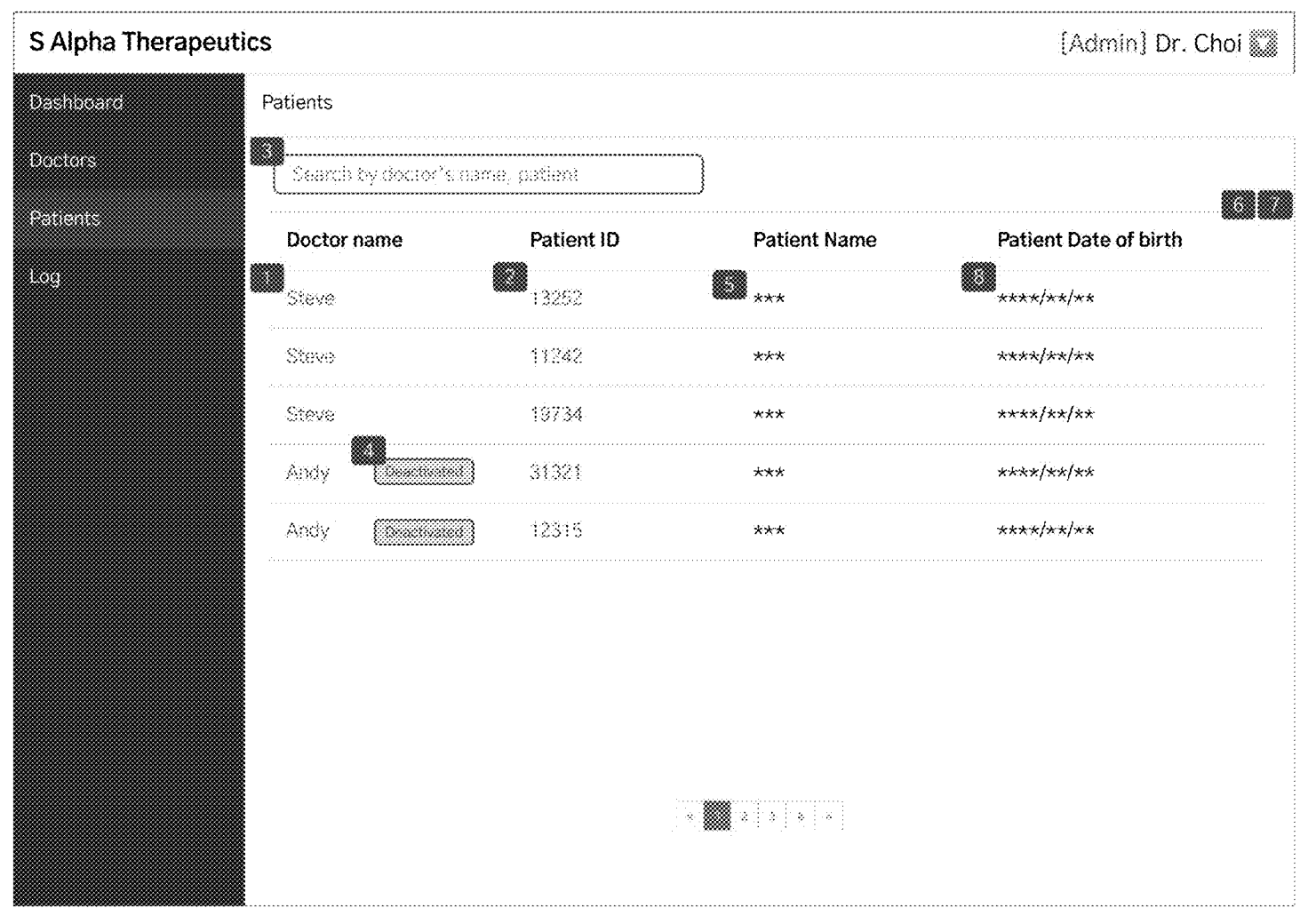
Figure 47G:
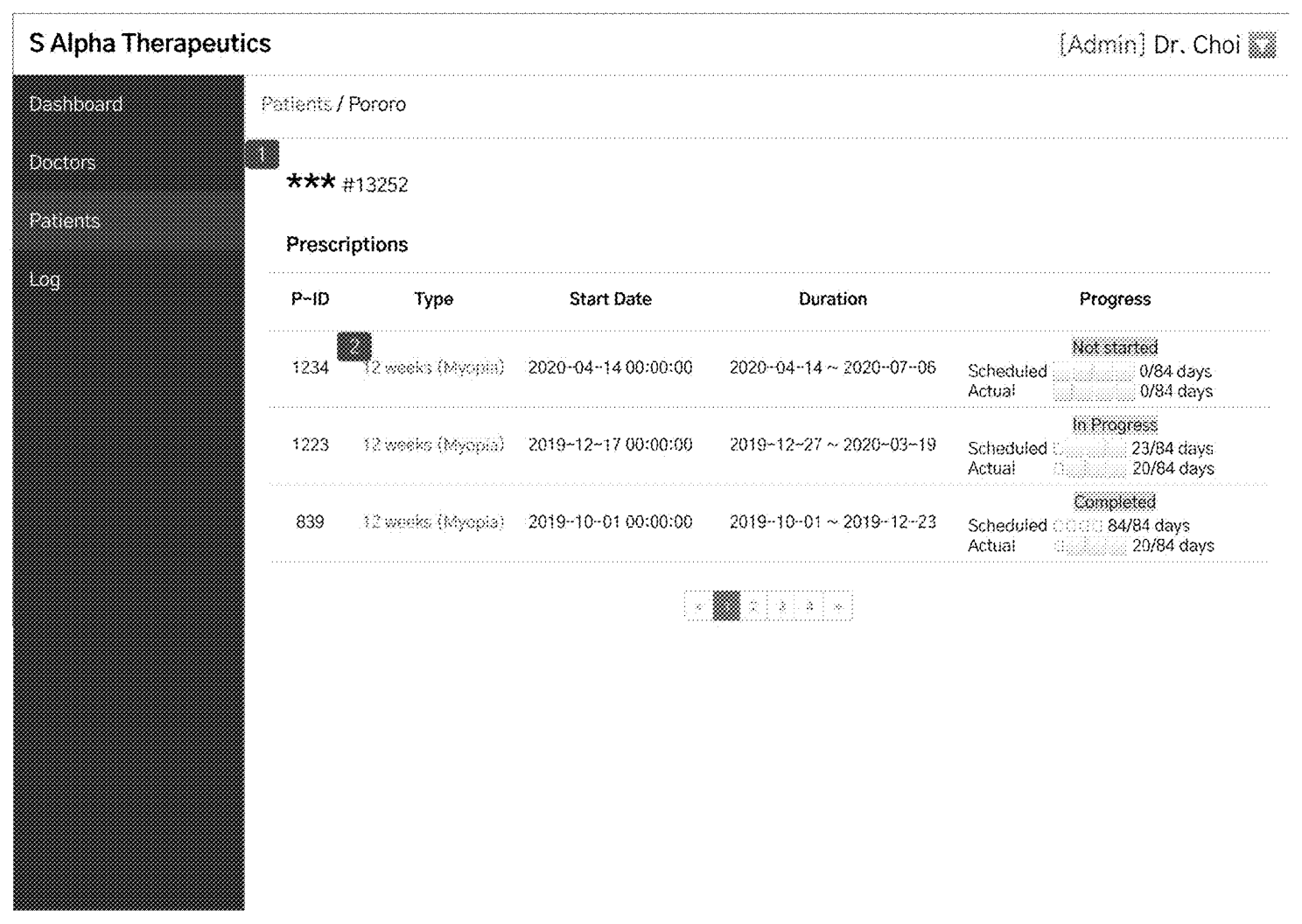
Figure 47H:
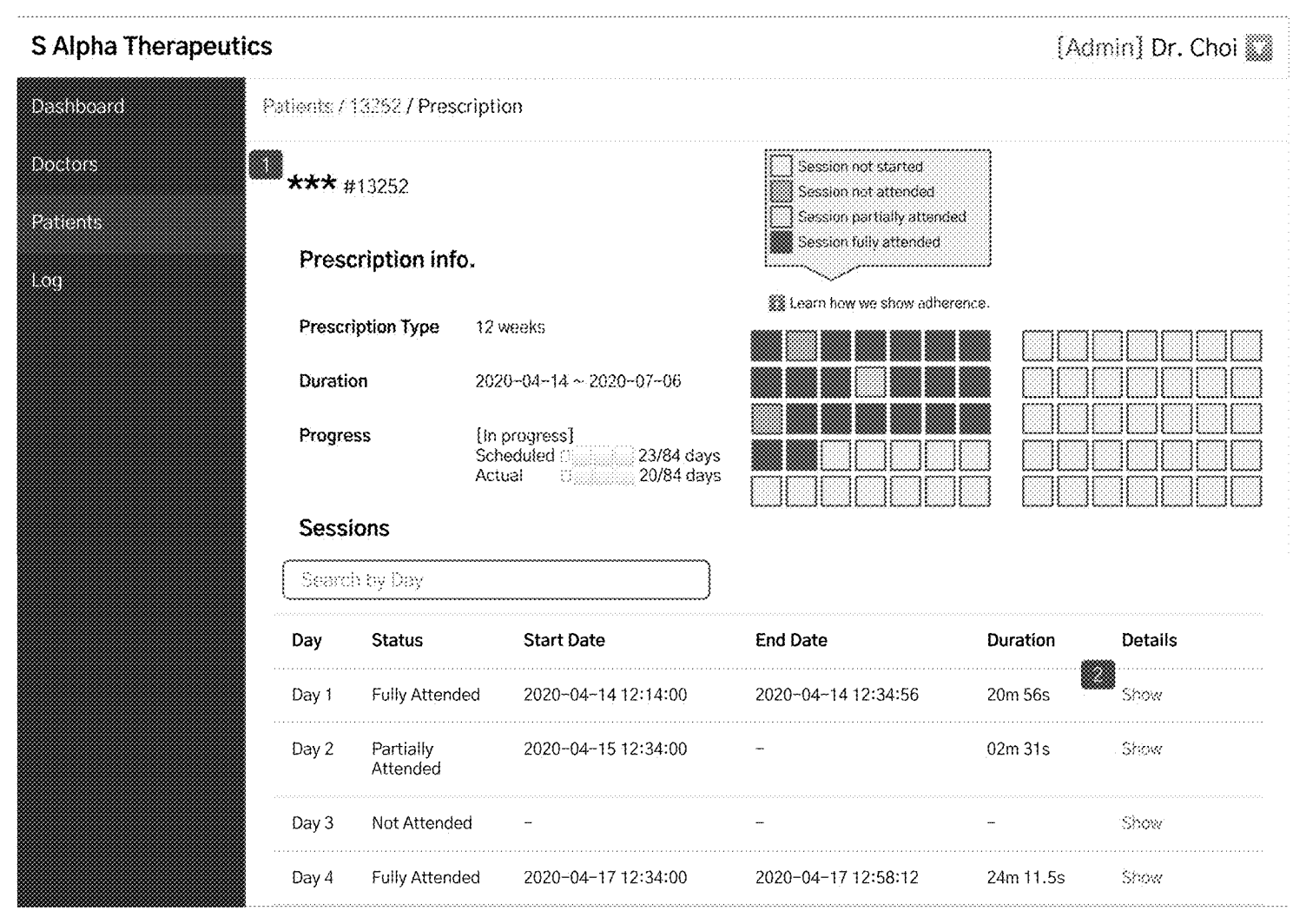
Figure 47I:
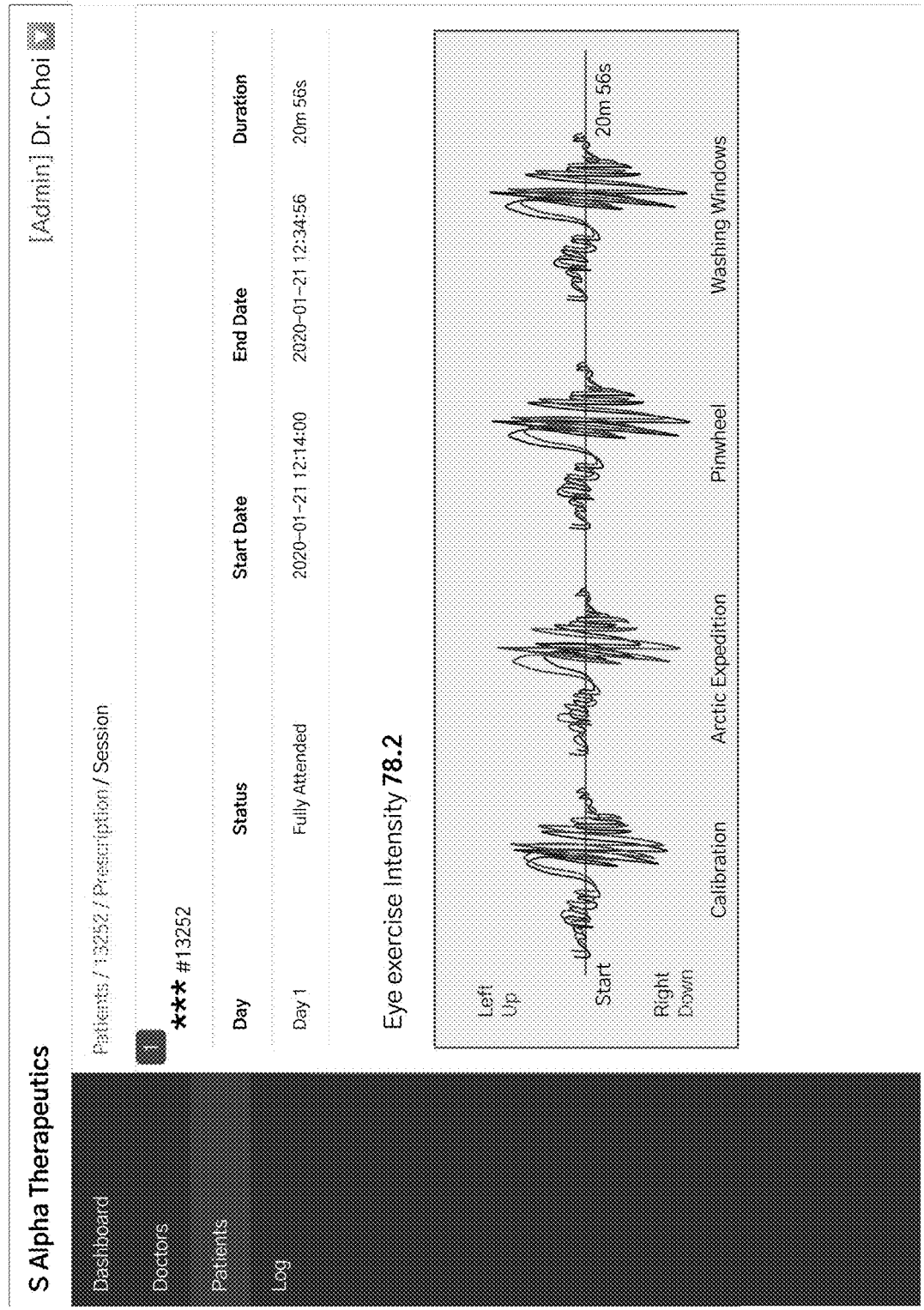

FIG. 47A depicts (A) a dashboard of an administrative portal. As shown, (1) shows the number of doctors. A graph may be used to show the number of doctors that have visited the digital application per day in the most recent 90 days, (2) The number of all patients associated with the any doctor's account. A graph may be used to show the number of patients who have opened the digital application for patient per day in the most recent 90 days. The number of patients in progress may also be viewed. A graph may be used to show the number of patients who have completed the daily sessions per day in the most recent 90 days. FIG. 47B depicts a doctor tab in an administrative portal, the doctor tab displaying a list of doctors. As shown, (1) is a search bar for searching for various doctors by name, email, etc., (2) shows a button for adding a new doctor, (3) is the doctor's ID, (4) is a button for viewing detailed doctor information, and (5) shows deactivated doctor accounts. FIG. 47C depicts a doctor tab in an administrative portal, the doctor tab displaying a list of patients being cared for by a given doctor, with patient-identifying information redacted (*). As shown, (1) is the doctor's account information, (2) is a button for editing the doctor's account information, (3) is a list of patients being cared for by the doctor, (4) is a list of patient ID numbers, (5) a link or button for sending the doctor a registration email, (6) a notification that the doctor's account has been deactivated, which only appears for deactivated accounts, and (7 and 8) redacted or de-identified patient information. FIG. 47D depicts a doctor tab in an administrative portal for adding a new doctor. FIG. 47E depicts a doctor tab in an administrative portal for editing information of an existing doctor, including activating or deactivating a doctor's account. FIG. 47F depicts a patient tab in an administrative portal that displays information for one or more patients, wherein sensitive information is redacted. FIG. 47G depicts a patient tab in an administrative portal that displays detailed patient or prescription information for a given patient. FIG. 47H depicts a patient tab in an administrative portal that displays detailed prescription information for a given patient. FIG. 47I depicts a patient tab in an administrative portal for viewing details (e.g., date, status, duration, results) of a given session for a given patient. FIG. 48 provides a table showing privileges for the doctors using the healthcare provider portal and the administrators using the administrative portal.

In some embodiments, the digital application further comprises a push alarm and/or push notifications for one or more of reminding the subject complete a digital therapeutic module and adjusting the light settings of the subject's environment. In some embodiments, the push alarm and/or push notification is activated to remind the subject to adjust the light settings such that the subject is exposed to sufficiently bright light at least 3 times per day.

A patient or subject treated by any of the methods, systems, or digital applications described herein may be of any age and may be an adult, infant or child, however the methods and systems of the present disclosure are particularly suitable for children. In some cases, the patient or subject is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 years old, or within a range therein (e.g., between 2 and 20 years old, between 20 and 40 years old, or between 40 and 90 years old). In some embodiments, the patient or subject is a child. In some embodiments, the patient or subject is a child, and is supervised by an adult when using the methods, systems, or digital applications of the present disclosure. In some embodiments, the patient or subject is less than about 20 years old, less than about 15 years old, less than about 10 years old, or less than about 5 years old.

In some embodiments, the digital apparatus comprises a digital instruction generation unit configured to generate digital therapeutic modules for treating myopia based on a mechanism of action (MOA) in and a therapeutic hypothesis for the myopia, generate digital instructions based on the digital therapeutic modules, and provide the digital instructions to the subject. In some embodiments, the digital apparats comprises an outcome collection unit configured to collect the subject's execution outcomes of the digital instructions. In some embodiments, the digital instruction generation unit generates the digital therapeutic modules based on neurohumoral factors related to the myopia onset. In some embodiments, the neurohumoral factors comprise insulin-like growth factor (IGF), cortisol, and dopamine.

In some embodiments, the digital instruction generation unit generates the digital therapeutic modules based on the inputs from the healthcare provider. In some embodiments, the digital instruction generation unit generates the digital therapeutic modules based on information received from the subject.

In some embodiments, the information is received from the subject comprises at least one of basal factors, medical information, and digital therapeutics literacy of the subject. In some embodiments, the basal factors including the subject's activity, heart rate, sleep, and diet (including nutrition and calories). In some embodiments, the medical information including the subject's electronic medical record (EMR), family history, genetic vulnerability, and genetic susceptibility. In some embodiments, the digital therapeutics literacy including the subject's accessibility, and technology adoption to the digital therapeutics and the apparatus.

In some embodiments, the digital instruction generation unit generates the digital therapeutic modules matching to imaginary parameters which correspond to the mechanism of action in and the therapeutic hypothesis for the myopia. In some embodiments, the imaginary parameters are deduced in relation to the subject's environment, behaviors, emotions, and cognition.

In some embodiments, the digital apparats comprises an outcome collection unit configured to collect the subject's execution outcomes of the digital instructions, and the outcome collection unit collects the execution outcomes of the digital instructions by monitoring the subject's adherence to the digital instructions or allowing the subject to directly input the subject's adherence to the digital instructions. In some embodiments, the generation of the digital instructions at the digital instruction generation unit and the collection of the subject's execution outcomes of the digital instructions at the outcome collection unit are repeatedly executed several times with multiple feedback loops. In some embodiments, the digital instruction generation unit generates the subject's digital instructions for this cycle based on the subject's digital instructions in the previous cycle and the execution outcome data on the subject's digital instructions in the previous cycle collected at the outcome collection unit.

FIG. 36 depicts screenshots shown at the completion of a single session, at the completion of all daily sessions, and at stop/start verification in a digital application of the present disclosure. As shown, (1) a button to continue on the next session, (2) a button to move onto the home screen. If it is the last day of the prescribed duration move to screen 3.1.3, if not, 3.1.2 (see, e.g., FIG. 23). Session Stop Verification Pop-up appears when taps the Home button on the upper left while executing the session.

Figure 1B:
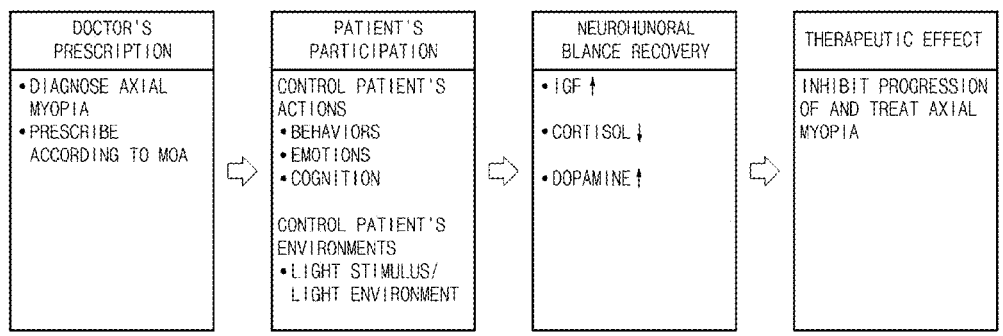
FIG. 1B is a diagram showing a therapeutic hypothesis for the axial myopia proposed in the present disclosure.
Figure 1C:
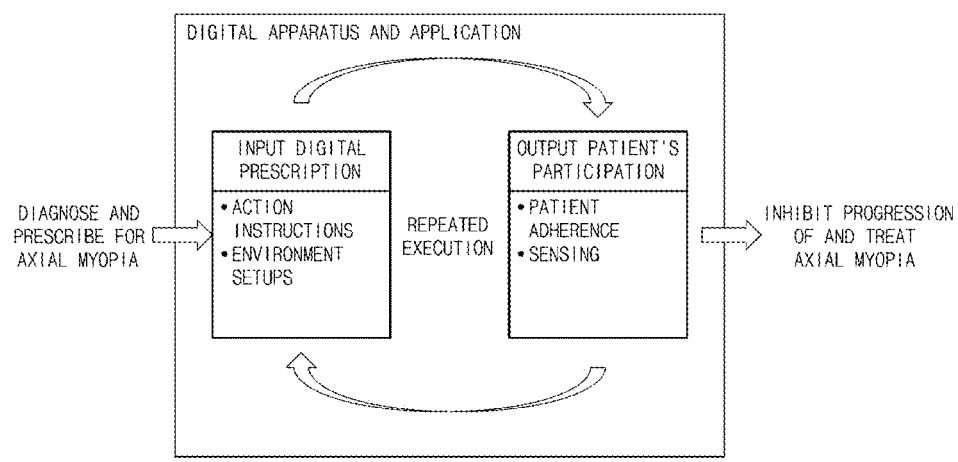
FIG. 1C is a diagram showing a digital therapeutic hypothesis for axial myopia proposed in the present disclosure.

FIG. 1A is a diagram showing a mechanism of action in axial myopia in the childhood/adolescence stages proposed in the present disclosure, FIG. 1B is a diagram showing a therapeutic hypothesis for the axial myopia proposed in the present disclosure, and FIG. 1C is a diagram showing a digital therapeutic hypothesis for axial myopia proposed in the present disclosure.

A digital apparatus and an application for inhibiting progression of and treating myopia according to the present disclosure as will be described below are realized based on the mechanism of action and therapeutic hypothesis deduced through the literature search and expert reviews of clinical trial articles on axial myopia in childhood/adolescence stages.

Generally speaking, disease therapy is carried out by analyzing a certain disease in terms of pathophysiological functions and dispositions in order to determine a start point, a progression point, and an end point for the disease. Also, an indication of the disease is defined by characterization of the corresponding disease and statistical analysis of the disease. Also, patient's physiological factors, especially neurohumoral factors, which correspond to the verified indications, are analyzed, and the patient's neurohumoral factors are restricted a narrow extent associated with the disease to deduce a mechanism of action.

Next, a therapeutic hypothesis, in which the corresponding disease is treated by controlling actions and environments directly associated with regulation of the corresponding neurohumoral factors associated with the disease, is deduced. To realize this therapeutic hypothesis into digital therapeutics, a digital therapeutic hypothesis for achieving a therapeutic effect through repeated digital instruction and execution, which are associated with the "control of patient's action/environment→regulation of neurohumoral factors, is proposed. The digital therapeutic hypothesis of the present disclosure is realized as a digital apparatus and an application is realized as a digital apparatus and an application configured to present changes in patient's actions (including behavioral, emotional, and cognitive areas), improvement of patient's environment, and patient's participation in the form of specific instructions and collect and analyze execution of the specific instructions.

Literature search for the clinical trials as described above may be executed through meta-analysis and data mining, and the clinical specialist's feedbacks and deep reviews may be applied in each analysis step. Basically, the present disclosure encompasses extracting a mechanism of action in and a therapeutic hypothesis for axial myopia using the procedure as described above, and regulating the neurohumoral factors based on these results to provide a digital apparatus and an application as digital therapeutics for inhibiting progression of and treating axial myopia.

However, a method of extracting a mechanism of action in and a therapeutic hypothesis for axial myopia according to the present disclosure is not limited to the methods as described above. In addition, mechanisms of action in and therapeutic hypotheses for diseases may be extracted using various methods.

Referring to FIG. 1A, various risk factors in the childhood/adolescence stages, for example, near working, education, race, genetics, and other factors (premature birth, diet, light exposure, birth season, increased intraocular pressure, etc.) may cause the imbalance of neurohumoral factors (which are related to the myopia onset) in the childhood/adolescence stages. As a result, proteoglycans are abnormally produced in the sclera around the eye due to IGF, cortisol, and dopamine dysregulation, which results in axial myopia developing due to abnormal growth of the optical axis.

Referring to FIG. 1B, the therapeutic hypothesis for axial myopia according to the present disclosure includes inhibition of progression of and treatment of axial myopia by restoring the balance of neurohumoral factors through the patient's actions (including behavioral, emotional, and cognitive areas) and environment, and the patient's participation.

Referring to FIG. 1C, the digital therapeutic hypothesis for axial myopia is realized as a digital apparatus and an application configured to present changes in patient's actions, improvement of patient's environment, and patient's participation in the form of specific instructions and collect and analyze execution of the specific instructions. When the digital therapeutics of the present disclosure are used, the imbalance of neurohumoral factors for axial myopic patients in the childhood/adolescence stages may be corrected through the digital inputs (instructions) and outputs (execution) to achieve inhibition of progression of and treatment of axial myopia.

Meanwhile, the mechanism of action in and the therapeutic hypothesis for axial myopia are described with reference to FIGS. 1A and 1B, but the present disclosure is not limited thereto. For example, the methodology of the present disclosure may be applied to all types of myopia, and any other diseases.

Also, although the insulin-like growth factor (IGF), cortisol, and dopamine are described as the neurohumoral factors as shown in FIGS. 1A and 1B, it should be understood that the description of the neurohumoral factors is given by way of illustration only, and are not intended to be limiting in all aspects of the mechanism of action in and the therapeutic hypothesis for myopia according to the present disclosure. Accordingly, all the neurohumoral factors having an influence on the myopia may be considered.

Figure 2:
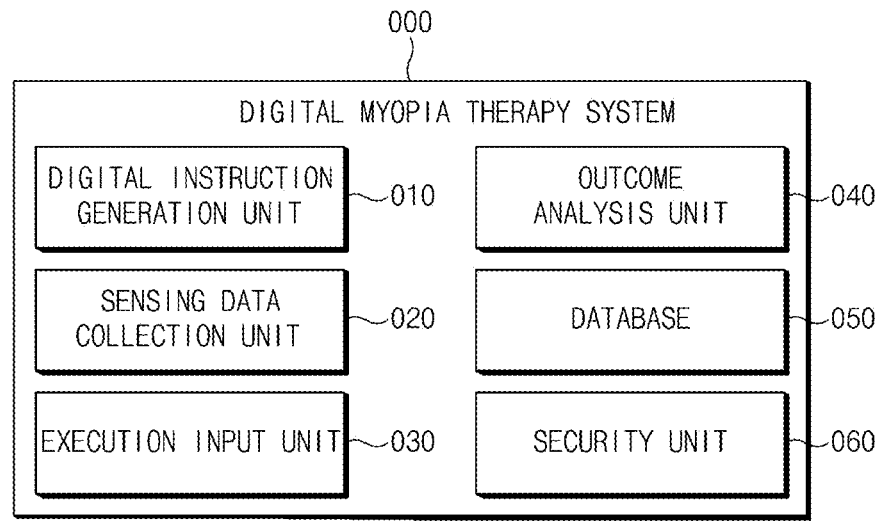
FIG. 2 is a block diagram showing a configuration of a digital apparatus for treating myopia according to one embodiment of the present disclosure.

FIG. 2 is a block diagram showing a configuration of the digital apparatus for treating myopia according to one embodiment of the present disclosure.

Referring to FIG. 2, a digital system 000 for treating myopia according to one embodiment of the present disclosure may include a digital instruction generation unit 010, a sensing data collection unit 020, an execution input unit 030, an outcome analysis unit 040, a database 050, and a security unit 060.

Based on the mechanism of action in and the therapeutic hypothesis and digital therapeutic hypothesis for axial myopia in the childhood/adolescence stages, a doctor (a second user) may prescribe digital therapeutics, which are realized in a digital apparatus and an application for treating myopia, for the corresponding patient. In this case, the digital instruction generation unit 010 is a device configured to provide a prescription of the digital therapeutics to a patient as a specific behavioral instruction that the patient may execute based on the interaction between the neurohumoral factors for myopia and the patient's behaviors/environments. For example, the neurohumoral factors may include IGF, cortisol, dopamine, and the like, but the present disclosure is not limited thereto. For example, all types of neurohumoral factors that may cause myopia may be considered.

The digital instruction generation unit 010 may generate digital instructions based on the inputs from the doctor. In this case, the digital instruction generation unit 010 may generate digital instructions based on information collected by the doctor when diagnosing a patient. Also, the digital instruction generation unit 010 may generate digital instructions based on the information received from the patient. For example, the information received from the patient may include the patient's basal factors, medical information, and digital therapeutics literacy. In this case, the basal factors may include amount of the patient's activity, heart rates, sleep, meals (nutrition and calories), and the like. The medical information may include the patient's electronic medical record (EMR), family history, genetic vulnerability, genetic susceptibility, and the like. The digital therapeutics literacy may include the patient's accessibility and an acceptance posture to the digital therapy instructions and the apparatus, and the like.

The digital instruction generation unit 010 may reflect the mechanism of action in and the therapeutic hypothesis for myopia in order to utilize imaginary parameters and generate a digital module. In this case, the imaginary parameters may be deduced in term of the patient's environments, behaviors, emotions, and cognition. In this regard, the imaginary parameters will be described in detail as shown in FIG. 5.

The digital instruction generation unit 010 generates digital instructions particularly designed to allow a patient to have a therapeutic effect, and provides the instructions to the patient. For example, the digital instruction generation unit 010 may provide light stimuli under a bright light environment, and simultaneously generate specific digital instructions in each of digital therapeutic modules.

The sensing data collection unit 020 and the execution input unit 030 may collect the patient's execution outcomes of the digital instructions provided at the digital instruction generation unit 010. Specifically, the sensing data collection unit 020 configured to sense the patient's adherence to the digital instructions and the execution input unit 030 configured to allow a patient to directly input the execution outcomes of the digital instructions are included, and thus serve to output the patient's execution outcomes of the digital instructions.

The outcome analysis unit 040 may collect the patient's behavior adherence or participation in predetermined periods and report the patient's behavior adherence or participation to external systems. Therefore, a doctor may continue to monitor an execution course of the digital instructions through the application even when a patient does not directly visit a hospital.

The database 050 may store the mechanism of action in myopia, the therapeutic hypothesis for myopia, the digital instructions provided to the user, and the user's execution outcome data. FIG. 2 shows that the database 050 is included in the digital apparatus 000 for treating myopia. However, the database 050 may be provided in an external server.

Meanwhile, a series of loops including inputting the digital instructions at the digital instruction generation unit 010, outputting the patient's execution outcomes of the digital instructions at the sensing data collection unit 020/execution input unit 030, and evaluating the execution outcomes at the outcome analysis unit 040 may be repeatedly executed several times. In this case, the digital instruction generation unit 010 may generate patient-customized digital instructions for this cycle by reflecting the patient's digital instructions provided in the previous cycle and output values, and the evaluation.

As described above, according to the digital therapy apparatus for inhibiting progression of and treating axial myopia according to the present disclosure, the myopia therapy whose reliability may be ensured is possible by deducing the mechanism of action in axial myopia and the therapeutic hypothesis and digital therapeutic hypothesis for axial myopia in consideration of the neurohumoral factors for axial myopia, presenting the setups of light stimulus environments suitable for the patient and digital instructions for treating axial myopia based on the mechanism of action and the therapeutic hypotheses, and collecting and analyzing execution of specific instructions.

Figure 3:
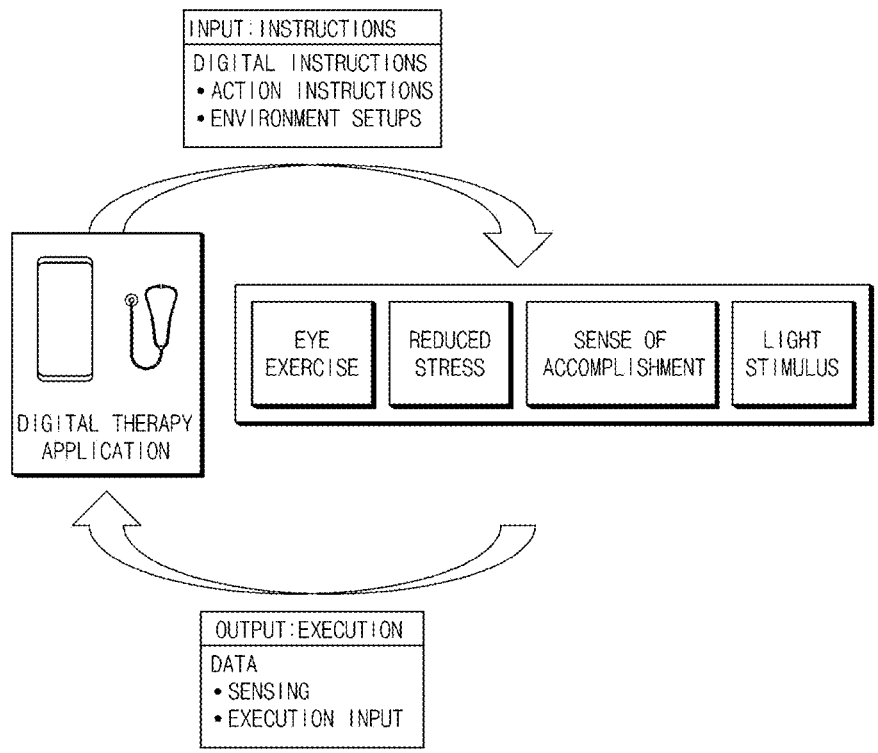
FIG. 3 is a diagram showing input and output loops of a digital application for treating myopia according to one embodiment of the present disclosure.

FIG. 3 is a diagram showing input and output loops of the digital application for treating myopia according to one embodiment of the present disclosure.

Referring to FIG. 3, the digital application for treating myopia according to one embodiment of the present disclosure may input the corresponding digital prescription for a patient in the form of instructions, and may output execution outcomes of the corresponding digital instructions.

The digital instructions provided to the patient may include specific action instructions for behaviors, emotions, cognition, and the like, and control of the patient's light environments. As shown in FIG. 3, the digital instructions may include eye exercise, reduced stress, a sense of accomplishment, light stimulus, and the like. However, the digital instructions are given by way of illustration only, and are not intended to be limiting to the digital instruction according to the present disclosure.

The patient's execution outcomes of the digital instructions consist of 1) log-in/log-out information for instructions and execution, 2) adherence information sensed as passive data such as eye exercise, heart rates associated with the stress, a change in oxygen saturation, and the like, and 3) directly input information on the patient's execution outcomes.

Figure 4:
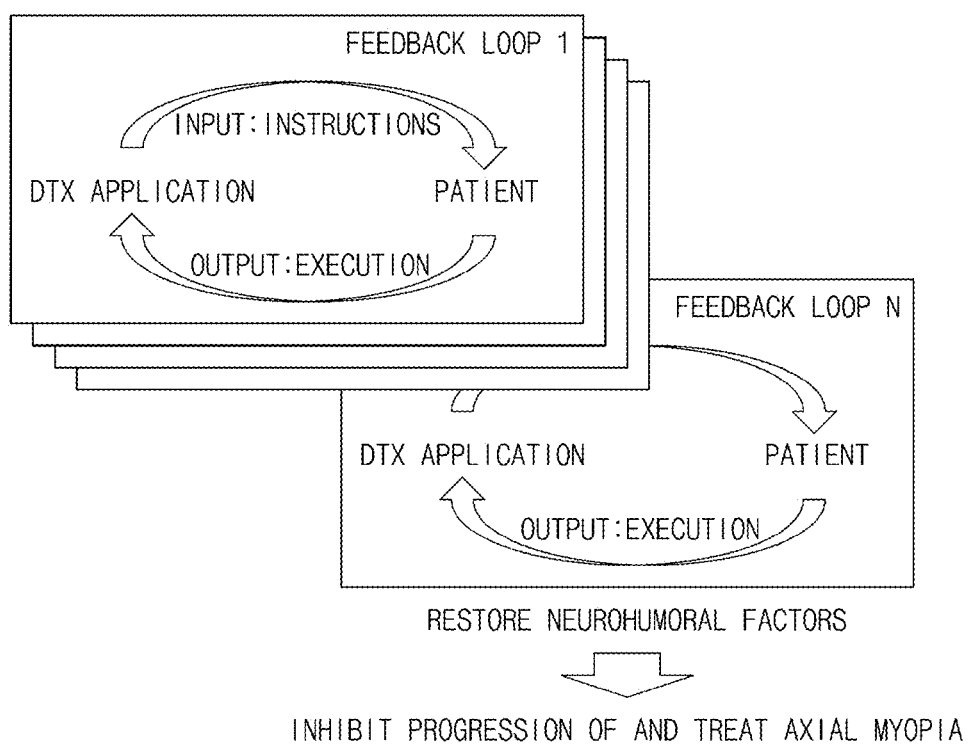
FIG. 4 is a diagram showing a feedback loop for a digital apparatus and an application for treating myopia according to one embodiment of the present disclosure.

FIG. 4 is a diagram showing a feedback loop for the digital apparatus and the application for treating myopia according to one embodiment of the present disclosure.

Referring to FIG. 4, the inhibition of the progression of and the treatment of axial myopia are shown to be achieved by repeatedly executing the aforementioned single feedback loop of FIG. 3 several times to regulate the neurohumoral factors.

In the case of the axial myopia, the digital therapy and observation take a short period of 10 weeks to the whole period of the childhood/adolescence stages to treat the axial myopia due to the pathological characteristics of the axial myopia. Due to these characteristics, inhibitory and therapeutic effects on progression of the axial myopia may be more effectively achieved by gradual improvement of an instruction-execution cycle in the feedback loop, compared to the simply repeated instruction-execution cycle during the corresponding course of therapy.

For example, the digital instructions and the execution outcomes for the first cycle are given as input values and output values in a single loop, but new digital instructions may be generated by reflecting input values and output values generated in this loop using a feedback process of the loop to adjust the input for the next loop when the feedback loop is executed N times. This feedback loop may be repeated to deduce patient-customized digital instructions and maximize a therapeutic effect at the same time.

As such, in the digital apparatus and the application for treating myopia according to one embodiment of the present disclosure, the patient's digital instructions provided in the previous cycle (for example, a N–$1^{st}$ cycle), and the data on instruction execution outcomes may be used to calculate the patient's digital instructions and execution outcomes in this cycle (for example, a $N^{th}$ cycle). That is, the digital instructions in the next loop may be generated based on the patient's digital instructions and execution outcomes of the digital instructions calculated in the previous loop. In this case, various algorithms and statistical models may be used for the feedback process, when necessary.

As described above, in the digital apparatus and the application for treating myopia according to one embodiment of the present disclosure, it is possible to optimize the patient-customized digital instructions suitable for the patient through the rapid feedback loop.

Figure 5A:
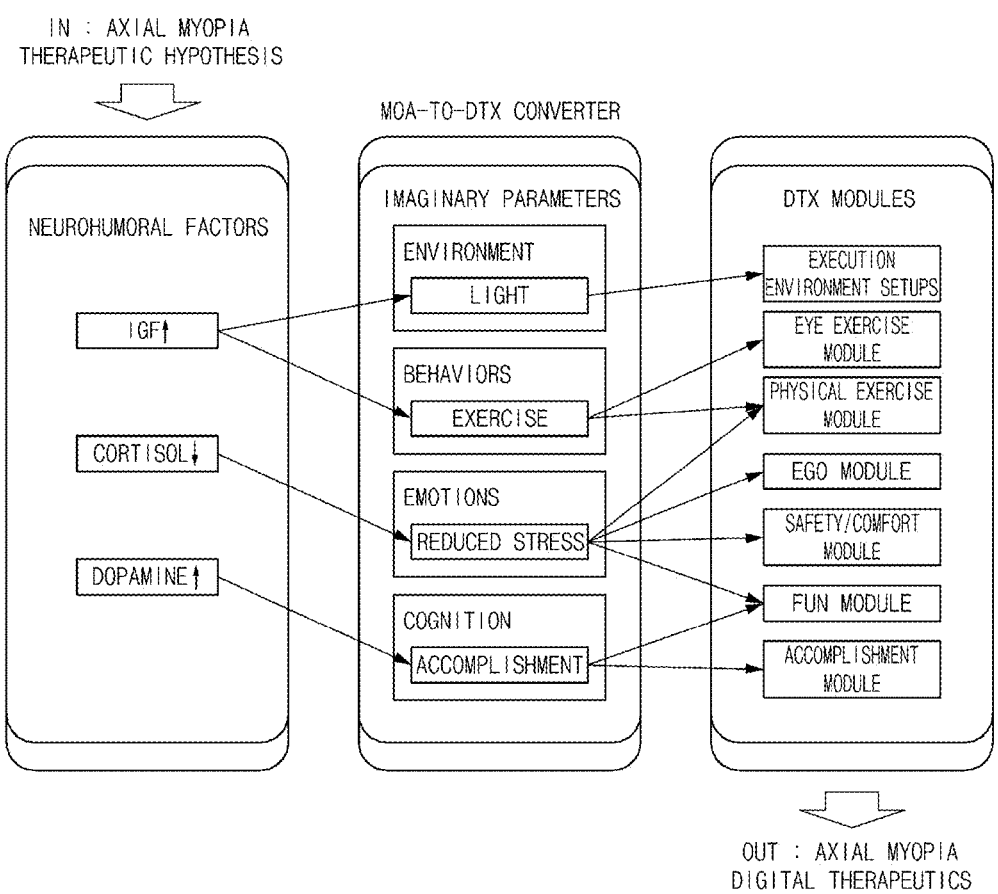
FIG. 5A is a diagram showing a module design for realizing a digital therapy in the digital apparatus and the application for treating myopia according to one embodiment of the present disclosure.
Figure 5B:
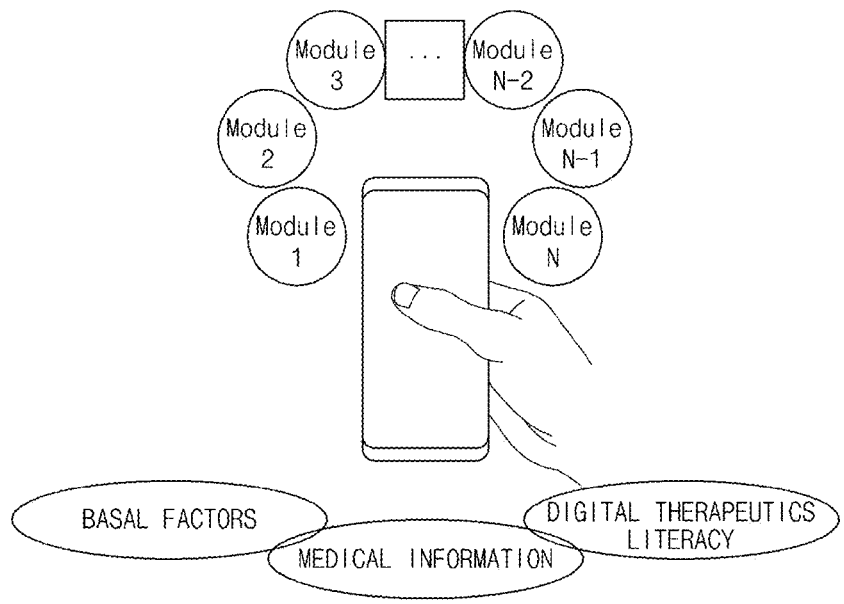
FIG. 5B is a diagram showing a background factors supporting the digital apparatus and the application for treating myopia according to one embodiment of the present disclosure.

FIG. 5A is a diagram showing a module design for realizing a digital therapy in the digital apparatus and the application for treating myopia according to one embodiment of the present disclosure, FIG. 5B is a diagram showing a background factors supporting the digital apparatus and the application for treating myopia according to one embodiment of the present disclosure As shown in FIG. 5A, when the therapeutic hypothesis based on the mechanism of action in myopia is created, targeted neurohumoral factors (for example, IGF, cortisol, dopamine, etc.) may be deduced. Imaginary parameters may be utilized to allow specific instructions to correspond to the regulation of these neurohumoral factors. Modules required to treat myopia was deduced using the "neurohumoral factor-imaginary parameter-module" interrelation. Each of the modules will be described in the form of modular instructions in further detail with reference to FIG. 7 as will be described below. In this case, each of the modules is in fact a basic design unit for digital therapeutics realized in the digital apparatus or the application, and is a collection of specific instructions.

Specifically, referring to FIG. 5A, the neurohumoral factors deduced based on the mechanism of action in and the therapeutic hypothesis for axial myopia may be IGF, cortisol (or TGF-beta influenced by the cortisol), and dopamine (or GABA agonist/antagonists, glucagon). To treat myopia, the neurohumoral factors should be regulated in the corresponding age groups to promote secretion of IGF and dopamine having an influence on the eye development and inhibit secretion of cortisol.

The control of each of the neurohumoral factors corresponds to the digital therapeutics module using environments (light), behaviors (exercise), emotions (reduced stress), and cognition (a sense of accomplishment) as imaginary parameters. Specific digital instructions for each module are generated based on the converted modules. In this case, the digital instructions may include execution environment setups and modules (e.g., eye exercise, gymnastics, ego, safety/comfort, fun, and accomplishment modules), which may be output by monitoring. However, the modules are given by way of illustration only, and are not intended to be limiting to the modules according to the present disclosure.

Meanwhile, referring to FIG. 5B, the background factors may be considered together in the design of the modules in the digital apparatus and the application for treating myopia according to one embodiment of the present disclosure.

In this case, the background factors are elements necessary for correction of clinical trial outcomes during verification of the clinical effectiveness of digital myopia therapy according to the present disclosure. Specifically, in the background factors shown in FIG. 5B, the basal factors may include activity, heart rates, sleep, meals (nutrition and calories), and the like, the medical information may include EMR, family history, genetic vulnerability, and susceptibility, and the like, which have been written when a patient visited a hospital, and the digital therapeutics literacy may include the patient's accessibility to the digital therapy instructions and the apparatus, and an acceptance posture.

Figure 6:
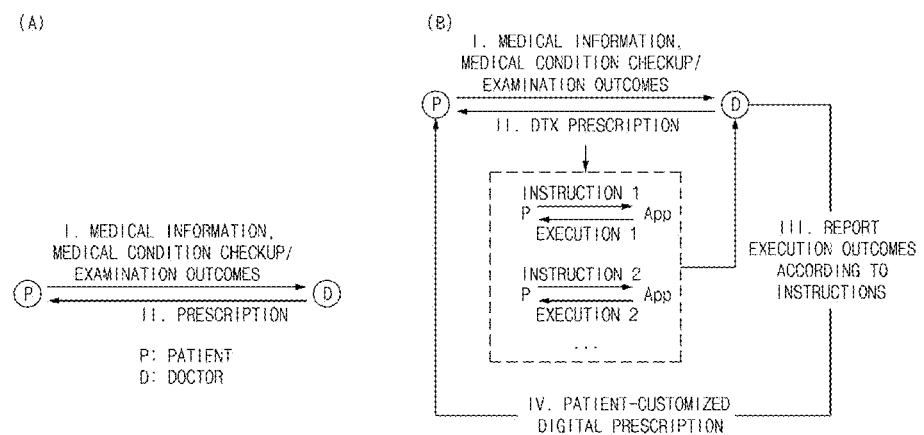
FIG. 6 is a diagram showing a method of assigning a patient-customized digital prescription using the digital apparatus and the application for treating myopia according to one embodiment of the present disclosure.

FIG. 6 is a diagram showing a method of assigning a patient-customized digital prescription using the digital apparatus and the application for treating myopia according to one embodiment of the present disclosure.

FIG. 6(A) show a prescription procedure for routine medical condition checkup of a patient by a doctor, and FIG. 6(B) show a method of allowing a doctor to assign a patient-customized digital prescription based on the analysis of a plurality of digital instructions and execution outcomes of the digital instructions.

In this way, when the digital apparatus and the application for treating myopia according to one embodiment of the present disclosure are used, the doctor may check the patient's instructions and execution outcomes for a given period and adjust the types of modules for treating myopia, and the instructions for each module in a patient-customized manner, as shown in FIG. 6(B).

FIG. 7A shows execution environment setups according to one embodiment of the present disclosure, and FIGS. 7B to 7G show examples of specific instructions for each module, and methods of collecting output data according to one embodiment of the present disclosure.

For digital therapy of axial myopia, because the patient's persistent participation is generally essential for 10 weeks or more, it is far more important that adolescent children have fun in digital therapy and voluntarily participate in the digital therapy. In this context, the modules may be configured by adding game elements to each module. In the digital apparatus and the application for treating myopia, which have been realized to relieve and treat axial myopia, as will be described below, each module is a basic design unit and is a collection of specific instructions.

Referring to FIG. 7A, specific examples of instructions for execution environment setups, and a method of collecting output data are shown. In this case, the execution environment setups may be included as part of the configuration of the digital instruction generation unit 010 shown in FIG. 2.

Specifically, the execution environment setups include setup of brightness of an execution environment using an illuminance sensor, and other modules are executed under a set light environment.

In general, sunlight is closely related to the eye health. The same strong light stimulation as in exposure to direct sunlight acts in nerve cells of the retina to promote secretion of dopamine, thereby inducing synthesis of proteoglycans. This is a factor essential for normally adjusting an axial length of the eye.

As described above, the illuminance under a current environment may be measured using an illuminance sensor to provide light stimuli to a patient, an alarm of a current light environment may be provided to brightly control an environment at which a patient participates in digital therapy.

Referring to FIG. 7B, specific examples of instructions for an eye exercise module, and a method of collecting output data are shown. In this case, the may be included as part of the configuration of the digital instruction generation unit 010 shown in FIG. 2.

The digital instructions for eye exercise include controlling the patient's eye exercise, biofeedbacks, eyeball-related behaviors, and the like, and promote secretion of IGF in oculomotor muscles. Specifically, behavioral instructions for the eye exercise module may monitor the patient's adherence using eye tracking technology such as eye exercise, eye blinking, remote staring, eye closing, and the like. However, a collection of the execution outcomes for the eye exercise module is not limited to the eye tracking technology, and include directly inputting the execution outcomes of the instructions by the patient.

Referring to FIG. 7C, specific examples of instructions for a physical exercise module, and a method of collecting output data are shown. In this case, the physical exercise module may be included as part of the configuration of the digital instruction generation unit 010 shown in FIG. 2. The physical exercise module includes slow and comfortable physical exercise, and abdominal exercise, and may be composed of a series of behavioral instructions configured to reduce stress through breaks, relaxation, deep breathing, and the like in order to inhibit secretion of cortisol.

Specifically, the behavioral instructions for the physical exercise module include behavioral instructions such as relaxation exercise, deep breathing, meditation, eye massage, and the like. Also, the behavioral instructions include a method of collecting the execution outcomes of the behavioral instructions at the sensing data collection unit 020 using a biofeedback apparatus (for measuring EEG, ECG, EMG, EDG, etc.) or a general-purpose sensor (for measuring activity, HR, etc.), or a method of allowing a patient to directly input the execution outcomes using the execution input unit 030. The behavioral instructions of the present disclosure are composed based on a behavior therapy method which is widely used to relieve stress of children in the child psychiatry.

In general, the progression of myopia is closely related to the course of adolescence. In particular, there might be a great deal of variation among the adolescent children in this stage, depending on the age, gender, character, and preference of the children. To cover these deviations, it is desirable that the digital instructions for each module are presented in a customized manner according to the individual characteristics of each patient. In particular, instructions requiring the mutual communication (for example, conversation) with an application may be developed in combination with big data analysis and artificial intelligence analysis.

Referring to FIG. 7D, specific examples of instructions for an ego module, and a method of collecting output data are shown. In this case, the ego module may be included as part of the configuration of the digital instruction generation unit 010 shown in FIG. 2.

Specifically, the instructions for the ego module aim to serve to increase the adolescents' self-esteem and relive the stress. To do this, the instructions for the ego module may, for example, include instructions such as conversation, drawing, meditation, diary writing, making his/her own safe space (safety place instructions), his/her favorites (places, time, seasons, colors, foods, humans, etc.), his/her own bucket lists, choosing places to travel and planning for travel, and the like. These instructions are composed based on a psychotherapy which has been widely used in the child psychiatry to increase the self-esteem and relive the stress of children or adolescents.

Referring to FIG. 7E, specific examples of instructions for a safety/comfort module, and a method of collecting output data are shown. In this case, the safety/comfort module may be included as part of the configuration of the digital instruction generation unit 010 shown in FIG. 2.

Specifically, the instructions for the safety/comfort module aim to serve as ventilation to reduce the adolescents' stress. To do this, the instructions for the safety/comfort module may, for example, include instructions such as chatting, expression (writing, singing, drawing), leaving unpleasant emotions in an animational aspect (trash may instructions), and the like. These instructions are composed based on a psychotherapy which has been widely used in the child psychiatry to increase the self-esteem and relive the stress of children or adolescents.

Referring to FIG. 7F, specific examples of instructions for a fun module, and a method of collecting output data are shown. In this case, the fun module may be included as part of the configuration of the digital instruction generation unit 010 shown in FIG. 2.

Specifically, the instructions for the fun module are instructions that allow a patient to use an application and have fun, may be compose of various contents such as music, games, or videos, depending on the adolescent characteristics. Also, fun instructions in the fun module also aim to improve the patient's persistent participation in the digital therapy.

Referring to FIG. 7G, specific examples of instructions for an accomplishment module, and a method of collecting output data are shown. In this case, the accomplishment module may be included as part of the configuration of the digital instruction generation unit 010 shown in FIG. 2.

Specifically, the instructions for the accomplishment module may include instructions that promote secretion of dopamine through senses of accomplishment such as the patient's task execution and completion. Here, the task accomplishment instructions are instructions that allow a patient to feel a sense of accomplishment when a given task is accomplished, and thus may include games whose tasks may be updated over a patient's participation duration and which may induce the patient's voluntary participation. For example, a specific format of the game may be composed of various times such as learning, hidden or difference pictorial puzzles, quizzes, and the like.

In particular, some instructions realized in the form of quizzes at the accomplishment module may be expected to have an additional effect of improving the patient's health information literacy and digital therapeutics literacy. Such improvement of the health information and digital therapeutics literacy is an element essential for the patient's persistent participation and execution in the therapy.

As mentioned above, the digital therapy according to the present disclosure requires not less than 10 weeks of the patient's participation. During this period, sincerely executing the instructions for the aforementioned modules makes it possible to form compliment instructions in the accomplishment module so that a patient feels a sense of accomplishment. For the compliment instructions, the patient's active participation in the therapy may be fed back as a sense of accomplishment based on the reliance and compensation between the patient and a guardian and between the patient and the doctor.

The digital instruction shown above in FIG. 7B to FIG. 7G are given by way of illustration only, and are not intended to limit the present disclosure. For example, the digital instructions provided to the patient may be set in various manners, when necessary.

Figure 8:
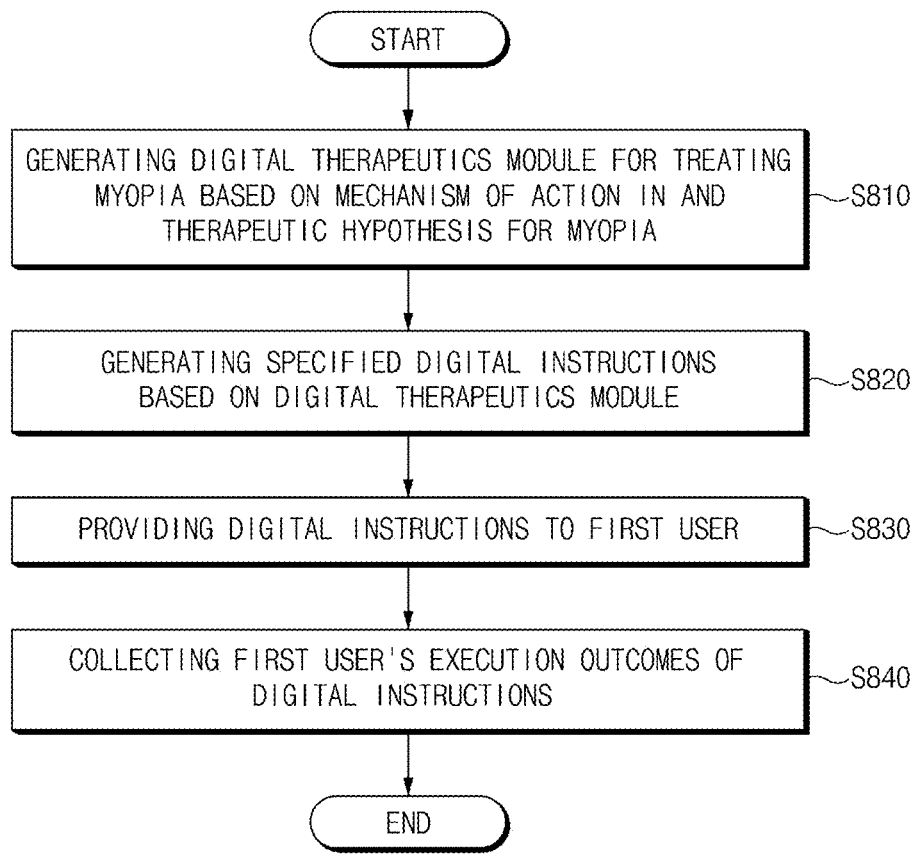
FIG. 8 is a flowchart illustrating operations in a digital application for treating myopia according to one embodiment of the present disclosure.

FIG. 8 is a flowchart illustrating operations in the digital application for treating myopia according to one embodiment of the present disclosure.

Referring to FIG. 8, the digital application for treating myopia according to one embodiment of the present disclosure may first generate a digital therapeutics module for treating myopia based on the mechanism of action in and the therapeutic hypothesis for myopia (S810). In this case, in S810, the digital therapeutics module may be generated based on the neurohumoral factors (for example, IGF, cortisol, dopamine, etc.) for myopia.

Meanwhile, in S810, the digital therapeutics module may be generated based on the inputs from the doctor. In this case, a digital therapeutics module may be generated based on the information collected by the doctor when diagnosing a patient, and the prescription outcomes recorded based on the information. Also, in S810, the digital therapeutics module may be generated based on the information (for example, basal factors, medical information, digital therapeutics literacy, etc.) received from the patient.

Next, in S820, specified digital instructions may be generated based on the digital therapeutics module. S820 may generate a digital therapeutics module by applying imaginary parameters about the patient's environments, behaviors, emotions, and cognition to the mechanism of action in and the therapeutic hypothesis for myopia. This digital therapeutics module is described with reference to FIG. 5, and thus description thereof will be omitted.

In this case, the digital instructions may be generated for at least one of light environment setup, eye exercise, physical exercise, ego, safety/comfort, fun, and accomplishment modules. Description of the execution environment setups and the specific digital instructions for each of the modules is as described in FIGS. 7A to 7G.

Then, the digital instructions may be provided to a patient (S830). In this case, the digital instructions may be provided in the form of digital instructions which are associated with behaviors, emotions, cognition and in which the patient's instruction adherence such as eye exercise/physical exercise may be monitored using a sensor, or provided in the form of digital instructions in which a patient is allowed to directly input the execution outcomes.

After the patient executes the presented digital instructions, the patient's execution outcomes of the digital instructions may be collected (S840). In S840, the execution outcomes of the digital instructions may be collected by monitoring the patient's adherence to the digital instructions as described above, or allowing the patient to input the execution outcomes of the digital instructions.

Meanwhile, the digital application for treating myopia according to one embodiment of the present disclosure may repeatedly execute operations several times, wherein the operations include generating the digital instruction and collecting the patient's execution outcomes of the digital instructions. In this case, the generating of the digital instruction may include generating the patient's digital instructions for this cycle based on the patient's digital instructions provided in the previous cycle and the execution outcome data on the patient's collected digital instructions provided in the previous cycle.

As described above, according to the digital application for treating myopia according to one embodiment of the present disclosure, the reliability of the inhibition of progression of and treatment of myopia may be ensured by deducing the mechanism of action in and the therapeutic hypothesis for myopia in consideration of the neurohumoral factors for myopia, presenting the digital instructions to a patient based on the mechanism of action in and the therapeutic hypothesis for myopia, executing the digital instructions under a suitable light stimulus environment, and collecting and analyzing the outcomes of the digital instructions.

Although the digital apparatus and the application for treating myopia according to one embodiment of the present disclosure have been described in terms of myopia therapy, the present disclosure is not limited thereto. For the other diseases other than the myopia, the digital therapy may be executed substantially in the same manner as described above.

Figure 9:
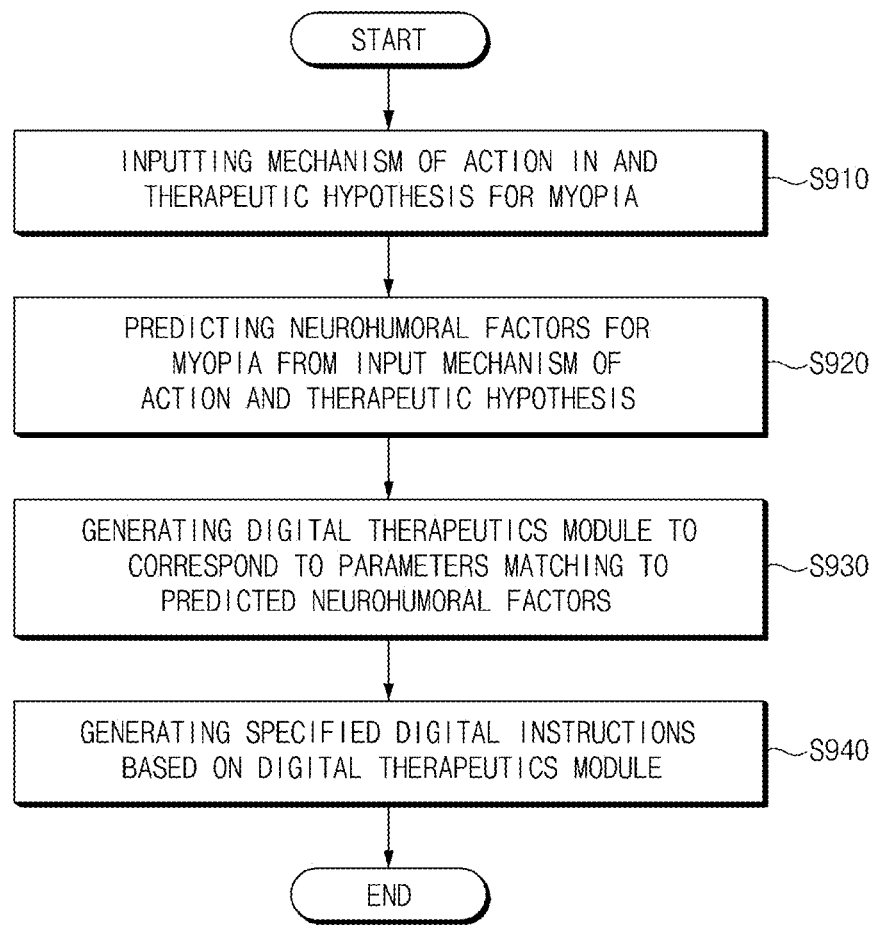
FIG. 9 is a flowchart illustrating a method of generating digital instructions in the digital application for treating myopia according to one embodiment of the present disclosure.

FIG. 9 is a flowchart illustrating a method of generating digital instructions in the digital application for treating myopia according to one embodiment of the present disclosure.

Referring to FIG. 9, operations of the method of generating digital instructions are as described above in the process of generating the module for treating myopia and the specified digital instructions based on the mechanism of action in and the therapeutic hypothesis for myopia (S810 and S820 shown in FIG. 8) and the processes shown in FIG. 5.

In S910, first of all, the mechanism of action in and the therapeutic hypothesis for myopia may be input. In this case, the mechanism of action in and the therapeutic hypothesis for myopia may be previously deduced through the literature search and expert reviews on the systematic related clinical trials on myopia, as described above.

Next, neurohumoral factors for myopia may be predicted from the input mechanism of action and therapeutic hypothesis (S920). In this case, the neurohumoral factors for myopia predicted in S920 may be deduced in the form of IGF, cortisol, dopamine, and the like. These neurohumoral factors have been described in detail with reference to FIG. 5, and thus description thereof will be omitted.

In S930, a digital therapeutics module may be generated so that the imaginary parameters may correspond to the predicted neurohumoral factors. Here, the imaginary parameters may serve as converters that convert the neurohumoral factors for myopia into a digital therapeutics module, and this procedure is to set the physiological interrelation between the neurohumoral factors and the environmental, behavioral, emotional and cognition factors, as shown in FIG. 5.

Then, specified digital instructions may be generated based on the generated digital therapeutics module (S940). In this case, the specific digital instructions may be generated at the aforementioned light environment setup, eye exercise, physical exercise, ego, safety/comfort, fun, and accomplishment modules with reference to FIGS. 7A to 7G.

Figure 10:
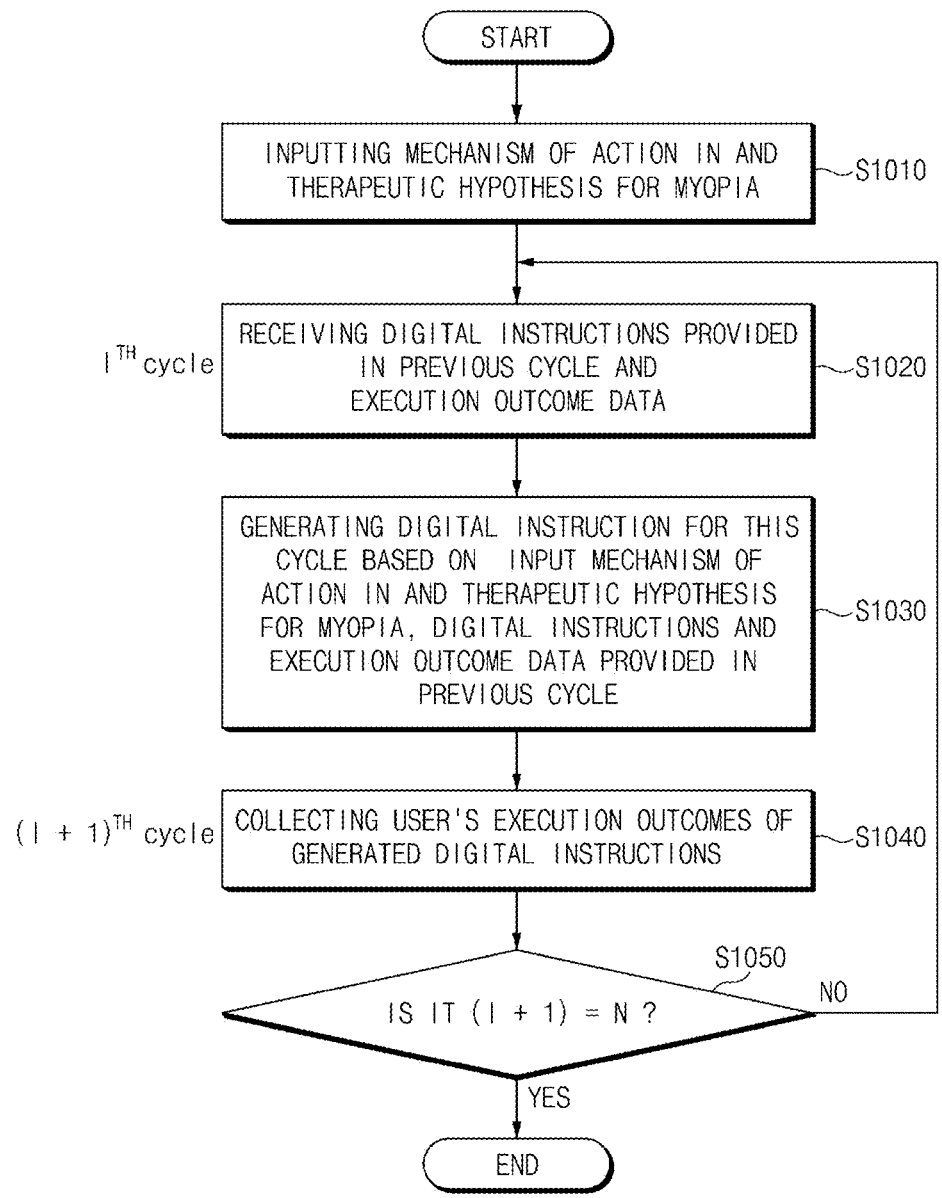
FIG. 10 is a flowchart illustrating a method of repeatedly executing the operations under the feedback control in the digital application for treating myopia according to one embodiment of the present disclosure.

FIG. 10 is a flowchart illustrating a method of repeatedly executing the operations under the feedback control in the digital application for treating myopia according to one embodiment of the present disclosure.

In FIG. 10, it is explained that generation of the digital instructions and collection of the execution outcomes at the digital application for treating myopia are executed N times. In this case, the mechanism of action in and the therapeutic hypothesis fir myopia may be first input (S1010). Also, the digital instructions provided in the previous cycle, and the execution outcome data may be received (S1020). When the first cycle of execution is now in progress, S1020 may be omitted because there are no previous data.

Next, digital instructions for this cycle may be generated based on the input mechanism of action and therapeutic hypothesis, the digital instruction provided in the previous cycle, and the execution outcome data (S1030). Then, the user's execution outcomes of the generated digital instructions may be collected (S1040).

In S1050, it is judged whether this cycle is greater than $N^{th}$ cycle. When this cycle is less than the $N^{th}$ cycle (NO), this may return again to S1020, thus repeatedly executing S1020 to S1040. On the other hand, when this cycle is greater than the $N^{th}$ cycle (YES), that is, when the generation of the digital instructions and the collection of the execution outcomes are executed N times, a feedback operation may be terminated.

Figure 11:
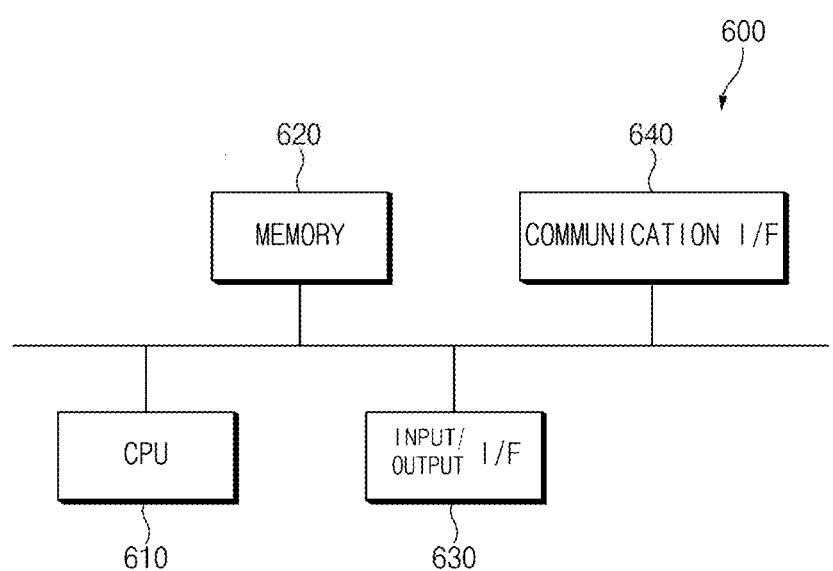
FIG. 11 is a diagram showing a hardware configuration of the digital apparatus for treating myopia according to one embodiment of the present disclosure.

FIG. 11 is a diagram showing a hardware configuration of the digital apparatus for treating myopia according to one embodiment of the present disclosure.

Referring to FIG. 11, hardware 600 of the digital apparatus for treating myopia according to one embodiment of the present disclosure may include a CPU 610, a memory 620, an input/output I/F 630, and a communication I/F 640.

The CPU 610 may be a processor configured to execute a digital program for treating myopia stored in the memory 620, process various data for treating digital myopia and execute functions associated with the digital myopia therapy. That is, the CPU 610 may act to execute functions for each of the configurations shown in FIG. 2 by executing the digital program for treating myopia stored in the memory 620.

The memory 620 may have a digital program for treating myopia stored therein. Also, the memory 620 may include the data used for the digital myopia therapy included in the aforementioned database 050, for example, the patient's digital instructions and instruction execution outcomes, the patient's medical information, and the like.

A plurality of such memories 620 may be provided, when necessary. The memory 620 may be a volatile memory or a non-volatile memory. When the memory 620 is a volatile memory, RAM, DRAM, SRAM, and the like may be used as the memory 620. When the memory 620 is a non-volatile memory, ROM, PROM, EAROM, EPROM, EEPROM, a flash memory, and the like may be used as the memory 620. Examples of the memories 620 as listed above are given by way of illustration only, and are not intended to limit the present disclosure.

The input/output I/F 630 may provide an interface in which input apparatuses (not shown) such as a keyboard, a mouse, a touch panel, and the like, and output apparatuses such as a display (not shown), and the like may transmit and receive data (e.g., wirelessly or by hardline) to the CPU 610.

The communication I/F 640 is configured to transmit and receive various types of data to/from a server, and may be one of various apparatuses capable of supporting wire or wireless communication. For example, the types of data on the aforementioned digital behavior-based therapy may be received from a separately available external server through the communication I/F 640.

As described above, the computer program according to one embodiment of the present disclosure may be recorded in the memory 620 and processed at the CPU 610, for example, so that the computer program may be realized as a module configured to execute each of functional blocks shown in FIG. 2.

According to the digital apparatus and the application for treating axial myopia according to the present disclosure, a reliable digital apparatus and application capable of inhibiting progression of and treating myopia may be provided by deducing a mechanism of action in myopia and a therapeutic hypothesis and a digital therapeutic hypothesis for myopia in consideration of neurohumoral factors for progression of axial myopia, presenting digital instructions to a patient under suitable light stimulus environment setups based on the mechanism of action, the therapeutic hypothesis, and the digital therapeutic hypothesis, and collecting and analyzing execution outcomes of the digital instructions.

While the disclosure has been shown and described with reference to certain exemplary embodiments thereof, it will be understood by those skilled in the art that various changes in form and details may be made therein without departing from the spirit and scope of the disclosure as defined by the appended claims.

BRIEF DESCRIPTION OF MAIN PARTS IN THE DRAWINGS

000: digital myopia therapy system
010: digital instruction generation unit
020: sensing data collection unit
030: execution input unit
040: outcome analysis unit
050: database
060: security unit
600: digital myopia therapy apparatus 610: CPU
620: memory
630: input/output I/F
640: communication I/F

What is claimed is:

1. A method of treating myopia in a subject, the method comprising:
providing, by a digital apparatus to the subject, a digital application comprising at least one module selected from the group consisting of eye exercise module, a relaxation module, and a light therapy module for treating myopia based on a mechanism of action in and a therapeutic hypothesis for the myopia, each of the at least one module comprising one or more first instructions for the subject to follow,
wherein the digital apparatus (i) comprises a sensor sensing adherence to the at least one module by the subject to the one or more first instructions of the at least one module, (ii) transmits adherence information, based on the adherence, to a server accessible by a healthcare provider through a healthcare provider portal, and (iii) receives one or more second instructions of the at least one module from the healthcare provider based on the adherence information, and
the digital application instructs a processor of the digital apparatus to execute operations comprising collecting the subject's execution outcomes of said one or more first instructions, the collecting comprises determining one or both of an exercise intensity (EI) and an average exercise intensity (AEI).

2. The method of claim 1, wherein the digital application instructs a processor of the digital apparatus to execute operations comprising:
generating said at least one module based on the mechanism of action in and the therapeutic hypothesis for the myopia.

3. The method of claim 2, wherein the generating comprises generating said at least one module based on neurohumoral factors related to onset of the myopia.

4. The method of claim 2, further comprising generating a calibration module for calibrating one or more of an accuracy of measurement of the subject's eye position, and a light environment.

5. The method of claim 4, wherein the calibration module is generated prior to generating said at least one module.

6. The method of claim 4, wherein the accuracy of measurement of the subject's eye position is calibrated, and said calibrating the accuracy of measurement of the subject's eye position comprises one or more of instructing the subject to position the subject's face to appear on a screen of the digital apparatus, detecting the subject's eyes for a given period of time, instructing the subject to blink the subject's eyes, detecting if the subject blinked the subject's eyes, instructing the subject to stare at the screen, instructing the subject to move the subject's eyes in a given direction or rotate the subject's eyes, and determining a threshold for detecting the subject's eyes.

7. The method of claim 6, wherein the digital apparatus comprises one or more sensors for tracking movement of the subject's eyeball.

8. The method of claim 4, wherein the accuracy of measurement of the light environment is calibrated, and said calibrating the light environment comprises one or more of detecting light in the subject's environment using a light sensor of the digital apparatus, and instructing the subject to turn on one or more lights in environment.

9. The method of claim 8, wherein the digital application instructs a processor of the digital apparatus to execute operations comprising:
generating said at least one module based on the mechanism of action in and the therapeutic hypothesis for the myopia;
generating said one or more first instructions based on the digital therapeutic modules; and
providing the generated instructions to the subject.

10. The method of claim 9, wherein the generating of said one or more first instructions is repeatedly executed with multiple feedback loops, and
the generating comprises generating the subject's digital instructions for a second cycle based on said one or more first instructions in a first cycle and the subject's execution outcomes on said one or more first instructions provided in the first cycle.

11. The method of claim 9, wherein the generating of said one or more first instructions comprises generating the at least one module by applying parameters about the subject's environments, behaviors, emotions, and cognition to the mechanism of action in and the therapeutic hypothesis for the myopia.

12. The method of claim 1, wherein the digital application instructs a processor of the digital apparatus to generate the at least one module, and wherein the at least one module comprises two or more modules selected from the group consisting of an eye exercise module, a relaxation module, and a light therapy module.

13. The method of claim 12, wherein
the eye exercise module comprises one or more exercise instructions for one or more of: eyeball exercise instructions, biofeedback control instructions, and eyeball-related behavior control instructions;
the relaxation module comprises one or more relaxation instructions for one or more of: physical exercise instructions, ego enhancement instructions, safety feeling instructions, comfort feeling instructions, and fun instructions; and
the light therapy module comprises one or more light therapy instructions for controlling a light environment of the subject.

14. The method of claim 13, wherein the one or more relaxation instructions comprise one or more of playing a sound or song, inducing blinking, and instructing the subject to perform gymnastics.

15. The method of claim 12, wherein the at least one module further comprises an accomplishment module comprising one or more accomplishment instructions for task accomplishment and for providing compensation for the subject's adherence to instructions of the at least one module.

16. The method of claim 12, wherein the at least one module further comprises a fun module comprising one or more fun instructions for music, games, or videos.

17. The method of claim 1, wherein the healthcare provider portal is configured to provide one or more options to the healthcare provider to perform one or more tasks to prescribe treatment for the myopia in the subject based on the adherence information, and wherein the one or more options provided to the healthcare provider are selected from the group consisting of adding or removing the subject, viewing or editing personal information for the subject, viewing adherence information for the subject, viewing a result of the subject for one or more at least partially completed digital therapeutic modules, prescribing one or more digital therapeutic modules to the subject, altering a prescription for one or more digital therapeutic modules, and communicating with the subject.

18. The method of claim 17, wherein the one or more options comprise viewing or editing personal information for the subject, and the personal information comprises one or more selected from the group consisting of an identification number for the subject, a name of the subject, a date of birth of the subject, an email of the subject, an email of a guardian of the subject, a contact phone number for the subject, a prescription for the subject, and one or more notes made by the healthcare provider about the subject.

19. The method of claim 18, wherein the personal information comprises the prescription for the subject, and the prescription for the subject comprises one or more selected from the group consisting of a prescription identification number, a prescription type, a start date, a duration, a completion date, a number of scheduled or prescribed digital therapeutic modules to be performed by the subject, and a number of scheduled or prescribed digital therapeutic modules to be performed by the subject per day.

20. The method of claim 17, wherein the one or more options comprise the viewing the adherence information, and the adherence information of the subject comprises one or more of a number of scheduled or prescribed digital therapeutic modules completed by the subject, and a calendar identifying one or more days on which the subject completed, partially completed, or did not complete one or more scheduled or prescribed digital therapeutic modules.

21. The method of claim 17, wherein the one or more options comprise the viewing the result of the subject, and the result of the subject for one or more at least partially completed digital therapeutic modules comprises one or more selected from the group consisting of a time at which the subject started a scheduled or prescribed digital therapeutic module, a time at which the subject ended a scheduled or prescribed digital therapeutic module, an indicator of whether the scheduled or prescribed digital therapeutic module was fully or partially completed, and an exercise intensity (EI).

22. The method of claim 1, wherein the server is accessible by an administrator through an administrative portal configured to provide one or more options to an administrator of the system to perform one or more tasks to manage access to the system by the healthcare provider, and wherein the one or more options provided to the administrator of the system are selected from the group consisting of adding or removing the healthcare provider, viewing or editing personal information for the healthcare provider, viewing or editing de-identified information of the subject, viewing adherence information for the subject, viewing a result of the subject for one or more at least partially completed digital therapeutic modules, and communicating with the healthcare provider.

23. The method of claim 1, wherein the subject is a child.

24. The method of claim 1, wherein the subject is assisted or supervised by an adult.

25. The method of claim 1, wherein the digital apparatus comprises:
 a digital instruction generation unit configured to generate said at least one module based on the mechanism of action in and the therapeutic hypothesis for the myopia, generate said one or more first instructions based on the digital therapeutic modules, and provide the one or more first instructions to the subject; and
 an outcome collection unit configured to collect the subject's execution outcomes of the one or more first instructions.

26. The method of claim 25, wherein the digital instruction generation unit generates the at least one module based on neurohumoral factors related to the myopia onset.

27. The method of claim 26, wherein the neurohumoral factors comprise insulin-like growth factor (IGF), cortisol, and dopamine.

28. The method of claim 1, wherein AEI is determined as an averaged sum of differences between a final location of an eyeball of the subject and a starting location of the eyeball measured at a predetermined interval.

29. The method of claim 28, wherein the predetermined interval is between about 10 milliseconds (ms) and about 500 ms.

30. The method of claim 1, wherein the EI is determined according formula:

$$EI = \frac{AEI \times 100}{145}.$$

31. The method of claim 1, wherein the AEI is determined as a sum of static AEI and dynamic AEI.

32. The method of claim 22, wherein the one or more options comprise the viewing or editing the personal information, and the personal information of the healthcare provider comprises one or more selected from the group consisting of an identification number for the healthcare provider, a name of the healthcare provider, an email of the healthcare provider, and a contact phone number for the healthcare provider.

33. The method of claim 22, wherein the one or more options comprise the viewing or editing the de-identified information of the subject, and the de-identified information of the subject comprises one or more selected from the group consisting of an identification number for the subject, and the healthcare provider for the subject.

34. The method of claim 22, wherein the one or more options comprise the viewing the adherence information for the subject, and the adherence information of the subject comprises one or more of a number of scheduled or prescribed digital therapeutic modules completed by the subject, and a calendar identifying one or more days on which the subject completed, partially completed, or did not complete one or more scheduled or prescribed digital therapeutic modules.

35. The method of claim 22, wherein the one or more options comprise the viewing the result of the subject, and the result of the subject for one or more at least partially completed digital therapeutic modules comprises one or more selected from the group consisting of a time at which the subject started a scheduled or prescribed digital therapeutic module, a time at which the subject ended a scheduled or prescribed digital therapeutic module, an indicator of whether the scheduled or prescribed digital therapeutic module was fully or partially completed, and an exercise intensity (EI).

36. The method of claim 1, wherein the digital application further comprises a push alarm for one or more of reminding the subject complete a digital therapeutic module and adjusting a light setting of environment of the subject.

37. The method of claim 36, wherein the push alarm is activated to remind the subject to adjust the light setting, such that the subject is exposed to light at least 3 times per day.

38. The method of claim 23, wherein the subject is less than about 20 years old, less than about 15 years old, less than about 10 years old, or less than about 5 years old.

39. The method of claim 25, wherein the digital instruction generation unit generates the digital therapeutic modules based on the inputs from the healthcare provider.

40. The method of claim 25, wherein the digital instruction generation unit generates the digital therapeutic modules based on information received from the subject.

41. The method of claim 40, wherein the information is received from the subject comprises at least one of basal factors, medical information, and digital therapeutics literacy of the subject, the basal factors including the subject's activity, heart rate, sleep, and diet, the medical information including the subject's electronic medical record (EMR), family history, genetic vulnerability, and genetic susceptibility, and the digital therapeutics literacy including the subject's accessibility, and technology adoption to the digital therapeutics and the apparatus.

42. The method of claim 25, wherein the outcome collection unit collects the execution outcomes of the digital instructions by monitoring the subject's adherence to the digital instructions or allowing the subject to directly input the subject's adherence to the digital instructions.

43. The method of claim 25, wherein the generation of the digital instructions at the digital instruction generation unit and the collection of the subject's execution outcomes of the digital instructions at the outcome collection unit are repeatedly executed with multiple feedback loops, and the digital instruction generation unit generates the subject's digital instructions based on the subject's digital instructions previously generated and the execution outcome data on the subject's digital instructions previously collected at the outcome collection unit.

* * * * *